US009181546B2

(12) United States Patent
Li et al.

(10) Patent No.: US 9,181,546 B2
(45) Date of Patent: *Nov. 10, 2015

(54) COMPOSITIONS FOR BACTERIAL MEDIATED GENE SILENCING AND METHODS OF USING SAME

(75) Inventors: Chiang Li, Cambridge, MA (US); Johannes Fruehauf, Boston, MA (US); Shuanglin Xiang, Boston, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 405 days.

This patent is subject to a terminal disclaimer.

(21) Appl. No.: 13/196,436

(22) Filed: Aug. 2, 2011

(65) Prior Publication Data

US 2012/0093773 A1    Apr. 19, 2012

Related U.S. Application Data

(63) Continuation of application No. 11/793,429, filed as application No. PCT/US2005/045513 on Dec. 16, 2005, now abandoned.

(60) Provisional application No. 60/637,277, filed on Dec. 17, 2004, provisional application No. 60/651,238, filed on Feb. 8, 2005.

(51) Int. Cl.
*C12N 15/63* (2006.01)
*C12N 15/11* (2006.01)
(Continued)

(52) U.S. Cl.
CPC .......... *C12N 15/111* (2013.01); *C12N 15/1135* (2013.01); *C12N 15/1138* (2013.01); *C12N 15/8218* (2013.01); *C12N 2310/111* (2013.01);
(Continued)

(58) Field of Classification Search
CPC ..... C12N 15/111; C12N 15/1135; C12N 35/74
See application file for complete search history.

(56) References Cited

U.S. PATENT DOCUMENTS 4,683,195 A    7/1987   Mullis et al.
6,500,419 B1   12/2002  Hone et al.
(Continued)

FOREIGN PATENT DOCUMENTS

WO   WO-9918221 A1   4/1999
WO   WO-9934007 A1   7/1999
WO   WO-0297114 A2   5/2002
(Continued)

OTHER PUBLICATIONS

Abraham et al. "IL-23 and Autoimmunity: New Insights into the Pathogenesis of Inflammatory Bowel Disease." *Annu. Rev. Med.* 60(2009):97-110.

(Continued)

*Primary Examiner* — Jon E Angell
(74) *Attorney, Agent, or Firm* — Eckman Basu LLP

(57) ABSTRACT

Methods are described for the delivery of one or more small interfering RNAs (siRNAs) to a eukaryotic cell using a bacterium. Methods are also described for using this bacterium to regulate gene expression in eukaryotic cells using RNA interference, and methods for treating cancer of cell proliferative disorders. The bacterium includes one or more siRNAs or one or more DNA molecules encoding one or more siRNAs. Vectors are also described for use with the bacteria of the invention for causing RNA interference in eukaryotic cells.

7 Claims, 19 Drawing Sheets

(51) Int. Cl.
C12N 15/113 (2010.01)
C12N 15/82 (2006.01)
(52) U.S. Cl.
CPC ......... C12N 2310/14 (2013.01); C12N 2320/32 (2013.01)

(56) References Cited

U.S. PATENT DOCUMENTS

| | | |
|---|---|---|
| 2004/0259247 A1 | 12/2004 | Tuschl et al. |
| 2008/0311081 A1 | 12/2008 | Fruehauf et al. |

FOREIGN PATENT DOCUMENTS

| | | |
|---|---|---|
| WO | WO-2006007569 A2 | 1/2006 |
| WO | WO-2006021894 A2 | 3/2006 |
| WO | WO-2006066048 A2 | 6/2006 |
| WO | WO-2008012695 A2 | 1/2008 |
| WO | WO-2008156661 A2 | 12/2008 |
| WO | WO-2008156702 A2 | 12/2008 |

OTHER PUBLICATIONS

Ahrenholtz et al. "A Conditional Suicide System in *Escherichia coli* Based on the Intracellular Degradation of DNA." *Appl. Envir. Microbiol.* 60.10(1994):3746-3751.
Ahrens et al. "Intestinal Macrophage/Epithelial Cell-Derived CCL11/Eotaxin-1 Mediates Eosinophil Recruitment and Function in Pediatric Ulcerative Colitis." *J. Immunol.* 181.10(2008):7390-7399.
Al-Hendy et al. "Lipopolysaccharide O Side Chain of *Yersinia enterocolitica* O:3 is an Essential Virulence Factor in an Orally Infected Murine Model." *Infect. Immun.* 60.3(1992):870-875.
Al-Mariri et al. "*Yersinia enterocolitica* as a Vehicle for a Naked DNA Vaccine Encoding *Brucella abortus* Bacterioferritin or P39 Antigen." *Infect. Immun.* 70.4(2002):1915-1923.
Alphen et al. "Influence of Osmolarity of the Growth Medium on the Outer Membrane Protein Pattern of *Escherichia coli*." *J. Bacteriol.* 131.2(1977):623-630.
Bader et al. "Recognition of Antimicrobial Peptides by a Bacterial Sensor Kinase." *Cell.* 122.3(2005):461-472.
Battistoni et al. "Increased Expression of Periplasmic Cu,Zn Superoxide Dismutase Enhances Survival of *Escherichia coli* Invasive Strains within Nanphagocytic Cells." *Infect. Immun.* 68.1(2000):30-37.
Bhatia et al. "Treatment with Bindarit, an Inhibitor of MCP-1 Synthesis, Protects Mice Against Trinitrobenzene Sulfonic Acid-Induced Colitis." *Inflamm. Res.* 57.10(2008):464-471.
Bielecki et al. "*Bacillus subtilis* Expressing a Haemolysin Gene from *Listeria monocytogenes* can Grown in Mammalian Cells." *Nature.* 345(1990):175-176.
Bienkowski-Szewczyk et al. "The R Gene Product of Bacteriophage λ is the Murein Transglycylase." *Mol. Gen. Genet.* 184(1981):111-114.
Bitko et al. "Inhibition of Respiratory Viruses by Nasally Administered siRNA." *Nat. Med.* 11.1(2005):50-55.
Black et al. "Prevention of Shigellosis by a *Salmonella typhi-Shigella sonnei* Bivalent Vaccine." *J. Infect. Dis.* 155.6(1987):1260-1265.
Blankenhorn et al. "Acid- and Base-Induced Proteins During Aerobic and Anaerobic Growth of *Escherichia coli* Revealed by Two-Dimensional Gel Eelectrophoresis." *J. Bacteriol.* 181.7(2999)2209-2216, (1999).
Bouma et al. "The Immunological and Genetic Basis of Inflammatory Bowel Disease." *Nat. Rev. Immunol.* 3.7(2003):521-533.
Bridge et al. "Induction of an Interferon Response by RNAi Vectors in Mammalian Cells." *Nat. Genet.* 34.3(2003):263-264.
Brummelkamp et al. "A System for Stable Expression of Short Interfering RNAs in Mammalian Cells." *Science.* 296(2002):550-553.
Brummelkamp et al. "Stable Suppression of Tumorigenicity by Virus-Mediated RNA Interference." *Cancer Cell.* 2(2002):243-247.

Brundage et al. "Expression and Phosphorylation of the *Listeria monocytogenes* ActA Protein in Mammalian Cells." *PNAS.* 90(1993):11890-11894.
Buchmeier et al. "Induction of *Salmonella* Stress Proteins Upon Infection of Macrophages." *Science.* 248(1990):730-732.
Buchmeier et al. "Recombination-Deficient Mutants of *Salmonella typhimurium* are Avirulent and Sensitive to the Oxidative Burst of Macrophages." *Mol. Microbiol.* 7.6(1993):933-936.
Butz et al. "siRNA Targeting of the Viral E6 Oncogene Efficiently Kills Human Papillomavirus-Positive Cancer Cells." *Oncogene.* 22.38(2003):5938-5945.
Calin-Jageman et al. "Mutational Analysis of an RNA Internal Loop as a Reactivity Epitope for *Escherichia coli* Ribonuclease III Substrates." *Biochem.* 42.17(2003):5025-5034.
Camilli et al. "*Listeria monocytogenes* Mutants Lacking Phosphatidylinositol-Specific Phospholipase C are Avirulent." *J. Exp. Med.* 173(1991):751-754.
Caplan et al. "Specific Inhibition of Gene Expression by Small Double-Stranded RNAs in Invertebrate and Vertebrate Systems." *PNAS.* 98.17(2001):9742-9747.
Chamberlain et al. "*Neisseria gonorrhoeae* Strain MS11 Harbouring a Mutation in Gene *aroA* is Attenuated and Immunogenic." *Micro. Path.* 15(1993):51-63.
Cooper et al. "Invasiveness and Persistence of *Salmonella enteritidis, Salmonella typhimurium,* and a Genetically Defined *S. enteritidis aroA* Strain in Young Chickens." *Infect. Immun.* 62.11(1994):4739-4746.
Courvalin et al. "Gene Transfer from Bacteria to Mammalian Cells." *C.R. Acad. Sci. Paris, Life Sci.* 318(1995):1207-1212.
Cromie et al. "An RNA Sensor for Intracellular Mg2+." *Cell.* 125(2006):71-84.
Curtiss et al. "*Salmonella typhimurium* Deletion Mutants Lacking Adenylate Cyclase and Cyclic AMP Receptor Protein are Avirulent and Immunogenic." *Infect. Immun.* 55.12(1987):3035-3043.
D'Hauteville et al. "Phosphorylation of IcsA by cAMP-Dependent Protein Kinase and its Effect on Intercellular Spread of *Shigella flexneri.*" *Mol. Microbiol.* 6.7(1992):833-841.
Darji et al. "Oral Somatic Transgene Vaccination Using Attenuated S. typhimiruim." *Cell.* 91(1997):765-775.
Datsenko et al. "One-Step Inactivation of Chromosomal Genes in *Escherichia coli* K-12 Using PCR Products." *PNAS.* 97.12(2000):6640-6645.
de Boer et al. "A Division Inhibitor and a Topological Specificity Factor Coded for by the Minicell Locus Determined Proper Placement of the Division Septum in E. coli." *Cell.* 56.4(1989):641-649.
de Boer et al. "The *tac* Promoter: A Functional Hybrid Derived from the *trp* and *lac* Promoters." *PNAS.* 80.1(1982):21-25.
Devine et al. "Cationic Peptides: Distribution and Mechanisms of Resistance." *Curr. Pharm. Des.* 8.9(2002):703-714.
Dietrich et al. "Delivery of Antigen-Encoding Plasmid DNA into the Cytosol of Macrophages by Attenuated Suicide *Listeria Monoctyogenes.*" *Nat. Biochtechnol.* 16.2(1998):181-185.
Dillon et al. "RNAi as an Experimental and Therapeutic Tool to Study and Regulate Physiological and Disease Processes." *Annu. Rev. Physiol.* 67(2005):147-173.
Dinarello et al. "IL-32, a Novel Cytokine with a Possible Role in Disease." *Ann. Rheum. Dis.* 65.S3(2006):61-64.
Donnenberg et a. "Internalization of *Escherichia coli* into Human Kidney Epithelial Cells: Comparison of Fecal and Pyelonephritis-Associated Strains." *J. Infect. Dis.* 169.4(1994):831-838.
Dorman et al. "Characterization of Porin and ompR Mutants of a Virulent Strain of *Salmonella typhimurium:* ompR Mutants are Attenuated In Vivo." *Infect. Immun.* 57.7(1989):2136-2140.
Duncan et al. "Bacterial Penetration of Bladder Epithelium Through Lipid Rafts: Manuscript M400769200." *JBC Papers in Press.* (2004):1-37.
Dykxhoorn et al. "The Silent Revolution: RNA Interference as Basic Biology, Research Tool, and Therapeutic." *Annu. Rev. Med.* 56(2005):401-423.
Eguchi et al. "Transcriptional Regulation of Drug Efflux Genes by EvgAS, as Two-Component System in *Escherichia coli.*" *Microbiol.* 149.10(2003):2819-2828.

(56) References Cited

OTHER PUBLICATIONS

Elbashir et al. "Duplexes of 21-Nucleotide RNAs Mediate RNA Interference in Cultured Mammalian Cells." *Nature*. 411(2001):494-498.
Elbashir et al. "RNA Interference is Mediated by 21- and 22-Nucleotide RNAs." *Genes Dev*. 15.2(2001):188-200.
Elsinghorst et al. "Molecular Cloning of Epithelial Cell Invasion Determinants from Enterotoxigenic *Escherichia coli*." *Infect. Immun*. 60.6(1992):2409-2417.
Estrem et al. "Identification of an UP Element Consensus Sequence for Bacterial Promoters." *PNAS*. 95.17(1998):9761-9766.
Falkow et al. "The Interaction of Bacteria with Mammalian Cells." *Annu. Rev. Cell Biol*. 8(1992):333-363.
Fantini et al. "IL-21 Comes of Age as a Regulator of Effector T Cells in the Gut." *Muscosal. Immunol*. 1.2(2008):110-115.
Fantini et al. "IL-21 Regulates Experimental Colitis by Modulating the Balance Between Treg and Th17 Cells." *Eur. J. Immunol*. 37.11(2007):3155-3163.
Fantini et al. "New Players in the Cytokine Orchestra of Inflammatory Bowel Disease." *Inflamm. Bowel Dis*. 13.11(2007):1419-1423.
Feng et al. "Dual Regulation by Phospho-OmpR of ssrA/B Gene Expression in *Salmonella*Pathogenicity Island 2." *Mol. Microbiol*. 48.4(2003):1131-1143.
Fina et al. "Regulation of Gut Inflammation and Th17 Cell Response by Interleukin-21." *Gastroenterology*. 134.4(2008):1038-1048.
Fire et al. "Potent and Specific Genetic Interference by Double-Stranded RNA in *Caenorhabditis elegans.*" *Nature*. 391(1998):806-811.
Fontaine et al. "Construction and Evaluation of Live Attenuated Vaccine Strains of *Shigella flexneri* and *Shigella dysenteriae* 1." *Res. Microbiol*. 141.7-8(1990):907-912.
Formal et al. "Oral Vaccination of Monkeys with an Invasive *Escherichia coli* K-12 Hybrid Expressing *Shigella flexneri* 2a Somatic Antigen." *Infect. Immun*. 46.2(1984):465-469.
Fruehauf. "Treatment of Gastrointestinal Targets Using RNA Interference." Oral Presentation, *RNAi World Congress: Boston* (Apr. 30-May 2, 2008).
Galinski et al. "A Reticulocyte-Binding Protein Complex of Plasmodium vivax Merozoites." *Cell*. 69.7(1992):1213-1226.
Galán et al. "Expression of *Salmonella typhimurium* Genes Required for Invasion is Regulated by Changes in DNA Supercoiling." *Infect. Immun*. 58.6(1990):1879-1885.
Gentschev et al. "*Salmonella* Strain Secreting Active Listeriolysin Changes its Intracellular Localization." *Infect. Immun*. 63.10(1995):4202-4205.
Goldberg et al. "Regulation of Surface Presentation of IcsA, a *Shigella* Protein Essential to Intracellular Movement and Spread, is Growth Phase Dependent." *Infect. Immun*. 62.12(1994):5664-5668.
Gorfinkiel et al. "Sequence and Regulation of the *uap*A Gene Encoding a Uric Acid-xanthine Permease in the Fungus *Aspergillus nidulans.*" *J. Biol. Chem*. 268.31(1993):23376-23381.
Grillot-Courvalin et al. "Functional Gene Transfer from Intracellular Bacteria to Mammalian Cells." *Nat. Biotechnol*. 16(1998):862-866.
Grimm et al. "Fatality in Mice Due to Oversaturation of Cellular microRNA/Short Hairpin RNA Pathways." *Nature*. 441(2006):537-541.
Groisman et al. "*Salmonella typhimurium phoP* Virulence Gene is a Transcriptional Regulator." *PNAS*. 86.18(1989):7077-7081.
Groisman et al. "The Pleiotropic Two-Component Regulatory System PhoP-PhoQ." *J. Bacteriol*. 183.6(2001):1835-1842.
Gu et al. "Inhibition of Cervical Cancer Cell Growth in vitro and in vivo with Lentiviral-Vector Delivered Short Hairpin RNA Targeting Human Papillomavirus E6 and E7 Oncogenes." *Cancer Gene Ther*. 13.11(2006):1023-1032.
Gu et al. "siRNA and shRNA as Anticancer Agents in a Cervical Cancer Model." *Meth. Mol. Biol*. 442(2008):159-172.
Gustafson et al. "Mutagenesis of the Paracystalline Surface Protein Array of *Aeromonas salmonicida* by Endogenous Insertion Elements." *J. Mol. Biol*. 237.4(1994):452-463.

Hacein-Bey-Abina et al. "A Serious Adverse Event after Successful Gene Therapy for X-Linked Severe Combined Immunodeficiency." *N. Eng. J. Med*. 348.3(2003):255-256.
Harborne et al. "Transcriptional Control, Translation and Function of the Products of the Five Open Reading Frames of the *Escherichia coli nir* Operon." *Mol. Microbiol*. 6.19(1992):2805-2813.
Harborth et al. "Sequence, Chemical, and Structural Variation of Small Interfering RNAs and Short Hairpin RNAs and the Effect on Mammalian Gene Silencing." *Antisense Nucl. Acid Drug Dev*. 13.2(2003):83-105.
Heidrich et al. "Involvement of N-Acetylmuramyl-L-Alanine Amidases in Cell Separation and Antibiotic-Induced Autolysis of *Escherichia coli.*" *Mol. Microbiol*. 41.1(2001):167-178.
Heller et al. "Interleukin-13 is the Key Effector Th2 Cytokine in Ulcerative Colitis That Affects Epithelial Tight Junctions, Apoptosis, and Cell Restitution." *Gastroenterology*. 129.2(2005):550-564.
Hense et al. "Eukaryotic Expression Plasmid Transfer from the Intracellular Bacterium *Listeria monocytogenes* to Host Cells." *Cell. Microbiol*. 3.9(2001):599-609.
Hernandez-Chico et al. "Gene *ompR* and Regulation of Microcin 17 and Colicin e2 Syntheses." *J. Bacteriol*. 152.2(1982):897-900.
Hess et al. "*Listeria monocytogenes* p60 Supports Host Cell Invasion by and In Vivo Survival of Attenuated *Salmonella typhimurium.*" *Infect. Immun*. 63.5(1995):2047-2053.
Hjalt et al. "Bulged-Out Nucleotides Protect an Antisense Rna from RNase III Cleavage." *Nuc. Acids Res*. 23.4(1995):571-579.
Hoiseth et al. "Aromatic-Dependent *Salmonella typhimurium* are Non-Virulent and Effective as Live Vaccines." *Nature*. 291(1981):238-239.
Holle et al. "Bcl-2 Targeting siRNA Expressed by a T7 Vector System Inhibits Human Tumor Cell Growth in vitro." *Int. J. Oncol*. 24.3(2004):615-621.
Hone et al. "Construction of Defined *galE* Mutants of *Salmonella* for Use as Vaccines." *J. Infect. Dis*.156.1(1987):167-174.
Hone et al. "Construction of Genetically Defined Double *aro*Mutants of *Salmonella typhi.*" *Vacc*. 9.11(1991):810-816.
Hornung et al. "Sequence-Specific Potent Induction of IFN-α by Short Interfering RNA in Plasmacytoid Dendritic Cells Through TLR7." *Nature Med*. 11.3(2005):263-270.
Hou et al. "Study of Claudin Function by RNA Interference." *J. Biol. Chem*. 281.47(2006):36117-36123.
Huang et al. "Phosphorylation Stimulates the Cooperative DNA-Binding Properties of the Transcription Factor OmpR." *PNAS*. 94.7(1997):2828-2832.
Inokuchi et al. "Domains Involved in Osmoregulation of the *ompF* Gene in *Escherichia coli.*" *J. Bacteriol*. 164.2(1985):585-590.
Isberg et al. "A Single Genetic Locus Encoded by *Yersinia pseudotuberculosis* Permits Invasion of Cultured Animal Cells by *Escherichia coli* K-12." *Nature*. 317(1985):262-264.
Isberg et al. "Identification of Invasion: A Protein that Allows Enteric Bacteria to Penetrate Cultured Mammalian Cells." *Cell*. 50(1987):769-778.
Isberg et al. "Two Mammalian Cell Internalization Strategies Used by Pathogenic Bacteria." *Ann. Rev. Genet*. 28(1994):395-422.
Jack et al. "Bacteriocins of Gram-Positive Bacteria." *Microbiol. Rev*. 59.2(1995):171-200.
Jain et al. "Use of Lamda Phage S and R Gene Products in an Inducible Lysis System for *Vibrio cholerae*- and *Salmonella enterica* Serova Typhimurium-Based DNA Vaccine Delivery Systems." *Infect. Immun*. 68.2(2000):986-989.
Jana et al. "RNA Interference: Potential Theapeutic Targets." *Appl. Microbiol. Biotechnol*. 65(2004):649-657.
Jiang et al. "Selective Silencing of Viral Gene Expression in HPV-Positive Human Cervical Carcinoma Cells Treated with siRNA, a Primer of RNA Interference." *Oncogene*. 21(2002):6041-6048.
Johnson et al. "The Role of a Stress-Response Protein in *Salmonella typhimurium* Virulence." *Mol. Microbiol*. 5.2(1991):401-407.
Jones et al. "A Novel *Escherichia coli* Lipoprotein Expression Vector." *Gene*. 165(1995):145-146.
Katchar et al. "MIP-3α Neutralizing Monoclonal Antibody Protects Against TNBS-Induced Colonic Injury and Inflammation in Mice." *Am. J. Physiol. Gastrointest*. 292(2007):G1263-G1271.

(56) References Cited

OTHER PUBLICATIONS

Kato et al. "Molecular Characterization of the PhoP-PhoQ Two-Component System in *Escherichia coli* K-12: Identification of Extracellular Mg2+-Responsive Promoters." *J. Bacteriol.* 181.17(1999):5516-5520.

Kawada et al. "Role of Mammalian Chitinases in Inflammatory Conditions." *Keio J. Med.* 56.1(2007):21-27.

Keates et al. "Cequent Pharmaceuticals, Inc.: The Biological Pitcher for RNAi Therapeutics." *Pharmacogenomics.* 8.7(2007):867-871.

Kim et al. "β-Catenin Activates the Growth Factor Endothelin-1 in Colon Cancer Cells." *Oncogene.* 24(2004):597-604.

Kim et al. "Interleukin-32: A Cytokine and Inducer of TNFα." *Immunity.* 22(2005):131-142.

Kloos et al. "Inducible Cell Lysis System for the Study of Natural Transformation and Environmental Fate of DNA Released by Cell Death." *J. Bacteriol.* 176.23(1994):7352-7361.

Kong et al. "RNA Interference as Novel and Powerful Tool in Immunopharmacological Research." *Int.Immunopharmacology.* 7.4(2007):417-426.

Kotloff et al. "Immunogenicity, and Transmissibility in Humans of CVD 1203, a Live Oral *Shigella flexneri* 2a Vaccine Candidate Attenuated by Deletions in *aroA* and *virG*." *Infect. Immun.* 64.11(1996):4542-4548.

Kwaga et al. "A *carAB* Mutant of Avian Pathogenic *Escherichia coli* Serogroup O2 is Attenuated and Effective as a Live Oral Vaccine Against Colibacillosis in Turkeys." *Infect. Immun.* 62.9(1994):3766-3772.

Kärnell et al. "Auxotrophic Live Oral *Shigella flexneri* Vaccine Protects Monkeys Against Challenge with *S. flexneri* of Different Serotypes." *Vacc.* 10.3(1992):167-174.

Kärnell et al. "Safety and Immunogenicity Study of the Auxotrophic *Shigella flexneri* 2a Vaccine SFL1070 with a Deleted *aroD* Gene in Adult Swedish Volunteers." *Vacc.* 13.1(1995):88-99.

Lazzaroni et al. "Excretion of Alkaline Phosphate by *Escherichia coli* K-12 *pho* Constitutive Mutants Transformed with Plasmids Carrying the Alkaline Phosphatase Structural Gene." *J. Bacteriol.* 164.3(1985):1376-1380.

Lenz. "The RNA Interference Revolution." *Braz. J. Med. Biol. Res.* 38.12(2005):1749-1757.

Leong et al. "Identification of the Integrin Binding Domain of the *Yersinia pseudotuberuclosis* Invasion Protein." *EMBO J.* 9.6(1990):1979-1989.

Lesnik et al. "Prediction of rho-Independent Transcriptional Terminators in *Escherichia coli*." *Nuc. Acids Res.* 29.17(2001):3583-3594.

Levine et al. "Safety, Immunogenicity and Efficacy of Recombinant Live Oral Cholera Vaccines, CVD 103 and CVD 103-HgR." *Lancet.* 2(1988):467-470.

Levine et al. "Safety, Infectivity, Immunogenicity, and in Vivo Stability of Two Attenuated Auxotropic Mutant Strains of *Salmonella thyphi*, 541Ty and 543Ty, as Live Oral Vaccines in Humans." *J. Clin. Invest.* 79(1987):888-902.

Lewis et al. "Efficient Delivery of siRNA for Inhibition of Gene Expression in Postnatal Mice." *Nat. Genet.* 32(2002):107-108.

Li et al. "Delivery of RNA Interference." *Cell Cycle.* 5.18(2006):2103-2109.

Li et al. "Differential Expression and Regulation of IL-23 and IL-12 Subunits and Receptors in Adult Mouse Microglia." *J. Neurol. Sci.* 215.1-2(2003):95-103.

Li et al. "Inhibition of HIV-1 Infection by Lentiviral Vectors Expressing Pol III-Promoted Anti-HIV RNAs." *Mol. Ther.* 8.2(2003):196-206.

Li et al. "Safety and Immunogenicity of the Live Oral Auxotrophic *Shigella flexneri* SFL124 in Adult Vietnamese Volunteers." *Vacc.* 11.2(1993):180-189.

Li et al. "Safety and Immunogenicity of the Live Oral Auxotrophic *Shigella flexneri* SFL124 in Volunteers." *Vacc.* 10.6(1992):395-404.

Libby et al. "A Cytolysin Encoded by *Salmonella* is Required for Survival Within Macrophages." *PNAS.* 91.2(1994):489-493.

Lisser et al. "Compilation of *E. coli* mRNA Promoter Sequences." *Nucl. Acids Res.* 21.7(1993):1507-1516.

Liu et al. "Hydrodynamics-Based Transfection in Animals by Systemic Administration of Plasmid DNA." *Gene Ther.* 6(1999):1258-1266.

Macron. "Cequent Reports Delay in Lead Program, But Unveils New Drug-Development Efforts." *RNAi News.* 6.19(2008):1-13.

Maeda et al. "Evidence for Multiple OmpR-Binding Sites in the Upstream Activation Sequence of the *ompC* Promoter in *Escherichia coli*: A Singple OmpR-Binding Site is Capable of Activating the Promoter." *J. Bacteriol.* 172.1(1990):501-503.

Markowska-Daniel et al. "Adjuvant Properties of Propionibacterium avidum KP-40 in Vaccination Against Endemic Viral and Bacterial Infections." *Zbl. Bakt.* 277(1992):547-553.

Marshall et al. "Gene Therapy Death Prompts Review of Adenovirus Vector." *Science.* 286.5448(1999):2244-2245.

Martin-Orozco et al. "Visualization of Vacuolar Acidification-Induced Transcription of Genes of Pathogens Inside Macrophages." *Mol. Biol. Cell.* 17.1(2006):498-510.

Mastroeni et al. "Role of T Cells, TNFα and IFNγ in Recall of Immunity to Oral Challenge with Virulent Salmonellae in Mice Vaccinated with Live Attenuated *aro*-Salmonella Vaccines." *Microb. Pathog.* 13.6(1992):477-491.

Mathew et al. "Cytosolic Delivery of Antisense Oligonucleotides by Listeriolysin O-Containing Liposomes." *Gene Ther.* 10(2003):1105-1115.

McCaffrey et al. "Gene Expression: RNA Interference in Adult Mice." *Nature.* 418(2002):38-39.

McCaffrey et al. "Inhibition of Hepatitis B Virus in Mice by RNA Interference." *Nat. Biotechnol.* 21.6(2003):639-644.

McFarland et al. "Effect of Different Purine Auxotrophic Mutations on Mouse Virulence of Vi-Positive Strain of *Salmonella dublin* and of Two Strains of *Salmonella typhimurium*." *Microb. Pathogen.* 3(1987):129-141.

Meng et al. "UP Element-Dependent Transcription at the *Escherichia coli rrnB* P1 Promoter: Positional Requirements and Role of the RNA Polymerase α Subunit Linker." *Nucl. Acids Res.* 29.20(2001):4166-4178.

Menguad et al. "Identification of Phosphatidylinositol-Specific Phopholipase C Activity in *Listeria monocytogenes*: A Novel Type of Virulence Factor?" *Mol. Microbiol.* 5.2(1991):367-372.

Meselson et al. "DNA Restriction Enzyme from *E. coli*." *Nature.* 217(1968):1110-1114.

Miliotis. "Acridine Orange Stain for Determining Intracellular Enteropathogens in HeLa Cells." *J. Clin. Microbiol.* 29.4(1991):830-831.

Miller et al. "A Two-Component Regulatory System (*phoP phoQ*) Controls *Salmonella typhimurium* Virulence." *PNAS.* 86.13(1989):5054-5058.

Miller et al. "Constitutive Expression of the PhoP Regulon Attenuates *Salmonella* Virulence and Survival Within Macrophages." *J. Bacteriol.* 172.5(1990):2485-2490.

Milligan et al. "Oligoribonucleotide Synthesis Suing T7 RNA Polymerase and Synthetic DNA Templates." *Nucl. Acids Res.* 15.21(1987):8783-8798.

Milligan et al. "Synthesis of Small RNAs Using T7 RNA Polymerase." *Meth. Enzymol.* 180(1989):51-62.

Minagawa et al. "Indentification and Molecular Characterization of the Mg2+ Stimulon of *Escherichia coli*." *J. Bacteriol.* 185.13(2003):3696-3702.

Mitsuyama et al. "Interleukin-6 Trans-Signaling in Inflammatory Bowel Disease." *Cytokine Growth Factor Rev.* 17.6(2006):451-461.

Miyagishi et al. "Strategies for Generation of an siRNA Expression Library Directed Against the Human Genome." *Oligonucleotides.* 13(2003):325-333.

Mizoguchi. "Chitinase 3-Like-1 Exacerbates Intestinal Inflammation by Enhancing Bacterial Adhesion and Invasion in Colonic Epithelial Cells." *Gastroenterology.* 130(2006):398-411.

Molin et al. "Suicidal Genetic Elements and Their Use in Biological Containment of Bacteria." *Ann. Rev. Microbiol.* 47(1993):139-166.

Morrissey et al. "Activity of Stabilized Short Interfering RNA in a Mouse Model of Hepatitis B Virus Replication." *Hepatol.* 41.6(2005):1349-1356.

(56) References Cited

OTHER PUBLICATIONS

Morrissey et al. "Potent and Persistent in vivo Anti-HBV Activity of Chemically Modified siRNAs." *Nat. Biotechnol.* 23.8(2005):1002-1007.
Neidhardt et al. "Positive Regulatory Gene for Temperature-Controlled Proteins in *Escherichia coli.*" *Biochem. Biophys. Res. Comm.* 100.2(1981):894-900.
Neidhardt et al. "The Genetics and Regulations of Heat-Shock Proteins." *Ann. Rev. Genet.* 18(1984):295-329.
Nguyen et al. "Bacterial Vectors for RNAi Delivery." *Pathobiotech.* Austin, TX: Landes Bioscience. Sleater, ed. Chapter 9(2008):121-125.
Nguyen et al. "RNAi Therapeutics: An Update on Delivery." *Curr. Opin. Mol. Ther.* 10.2(2008):158-167.
Nicholson. "Function, Mechanism and Regulation of Bacterial Ribonucleases." *FEMS Microbiol Rev.* 23.3(1999):371-390.
Nnalue et al. "Test of the Virulence and Live-Vaccine Efficacy of Auxotrophic and galE Derivatives of *Salmonella chloeraesuis.*" *Infect. Immun.* 55.4(1987):955-962.
Noriega et al. "Construction and Characterization of Attenuated $\Delta$aroA $\Delta$virG *Shigella flexneri* 2a Straing CVD 1023, a Prototype Live Oral Vaccine." *Infect. Immun.* 62.11(1994):5168-5172.
Noriega et al. "Engineered $\Delta$guaB-A $\Delta$virG *Shigella flexneri* 2a strain CVD 1205: Construction, Safety, Immunogenicity, and Potential Efficacy as Mucosal Vaccine." *Infect. Immun.* 64.8(1994):3055-3061.
Noriega et al. "Further Characterization of $\Delta$aroA $\Delta$virG *Shigella flexneri* 2a Strain CVD 1203 as a Mucosal *Shigella* Vaccine and as a Live-Vector Vaccine for Delivering Antigens of Enterotoxigenic *Escherichia coli.*" *Infect. Immun.* 64.1(1996):23-27.
Normanly et al. "Changing the Identity of a Transfer RNA." *Nature.* 321.6067(1986):213-219.
O'Gaora et al. "*Yersinia enterocolitica aroA* Mutants as Carriers of the B Subunit of the *Escherichia coli* Heat-Labile Enterotoxin to the Murine Immune System." *Microbial. Pathog.*9.2(1990):105-116.
Ocker et al. "Variants of bcl-2 Specific siRNA for Silencing Antiapoptotic bcl-2 in Pancreatic Cancer." *Gut.* 54(2005):1298-1308.
Ortega-Barria et al. "A Novel T. cruzi Heparin-Binding Protein Promotes Fibroblast Adhesion and Penetration of Engineered Bacteria and Trypanosomes into Mammalian Cells." *Cell.* 67.2(1981):411-421.
Oshima et al. "Transciptome Analysis of All Two-Component Regulatory System Mutants of *Escherichia coli* K-12." *Mol. Microbiol.* 46.1(2002):281-291.
Ott. "Genetic Approaches to Study *Legionella pneumophila* Pathogenicity." *FEMS Micro. Rev.* 14(1994):161-176.
Paddison et al. "Short Hairpin RNAs (shRNAs) Induce Sequence-Specific Silencing in Mammalian Cells." *Genes Dev.* 16(2002):948-958.
Paddison et al. "Stable Suppression of Gene Expression by RNAi in Mammalian Cells." *PNAS.* 99.3(2002):1443-1448.
Palffy et al. "Bacteria in Gene Therapy: Bactofection Versus Alternative Gene Therapy." *Gene Ther.* 13.2(2006):101-105.
Palliser et al. "An siRNA-Based Microbicide Protects Mice from Lethal Herpes Simplex Virus 2 Infection." *Nature.* 439(2006):89-94.
Park et al. "*Salmonella typhimurium* Mutants Lacking NAD Pyrophosphatase." *J. Bacteriol.* 170.8(1988):3725-3730.
Pascual et al. "The Enteric Nervous and Immune Systems: Interactions for Mucosal Immunity and Inflammation." *ImmunoMeth.* 5.1(1994):56-72.
Pawelek et al. "Bacteria as Tumour-Targeting Vectors." *Lancet Oncol.* 4(2003):548-556.
Pawelek et al. "Tumor-Targeted *Salmonella* as a Novel Anticancer Vector." *Cancer Res.* 57(1997):4537-4544.
Peer et al. "Selective Gene Silencing in Activated Leukocytes by Targeting siRNAs to the Integrin Lumphocyte Function-Associated Antigen-1." PNAS. 104.10(2007):4095-4100.
Peer et al. "Systemic Leukocyte-Directed siRNA Delivery Revealing Cyclin D1 as an Anti-Inflammatory Target." *Science.* 319.5863(2008):627-630.
Pertzev et al. "Characterization of RNA Sequence Determinants and Antideterminants of Processing Reactivity for a Minimal Substrate of *Escherichia coli* Ribonuclease III." *Nucl. Acids Res.* 34.13(2006):3708-3721.
Pilgrim et al. "Bactofection of Mammalian Cells by Listeria monocytes: Improvement and Mechanism of DNA Delivery." *Gene Ther.* 10(2003):2036-2045.
Plank et al. "The Influence of Endosome-Disruptive Peptides on Gene Transer Using Synthetic Virus-Like Gene Transfer Systems." *J. Biol. Chem.* 269.17(1994):12918-12924.
Putral et al. "RNA Interference Against Human Papillomavirus Oncogenes in Cervical Cancer Cells Results in Increased Sensitivity to Cisplatin." *Mol. Pharmacol.* 68.5(2005):1311-1319.
Quandt et al. "Versatile Suicide Vectors Which Allow Direct Selection for Gene Replacement in Gram-Negative Bacteria." *Gene.* 127.1(1993):15-21.
Raetz. "Bacterial Lipopolysaccharides: A Remarkable Family of Bioactive Macroamphiphiles." *Escherichia coli and Salmonella.* 1(1996):1035-1063.
Reader et al. "Lysis Defective Mutants of Bacteriophage Lambda: On the Role of the S Function in Lysis." *Virol.*43.3(1971):623-637.
Recorbet et al. "Conditional Suicide System of *Escherichia coli* Released Into Soil That Uses the *Bacillus subtilis sacB* Gene." *Appl. Envir. Microbiol.* 59.5(1993):1361-1366.
Rembacken et al. "Non-Pathogenic *Escherichia coli* Versus Mesalazine for the Treatment of Ulcerative Colitis: A Randomised Trial." *Lancet.* 354.9179(1999):635-639.
Rennell et al. "Phage P22 Lysis Genes: Nucleotide Sequences and Functional Relationships with T4 and $\lambda$ Genes." *Virol.* 143.1(1985):280-289.
Rodionov et al. "Regulation of Lysine Biosynthesis and Transport Genes in Bacteria: Yet Another RNA Riboswitch?" *Nucl. Acids Res.* 31.23(2003):6748-6757.
Rosenkranz et al. "Receptor-Mediated Endocytosis and Nuclear Transport of a Transfecting DNA Construct." *Exp. Cell Res.* 199.2(1992):323-329.
Roy et al. "A Process for Controlling Intracellular Bacterial Infections Induced by Membrane Injury." *Science.* 304(2004):1515-1518.
Russmann. "Bacterial Type III Translocation: A Unique Mechanism for Cytosolic Display of Heterologous Antigens by Attenuated Salmonella." *Int. J. Med. Microbiol.* 293(2003):107-112.
Sansonetti et al. "Construction and Evaluation of a Double Mutant of *Shigella flexneri* as a Candidate for Oral Vaccination Against Shigellosis." *Vacc.* 7.5(1989):443-450.
Sansonetti et al. "*Omp*B (osmo-regulation) and *ics*A (Cell-to-Cell Spread) Mutants of *Shigella flexneri*: Vaccine Candidates and Probes to Study the Pathogenesis of Shigellosis." *Vacc.* 9.6(1991):416-422.
Sansonetti et al. "Plasmid-Mediated Invasiveness of "Shigella-like" *Eshrichia coli.*" *Ann. Microbiol. (Inst. Pasteur).* 132A(1982):351-355.
Santel et al. "A Novel siRNA-Lipoplex Technology for RNA Interference in the Mouse Vascular Endothelium." *Gene Ther.* 13(2006):1222-1234.
Santel et al. "RNA Interference in the Mouse Vascular Endothelium by Systemic Administration of siRNA-Lipoplexes for Cancer Therapy." *Gene Ther.* 13(2006):1360-1370.
Schoen et al. "Bacterial Delivery of Functional Messenger RNA to Mammalian Cells." *Cell. Microbiol.* 7.5(2005):709-724.
Seputiene et al. "Transcriptional Analysis of the Acid-Inducible *asr* Gene in Enterobacteria." *Res. Microbiol.* 155.7(2004):535-542.
Check et al. "RNA to the Rescue?" *Nature.* 425(2003):10-12.
Shulzaberger et al. "Anatomy of Escherichia coli $\sigma$70 Promoters." *Nucl. Acids Res.* 35.3(2008):771-788.
Sivakumar et al. "Interleukin 18 is a Primary Mediator of the Inflammation Associated with Dextran Sulphate Sodium Induced Colitis: Blocking Interleukin 18 Attenuates Intestinal Damage." *Gut.* 50.6(2002):812-820.
Sizemore et al. "Attenuated *Shigella* as a DNA Delivery Vehicle for DNA-Mediated Immunization." *Science.* 270(1995):299-302.

(56) References Cited

OTHER PUBLICATIONS

Small et al. "Acid and Base Resistance in *Escherichia coli* and *Shigelle flexneri*: Role of *rpoS* and Growth pH." *J. Bacteriol.* 176.6(1994):1729-1737.
Small et al. "Development of a DNA Probe for the Virulence Plasmid of *Shigella* spp. And Enteroinvasive *Escherichia coli.*" *Microbiology.* Washington, D.C.: American Society for Microbiology. (1986):121-124.
Soncini et al. "Two-Component Regulatory Systems Can Interact to Process Multiple Environmental Signals." *J. Bacteriol.* 178.23(1996):6796-6801.
Song et al. "Antibody Mediated in vivo Delivery of Small Interfering RNAs via Cell-Surface Receptors." *Nat. Biotech.* 23.6(2005):709-717.
Song et al. "RNA Interference Targeting Fas Protects Mice from Fulminant Hepatitis." *Nat. Med.* 9.3(2003):347-351.
Sorensen et al. "Gene Silencing by Systemic Delivery of Synthetic siRNAs in Adult Mice." *J. Mol. Biol.* 327(2003):761-766.
Soutschek et al. "Therapeutic Silencing of an Endogenous Gene by Systemic Administration of Modified si RNAS." *Nature.* 432(2004):173-178.
Spankuch et al. "Cancer Inhibition in Nude Mice after Systemic Application of U6 Promoter-Drien Short Hairpin RNAs Against PLK1." *J. Natl. Cancer Inst.* 96.11(2004):862-872.
Srividkya et al. "Sub Classification and Targeted Characterization of Prophage-Encoded Two-Component Cell Lysis Cassette." *J. Biosci.* 32.5(2007):979-990.
Staudinger et al. "mRNA Expression Profiles for *Escherichia coli* Ingested by Normal and Phagocyte Oxidase-Deficient Human Neutrophils." *J. Clin. Invest.* 110.8(2002):1151-1163.
Stauffer et al. "Characterization of the *gcv* Control Region from *Escherichia coli.*" J. Bacteriol. 176.20(1994):6159-6164.
Stover et al. "New Use of BCG for Recombinant Vaccines." *Nature.* 351(1991):456-460.
Sudarsan et al. "An mRNA Structure in Bacteria that Controls Gene Expression by Binding Lysine." *Genes Dev.* 17.21(2003):2688-2697.
Sudarsan et al. "Thiamine Pyrophosphate Riboswitches Are Targets for the Antimicrobial Compound Pyrithiamine." *Chem. & Biol.* 12.12(2005):1325-1335.
Suziedeliene et al. "The Acid-Inducible *asr* Gene in *Escherichia coli*: Transcriptional Control by the *phoBR* Operon." *J. Bacteriol.* 181.7(1999):2084-2093.
Targan et al. "Defects in Mucosal Immunity Leading to Ulcerative Colitis." *Immunol. Rev.* 206(2005):296-305.
Taylor et al. "Development of a Live, Oral, Attenuated Vaccine Against El Tor Cholera." *J. Infect. Dis.* 170.6(1994):1518-1523.
Taylor et al. "Identification of OmpR: a Positive Regulatory Protein Controlling Expression of the Major Outer Membrane Matrix Porin Proteins of *Escherichia coli* K-12." *J. Bacteriol.* 147.1(1981):255-258.
Taylor et al. "Mutations that Define the Promoter of *ompF*, a Gene Specifying a Major Outer Membrane Porin Protein." *J. Bacteriol.* 162.3(1985):1054-1060.
Ten Hove et al. "Blockade of Endogenous IL-18 Ameliorates TNBS-Induced Colitis by Decreasing Local TNF-α Production in Mice." *Gastroenterology.* 121.6(2001):1372-1379.
Teramoto et al. "Increased Lymphocyte Trafficking to Colonic Microvessels is Dependent on MAdCAM-1 and C-C Chemokine mLARC/CCL20 in DSS-Induced Mice Colitis." *Clin. Ex. Immunol.* 139(2005):421-428.
Thouvenot et al. "The Strong Efficiency of the *Escherichia coli gapA* P1 Promoter Depends on a Complex Combination of Functional Determinants." *Biochem. J.* 383.2(2004):371-382.
Timmons et al. "Ingestion of Bacterially Expressed dsRNAs can Produce Specific and Potent Genetic Interference in *Caenorhabditis elegans*." Gene. 263(2001):103-112.
Timmons et al. "Specific Interference by Ingested dsRNA." *Nature.* 395(1998):8954.

Tominaga. "Characterization of Six Flagellin Genes in the H3, H53, and H54 Standard Strains in *Escherichia coli.*" *Genes Genet. Syst.* 79.1(2004):1-8.
Toso et al. "Phase I Study of the Intravenous Administration of Attenuated *Salmonella typhimurium* to Patients with Metastatic Melanoma." *J. Clin. Oncol.* 20.1(2002):142-152.
Vassaux et al. "Bacterial Gene Therapy Strategies." *J. Pathol.* 208(2006):290-298.
Vaughn et al. "An Aromatic-Dependent Mutant of the Fish Pathogen *Aeromonas salmonicida* Is Attenuated in Fish and Is Effective as a Live Vaccine Against the Salmonid Disease Furunculosis." *Infect. Immun.* 61.5(1993):2172-2181.
Verma et al. "Construction of Aromatic Dependent *Shigella flexneri* 2a Live Vaccine Candidate Strains: Deletion Mutations in the *aroA* and the *aroD* Genes." *Vacc.* 9.1(1991):6-9.
Waldor et al. "Emergence of a New Cholera Pandemic: Molecular Analysis of Virulence Determinants in *Vibrio cholerae* 0139 and Development of a Live Vaccine Prototype." *J. Infect. Dis.* 170.2(1994):278-283.
Watanabe et al. "Interleukin 7 Transgenic Mice Develop Chronic Colitis with Decreased Interleukin 7 Protein Accumulation in the Colonic Mucosa." *J. Exp. Med.* 187.3(1998):389-402.
Watarai et al. "Comparison of Etiological and Immunological Characteristics of Two Attenuated *Erysipelothrix rhusiopathiae* Strains of Serotypes 1a and 2." *J. Vet. Med. Sci.* 55.4(1993):595-600.
Weber et al. "Claudin-1 and Claudin-2 Expression is Elevated in Inflammatory Bowel Disease and May Contribute to Early Neoplastic Transformation." *Lab. Invest.* 88.10(2008):1110-1120.
Weckman et al. "Critical Link Between Trail and CCL20 for the Activation of TH2 Cells and the Expression of Allergic Airway Disease." *Nature Med.* 13.11(2007):1308-1315.
Weiss et al. "Transfer of Eukaryotic Expression Plasmids to Mammalian Host Cells by Bacterial Carriers." *Curr. Opin. Biotechnol.* 12(2001):467-472.
Welkos et al. "Non-Toxigenic Derivatives of the Ames Strain of *Bacillus anthracis* are Fully Virulent for Mice: Role of Plasmid pX02 and Chromosome in Strain-Dependent Virulence." *Microb. Pathol.* 14.5(1993):381-388.
Winkler et al. "Thiamine Derivatives Bind Messenger RNAs Directly to Regulate Bacterial Gene Expression." *Nature.* 419.6910(2002):952-956.
Wu et al. "Receptor-Mediated Gene Delivery and Expression in Vivo." *J. Biol. Chem.* 263.29(1988):14621-14624.
Wurtzel et al. "Osmoregulation of Gene Expression." *J. Biol. Chem.* 257.22(1982):13685-13691.
Wösten et al. "A Signal Transduction System that Responds to Extracellular Iron." *Cell.* 103.1(2000):113-125.
Xia et al. "siRNA-Mediated Gene Silencing in vitro and in vivo." *Nat. Biotechnol.* 20(2002):1006-1010.
Xiang et al. "Short Hairpin RNA-Expressing Bacteria Elicit RNA Interference in Mammals." *Nat. Biotechnol.* 24.6(2006):697-702.
Yamazaki et al. "Mucosal T Cells Expressing High Levels of IL-7 Receptor are Potential Targets for Treatment of Chronic Colitis." *J. Immunol.* 171.3(2003):1556-1563.
Young et al. "The Invasion Protein of *Yersinia enterocolitica*: Internalization of Invasin-Bearing Bacteria by Eukaryotic Cells is Associate with Reorganization of the Cytoskeleton." *J. Cell. Biol.* 116.1(1992):197-207.
Young. "Bacterial Lysis: Mechanism and Regulation." *Microbiol. Rev.* 56.3(1992):430-481.
Young. "Transcription Termination in the *Escherichia coli* Ribosomal Rna Operon *rrnC.*" *J. Biol. Chem.* 264.24(1979):12725-12731.
Yu et al. "RNA Interference by Expression of Short-Interfering RNAs and Hairpin RNAs in Mammalian Cells." *PNAS.* 99.9(2002):6047-6052.
Zamore et al. "siRNAs Knock Down Hepatitis." *Nat. Med.* 9.3(2003):266-267.

(56) References Cited

OTHER PUBLICATIONS

Zeissig et al. "Changes in Expression and Distribution of Claudin 2, 5 and 8 Lead to Discontinuous Tight Junctions and Barrier Dysfunction in Active Crohn's Disease." *Gut.* 56.1(2007):61-72.

Zhang et al. "Engineering Mucosal RNA Interference in Vivo." *Molecular Ther.* 14.3(2006):336-342.

Zhang et al. "Hydroporation as the Mechanism of Hydrodynamic Delivery." *Gene Ther.* 11(2004):675-682.

Zhang et al. "Intratumoral Delivery and Suppression of Prostate Tumor Growth by Attenuated *Salmonella enterica* serovar *typhimurium* Carrying Plasmid-Based Small Interfering RNAs." *Cancer Res.* 67.12(2007):5859-5864.

Zhang et al. "Regulation of Ribonuclease III Processing by Double-Helical Sequence Antideterminants." *PNAS.* 94.25(1997):13437-13441.

Zhao et al. "High-Throughput Screening of Effective siRNAs from RNAi Libraries Delivered via Bacterial Invasion." *Nat. Meth.* 2.12(2005):967-973.

Zhao et al. "Tumor-Targeting Bacterial Therapy with Amino Acid Auxotrophs of GFP-Expressing *Salmonella typhimurium*." *PNAS.* 102.3(2005):755-760.

Zimmermann et al. "RNAi-Mediated Gene Silencing in Non-Human Primates." *Nature.* 441(2006):111-114.

Zwir et al. "Dissecting the PhoP Regulatory Network of *Escherichia coli* and *Salmonella enterica*." *PNAS.* 102.8(2005):2862-2867.

Zychlinsky et al. "IpaB Mediates Macrophage Apoptosis Induced by *Shigella flexneri*." *Mol. Microbiol.* 11.4(1994):619-627.

McGhee et al. "The Common Mucosal Immune System: From Basic Principles to Enteric Vaccines With Relevance for the Female Reproductive Tract." *Reprod. Fertil. Dev.* 6.3(1994):369-379.

Thompson et al. "Antisense Inhibitors, Ribozymes, and siRNAs." *Clin. Liver Dis.* 13(2009):375-390.

COMPOSITIONS FOR BACTERIAL MEDIATED GENE SILENCING AND METHODS OF USING SAME

CROSS REFERENCE TO RELATED APPLICATIONS

This application is continuation application of U.S. Ser. No. 11/793,429, filed Nov. 20, 2007, which is a 35 U.S.C. §371 National Phase Application of PCT/US2005/045513, filed Dec. 16, 2005; which claims the benefit of, and priority to, U.S. Ser. No. 60/637,277 filed Dec. 17, 2004 and U.S. Ser. No. 60/651,238 filed Feb. 8, 2005, each of which is incorporated by reference in its entirety.

INCORPORATION-BY-REFERENCE OF SEQUENCE LISTING

The contents of the text file named "29627_501C01US_SeqListing_ST25.txt", which was created on Dec. 16, 2011, and is 2.48 KB in size, are hereby incorporated by reference in their entirety.

BACKGROUND

Gene silencing through RNAi (RNA-interference) by use of short interfering RNA (siRNA) has emerged as a powerful tool for molecular biology and holds the potential to be used for therapeutic gene silencing. Short hairpin RNA (shRNA) transcribed from small DNA plasmids within the target cell has also been shown to mediate stable gene silencing and achieve gene knockdown at levels comparable to those obtained by transfection with chemically synthesized siRNA (T. R. Brummelkamp, R. Bernards, R. Agami, *Science* 296, 550 (2002), P. J. Paddison, A. A. Caudiy, G. J. Hannon, *PNAS* 99, 1443 (2002)).

Possible applications of RNAi for therapeutic purposes are extensive and include silencing and knockdown of disease genes such as oncogenes or viral genes. One major obstacle for the therapeutic use of RNAi is the delivery of siRNA to the target cell (Zamore P D, Aronin N. *Nature Medicine* 9, (3): 266-8 (2003)). In fact, delivery has been described as the major hurdle now for RNAi (Phillip Sharp, cited by Nature news feature, Vol 425, 2003, 10-12)

Two methods have been described which can be used in mouse models:

(1) Direct hydrodynamic intravenous injection of siRNA or shRNA-encoding plasmids: using this method, several authors have described application of RNAi against various conditions, e.g. hepatitis B (A. P. McCaffrey et al., Nat. Biotechnol. 2003 June; 21(6):639-44), fulminant hepatitis (E. Song, S. K. Lee, J. Wang, N. Ince, J. MM, J. Chen, P. Shankar, J. Lieberman. *Nature Medicine* 9, 347 (2003)), tumor xenograft (Spaenkuch B, et al. *JNCI,* 96(1): 862-72 (2004)), hepatic transgene expression (D. L. Lewis, J. E. Hagstrom, A. G. Loomis, J. A. Wolff, H. Hereijer, *Nature Genetics,* 32, 107 (2002), D. R. Sorensen D R, M. Leirdal, M. Sioud, *JMB,* 327, 761 (2003)). This method uses a high pressure and high volume injection (2.5 ml) into the mouse tail vein. The mechanism of siRNA/DNA uptake into the cells is not clear but probably mechanical damage to the vascular endothelial layer is involved. A clear disadvantage of this method is that this is not a method which could be developed into human application as it involves a massive volume charge and completely unknown mechanism of action.

(2) Direct injection into the target tissue (brain) of an siRNA encoding adenoviral vector (H. Xia, Q. Mao, H. L. Paulson, B. L. Davidson, *Nat Biotechnol,* 20, 1006 (2002)). This method showed silencing of transgene (GFP) expression in the brain tissues reached by the adenoviral vector. However, the area of silencing could not be predicted reliably. This method might be developed further and might become applicable for local, e.g. intratumoral injection. Viral vectors have been used widely for gene therapy purposes, but one lesson learned from gene therapy experiments is that viral spreading can be unpredictable at times and lead to unwanted side effects (Marshall E. *Science* 286(5448): 2244-5 (1999)). A new method is needed for the safe and predictable administration of interfering RNAs to mammals.

SUMMARY OF THE INVENTION

The invention generally pertains to methods of delivering one or more siRNAs to a eukaryotic cell by introducing a bacterium to the cell, wherein the bacterium contains one or more siRNAs or one or more DNA molecules encoding one or more siRNAs.

In one embodiment of this method, the eukaryotic cell is in vivo. In another embodiment of this invention, the eukaryotic cell is in vitro.

The invention also pertains to a method of regulating gene expression in a eukaryotic cell, by introducing a bacterium to the cell, wherein the bacterium contains one or more siRNAs or one or more DNA molecules encoding one or more siRNAs, wherein the expressed siRNAs interfere with the mRNA of the gene to be regulated, thereby regulating expression of the gene.

In one embodiment of this method, the expressed siRNAs direct the multienzyme complex RISC(RNA-induced silencing complex) of the cell to interact with the mRNA to be regulated. This complex degrades the mRNA. This causes the expression of the gene to be decreased or inhibited. In another embodiment of this method, the gene is ras or β-catenin. In one aspect of this embodiment, the ras is k-Ras.

In one embodiment of the above methods of the invention, the eukaryotic cell is a mammalian cell. In one aspect of this embodiment, the mammalian cell is a human cell.

The invention also pertains to a method of treating or preventing cancer or a cell proliferation disorder in a mammal, by regulating the expression of a gene or several genes in a cell known to increase cell proliferation by introducing a bacterium to the cell. The bacterium contains one or more siRNAs or one or more DNA molecules encoding one or more siRNAs.

In one embodiment of this method of the invention, the mammal is a human. In another embodiment of this method the expressed siRNAs interfere with the mRNA of the gene to be regulated. In one aspect of this embodiment, the expressed siRNAs direct the multienzyme complex RISC(RNA-induced silencing complex) of the cell to interact with the mRNA to be regulated. This complex degrades the mRNA. This causes the expression of the gene to be decreased or inhibited.

In another embodiment of this method, the gene is ras or β-catenin. In one aspect of this embodiment, the ras is k-Ras.

In another embodiment of this method of the invention, the cell is a colon cancer cell or a pancreatic cancer cell. In one aspect of this embodiment, the colon cancer cell is an SW 480 cell. In another aspect of this embodiment, the pancreatic cancer cell is a CAPAN-1 cell.

In one embodiment of the above methods of the invention, the bacterium is non-pathogenic or non-virulent. In another aspect of this embodiment, the bacterium is therapeutic. In another aspect of this embodiment, the bacterium is an attenuated strain selected from the group consisting of *Listeria, Shigella, Salmonella, E. coli,* and Bifidobacteriae. Optionally, the *Salmonella* strain is an attenuated strain of the *Salmonella typhimurium* species. Optionally, the *Salmonella typhimurium* strain is SL 7207 or VNP20009. Optionally, the *E. coli* strain is BM 2710.

In another embodiment of the above methods of the invention, the one or more DNA molecules encoding the one or more siRNAs are transcribed within the eukaryotic cell. In one aspect of this embodiment, the one or more siRNAs are transcribed within the eukaryotic cells as shRNAs. In another aspect of this embodiment, the one or more DNA molecules encoding the one or more siRNAs contains an RNA-polymerase III promoter. Optionally, the RNA polymerase III promoter is a U6 promoter or an H1 promoter.

In another embodiment of the above methods of the invention, the one or more DNA molecules encoding one or more siRNAs are transcribed within the bacterium. In one aspect of this embodiment, the one or more DNA molecules contain a prokaryotic promoter. Optionally, the prokaryotic promoter is a T7 promoter.

In another embodiment of the above methods of the invention, the one or more DNA molecules are introduced to the eukaryotic cell through type III export or bacterial lysis. In one aspect of this embodiment, the bacterial lysis is triggered by the addition of an intracellular active antibiotic. Optionally, the antibiotic is tetracycline. In another aspect of this embodiment, the bacterial lysis is triggered through bacterial metabolic attenuation. Optionally, the metabolic attenuation is auxotrophy.

The invention also pertains to a bacterium containing one or more siRNAs or one or more DNA molecules encoding one or more siRNAs.

In one embodiment of this invention, the bacterium is a non-pathogenic or a non-virulent bacterium. In another aspect of this embodiment, the bacterium is a therapeutic bacterium.

In another embodiment of this invention, the bacterium is an attenuated strain selected from a member of the group consisting of *Listeria, Shigella, Salmonella, E. coli,* and Bifidobacteriae. Optionally, the *Salmonella* strain is an attenuated strain of the *Salmonella typhimurium* species. Optionally, the *Salmonella typhimurium* strain is SL 7207 or VNP20009. Optionally, the *E. coli* strain is BM 2710.

The invention also pertains to a prokaryotic vector containing a DNA encoding one or more siRNAs and an RNA-polymerase III compatible promoter or a prokaryotic promoter.

In one embodiment of this vector of the invention, the RNA polymerase III promoter is a U6 promoter or an H1 promoter. In another embodiment of this vector of the invention, the prokaryotic promoter is a T7 promoter.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference. In the case of conflict, the present specification, including definitions, will control. In addition, the materials, methods, and examples are illustrative only and are not intended to be limiting.

Other features and advantages of the invention will be apparent from the following detailed description and claims.

DETAILED DESCRIPTION OF THE INVENTION

Figure 1A:
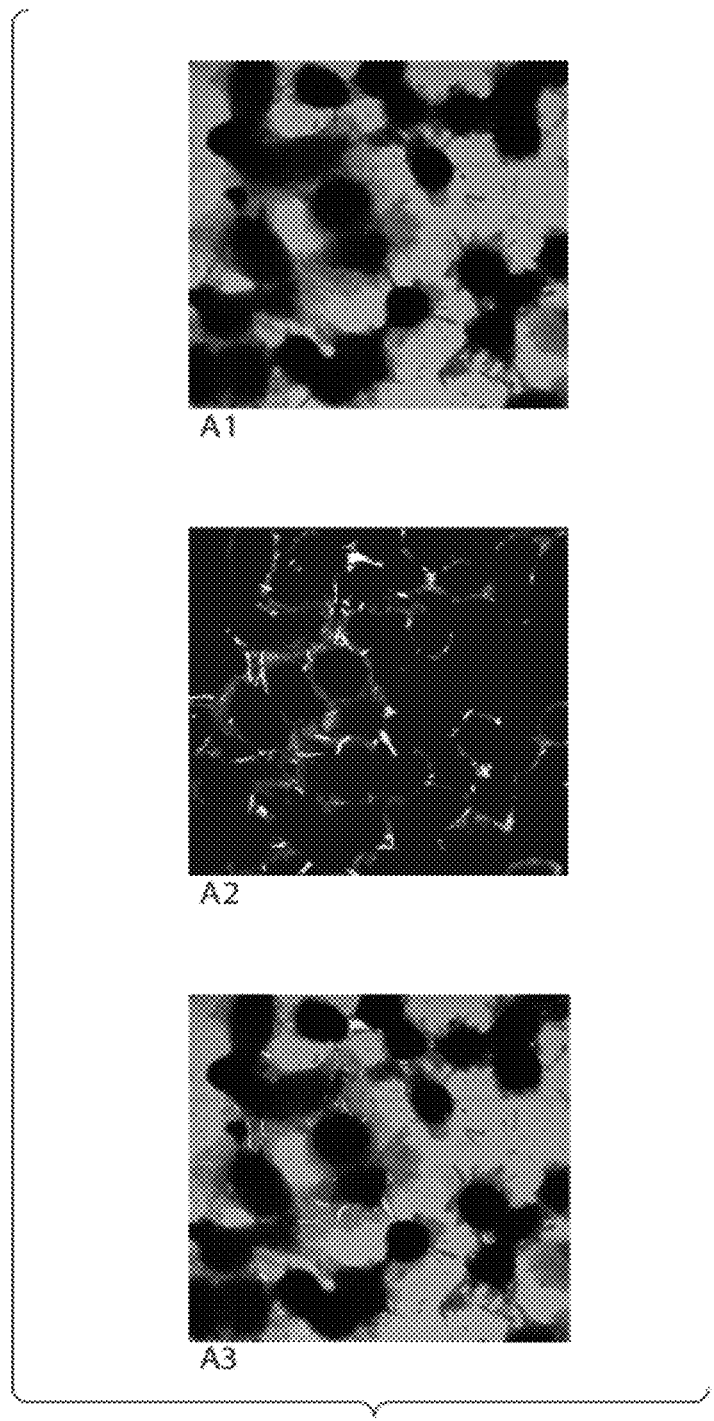
FIG. 1A shows micrographs of invasion of SL 7207 into SW 480 cells.

The invention pertains to methods of delivering small interfering RNAs (siRNAs) to eukaryotic cells using non-pathogenic or therapeutic strains of bacteria. The bacteria deliver RNA encoding DNA or RNA, itself, to effect RNA interference (RNAi). The interfering RNA of the invention regulates gene expression in eukaryotic cells. It silences or knocks down genes of interest inside target cells. The interfering RNA directs the cell-owned multienzyme-complex RISC (RNA-induced silencing complex) to the mRNA of the gene to be silenced. Interaction of RISC and mRNA results in degradation of the mRNA. This leads to effective post-transcriptional silencing of the gene of interest. This method is referred to as Bacteria Mediated Gene Silencing (BMGS).

Bacterial delivery is more attractive than viral delivery as it can be controlled by use of antibiotics and attenuated bacterial strains which are unable to multiply. Also, bacteria are much more accessible to genetic manipulation which allows the production of vector strains specifically tailored to certain applications. In one embodiment of the invention, the methods of the invention are used to create bacteria which cause RNAi in a tissue specific manner.

The siRNA is either introduced into the target cell directly or by transfection or can be transcribed within the target cell as hairpin-structured dsRNA (shRNA) from specific plasmids with RNA-polymerase III compatible promoters (U6, H1) (P. J. Paddison, A. A. Caudiy, G. J. Hannon, *PNAS* 99, 1443 (2002), T. R. Brummelkamp, R. Bernards, R. Agami, *Science* 296, 550 (2002)).

Liberation of siRNA encoding plasmid from the intracellular bacteria occurs through active mechanisms. One mechanism involves the type III export system in *S. typhimuriumm*, a specialised multiprotein complex spanning the bacterial cell membrane whose functions include secretion of virulence factors to the outside of the cell to allow signaling towards the target cell, but which can also be used to deliver antigens into target cells. (Rüssmann H. *Int J Med Microbiol*, 293:107-12 (2003)) or through bacterial lysis and liberation of bacterial contents into the cytoplasm. The lysis of intracellular bacteria is triggered through addition of an intracellularly active antibiotic (tetracycline) or occurs naturally through bacterial metabolic attenuation (auxotrophy). After liberation of the eukaryotic transcription plasmid, shRNA or siRNA are produced within the target cell and trigger the highly specific process of mRNA degradation, which results in silencing of the targeted gene.

The non-virulent bacteria of the invention have invasive properties and may enter a mammalian host cell through various mechanisms. In contrast to uptake of bacteria by professional phagocytes, which normally results in the destruction of the bacterium within a specialized lysosome, invasive bacteria strains have the ability to invade non-phagocytic host cells. Naturally occurring examples of such bacteria are intracellular pathogens such as *Listeria, Shigella* and *Salmonella*, but this property can also be transferred to other bacteria such as *E. coli* and Bifidobacteriae, including probiotics through transfer of invasion-related genes (P. Courvalin, S. Goussard, C. Grillot-Courvalin, *C.R. Acad. Sci. Paris* 318, 1207 (1995)). In other embodiments of the invention, bacteria used to deliver interfering RNAs to host cells include *Shigella flexneri* (D. R. Sizemore, A. A. Branstrom, J. C. Sadoff, *Science* 270, 299 (1995)), invasive *E. coli* (P. Courvalin, S. Goussard, C. Grillot-Courvalin, *C.R. Acad. Sci. Paris* 318, 1207 (1995), C. Grillot-Courvalin, S. Goussard, F. Huetz, D. M. Ojcius, P. Courvalin, *Nat Biotechnol* 16, 862 (1998)), *Yersinia enterocolitica* (A. Al-Mariri A, A. Tibor, P. Lestrate, P. Mertens, X. De Bolle, J. J. Letesson *Infect Immun* 70, 1915 (2002)) and *Listeria monocytogenes* (M. Hense, E. Domann, S. Krusch, P. Wachholz, K. E. Dittmar, M. Rohde, J. Wehland, T. Chakraborty, S. Weiss, *Cell Microbiol* 3, 599 (2001), S. Pilgrim, J. Stritzker, C. Schoen, A. Kolb-Maurer, G. Geginat, M. J. Loessner, I. Gentschev, W. Goebel, *Gene Therapy* 10, 2036 (2003)). Any invasive bacterium is useful for DNA transfer into eukaryotic cells (S. Weiss, T. Chakraborty, *Curr Opinion Biotechnol* 12, 467 (2001)).

BMGS is performed using the naturally invasive pathogen *Salmonella typhimurium*. In one aspect of this embodiment, the strains of *Salmonella typhimurium* include SL 7207 and VNP20009 (S. K. Hoiseth, B. A. D. Stocker, *Nature* 291, 238 (1981); Pawelek J M, Low K B, Bermudes D. *Cancer Res.* 57(20):4537-44 (Oct. 15 1997)). In another embodiment of the invention, BMGS is performed using attenuated *E. coli*. In one aspect of this embodiment, the strain of *E. coli* is BM 2710 (C. Grillot-Courvalin, S. Goussard, F. Huetz, D. M. Ojcius, P. Courvalin, *Nat Biotechnol* 16, 862 (1998)). In another aspect of this embodiment, the BM 2710 strain is engineered to possess cell-invading properties through an invasion plasmid. In one aspect of the invention, this plasmid is pGB2inv-hly.

A double "trojan horse" technique is also used with an invasive and auxotrophic bacterium carrying a eukaryotic transcription plasmid. This plasmid is, in turn, transcribed by the target cell to form a hairpin RNA structure that triggers the intracellular process of RNAi. This method of the invention induces significant gene silencing of a variety of genes. In certain aspects of this embodiment, the genes include a transgene (GFP), a mutated oncogene (k-Ras) and a cancer related gene (β-catenin) in vitro.

The invention also pertains to a variation of the described method, termed Bacteria Transcribed Gene Silencing (BTGS). In this aspect of the invention, siRNA is directly produced by the invasive bacteria as opposed to the target cell. A transcription plasmid controlled by a prokaryotic promoter (e.g. T7) is inserted into the carrier bacteria through standard transformation protocols. siRNA is produced within the bacteria and is liberated within the mammalian target cell after bacterial lysis triggered either by auxotrophy or by timed addition of antibiotics.

The RNAi methods of the invention, including BMGS and BTGS are used as a cancer therapy or to prevent cancer. This method is effected by silencing or knocking down genes involved with cell proliferation or other cancer phenotypes. Examples of these genes are k-Ras and β-catenin. Specifically, k-Ras and β-catenin are targets for RNAi based therapy of colon cancer. These oncogenes are active and relevant in the majority of clinical cases. BMGS is applied to reach the intestinal tract for colon cancer treatment and prevention. These methods are also used to treat of animals carrying xenograft tumors, to treat and prevent cancer in k-Ras V12 model of intestinal tumorgenesis, and to prevent and treat tumors in the adenomatous polyposis coli min mouse model (APC-min model) In this model, the mouse has a defective APC gene resulting in the formation of numerous intestinal and colonic polyps which is used as an animal model for human familiar adenomatous polyposis coli (FAP) of intestinal tumorigenesis.

The invention also encompasses a prokaryotic shRNA-encoding transcription plasmid for use with invasive bacteria to perform Bacteria-Transcribed Gene Silencing (BTGS). These plasmids are used to screen different cancer-related targets in transgenic as well as wild type animals for therapeutic experiments.

The RNAi methods of the invention, including BMGS and BTGS are also used to treat or prevent viral diseases (e.g. hepatitis) and genetic disorders.

The RNAi methods of the invention, including BMGS and BTGS are also used to create cancer-preventing "probiotic bacteria" for use, especially with the target of GI tract or liver.

The RNAi methods of the invention, including BMGS and BTGS are used as therapy against inflammatory conditions, e.g. hepatitis, inflammatory bowel disease (IBD) or colitis. These methods are used to silence or knockdown non-cancer gene targets (viral genes, for treatment and prevention of hepatitis B, C; inflammatory genes, for treatment and prevention of inflammatory bowel disease) and others.

The RNAi methods of the invention, including BMGS and BTGS are used to create transient "knockdown" genetic animal models as opposed to genetically engineered knockout models to discover gene functions. The methods are also used as in vitro transfection tool for research and drug development These methods use bacteria with desirable properties (invasiveness, attenuation, steerability) for example, Bifidobacteria and *Listeria*, are used to perform BMGS and BTGS. Invasiveness as well as eukaryotic or prokaryotic transcription of one or several shRNA is conferred to a bacterium using plasmids.

The RNAi methods of the invention, including BMGS and BTGS are used for delivery of gene silencing to the gut and colon, and for oral application in the treatment of various diseases, namely colon cancer treatment and prevention. In another aspect of this embodiment, delivery of gene silencing is extra-intestinal.

1. Bacteria Delivering RNA to Eukaryotic Cells

According to the invention, any microorganism which is capable of delivering a molecule, e.g., an RNA molecule, into the cytoplasm of a target cell, such as by traversing the membrane and entering the cytoplasm of a cell, can be used to deliver RNA to such cells. In a preferred embodiment, the microorganism is a prokaryote. In an even more preferred embodiment, the prokaryote is a bacterium. Also within the scope of the invention are microorganisms other than bacteria which can be used for delivering RNA to a cell. For example, the microorganism can be a fungus, e.g., *Cryptococcus neoformans*, protozoan, e.g., *Trypanosoma cruzi, Toxoplasma gondii, Leishmania donovani*, and *plasmodia*.

As used herein, the term "invasive" when referring to a microorganism, e.g., a bacterium, refers to a microorganism which is capable of delivering at least one molecule, e.g., an RNA or RNA-encoding DNA molecule, to a target cell. An invasive microorganism can be a microorganism which is capable of traversing a cell membrane, thereby entering the cytoplasm of said cell, and delivering at least some of its content, e.g., RNA or RNA-encoding DNA, into the target cell. The process of delivery of the at least one molecule into the target cell preferably does not significantly modify the invasion apparatus.

In a preferred embodiment, the microorganism is a bacterium. A preferred invasive bacterium is a bacterium which is capable of delivering at least one molecule, e.g., an RNA or RNA-encoding DNA molecule, to a target cells, such as by entering the cytoplasm of a eukaryotic cell. Preferred invasive bacteria are live bacteria, e.g., live invasive bacteria.

Invasive microorganisms include microorganisms that are naturally capable of delivering at least one molecule to a target cell, such as by traversing the cell membrane, e.g., a eukaryotic cell membrane, and entering the cytoplasm, as well as microorganisms which are not naturally invasive and which have been modified, e.g., genetically modified, to be invasive. In another preferred embodiment, a microorganism which is not naturally invasive can be modified to become invasive by linking the bacterium to an "invasion factor", also termed "entry factor" or "cytoplasm-targeting factor". As used herein, an "invasion factor" is a factor, e.g., a protein or a group of proteins which, when expressed by a non-invasive bacterium, render the bacterium invasive. As used herein, an "invasion factor" is encoded by a "cytoplasm-targeting gene".

Naturally invasive microorganisms, e.g., bacteria, may have a certain tropism, i.e., preferred target cells. Alternatively, microorganisms, e.g., bacteria can be modified, e.g., genetically, to mimic the tropism of a second microorganism.

Delivery of at least one molecule into a target cell can be determined according to methods known in the art. For example, the presence of the molecule, by the decrease in expression of an RNA or protein silenced thereby, can be detected by hybridization or PCR methods, or by immunological methods which may include the use of an antibody.

Determining whether a microorganism is sufficiently invasive for use in the invention may include determining whether sufficient RNA, was delivered to host cells, relative to the number of microorganisms contacted with the host cells. If the amount of RNA, is low relative to the number of microorganisms used, it may be desirable to further modify the microorganism to increase its invasive potential.

Bacterial entry into cells can be measured by various methods. Intracellular bacteria survive treatment by aminoglycoside antibiotics, whereas extracellular bacteria are rapidly killed. A quantitative estimate of bacterial uptake can be achieved by treating cell monolayers with the antibiotic gentamicin to inactivate extracellular bacteria, then by removing said antibiotic before liberating the surviving intracellular organisms with gentle detergent and determining viable counts on standard bacteriological medium. Furthermore, bacterial entry into cells can be directly observed, e.g., by thin-section-transmission electron microscopy of cell layers or by immunofluorescent techniques (Falkow et al. (1992) Annual Rev. Cell Biol. 8:333). Thus, various techniques can be used to determine whether a specific bacteria is capable of invading a specific type of cell or to confirm bacterial invasion following modification of the bacteria, such modification of the tropism of the bacteria to mimic that of a second bacterium.

Bacteria that can be used for delivering RNA according to the method of the invention are preferably non-pathogenic. However, pathogenic bacteria can also be used, so long as their pathogenicity has been attenuated, to thereby render the bacteria non-harmful to a subject to which it is administered. As used herein, the term "attenuated bacterium" refers to a bacterium that has been modified to significantly reduce or eliminate its harmfulness to a subject. A pathogenic bacterium can be attenuated by various methods, set forth below.

Without wanting to be limited to a specific mechanism of action, the bacterium delivering the RNA into the eukaryotic cell can enter various compartments of the cell, depending on the type of bacterium. For example, the bacterium can be in a vesicle, e.g., a phagocytic vesicle. Once inside the cell, the bacterium can be destroyed or lysed and its contents delivered to the eukaryotic cell. A bacterium can also be engineered to express a phagosome degrading enyzme to allow leakage of RNA from the phagosome. In some embodiments, the bacterium can stay alive for various times in the eukaryotic cell and may continue to produce RNA. The RNA or RNA-encoding DNA can then be released from the bacterium into the cell by, e.g., leakage. In certain embodiments of the invention, the bacterium can also replicate in the eukaryotic cell. In a preferred embodiment, bacterial replication does not kill the host cell. The invention is not limited to delivery of RNA or RNA-encoding DNA by a specific mechanism and is intended to encompass methods and compositions permitting delivery of RNA or RNA-encoding DNA by a bacterium independently of the mechanism of delivery.

Set forth below are examples of bacteria which have been described in the literature as being naturally invasive (section 1.1), as well as bacteria which have been described in the literature as being naturally non-invasive bacteria (section 1.2), as well as bacteria which are naturally non-pathogenic or which are attenuated. Although some bacteria have been described as being non-invasive (section 1.2), these may still be sufficiently invasive for use according to the invention. Whether traditionally described as naturally invasive or non-invasive, any bacterial strain can be modified to modulate, in particular to increase, its invasive characteristics (e.g., as described in section 1.3).

1.1 Naturally Invasive Bacteria

The particular naturally invasive bacteria employed in the present invention is not critical thereto. Examples of such naturally-occurring invasive bacteria include, but are not limited to, *Shigella* spp., *Salmonella* spp., *Listeria* spp., *Rickettsia* spp., and enteroinvasive *Escherichia coli*.

The particular *Shigella* strain employed is not critical to the present invention. Examples of *Shigella* strains which can be employed in the present invention include *Shigella flexneri* 2a (ATCC No. 29903), *Shigella sonnei* (ATCC No. 29930), and *Shigella disenteriae* (ATCC No. 13313). An attenuated *Shigella* strain, such as *Shigella flexneri* 2a 2457T aroA virG mutant CVD 1203 (Noriega et al. supra), *Shigella flexneri* M90T icsA mutant (Goldberg et al. Infect. Immun., 62:5664-5668 (1994)), *Shigella flexneri* Y SFL114 aroD mutant (Karnell et al. Vacc., 10:167-174 (1992)), and *Shigella flexneri* aroA aroD mutant (Verma et al. Vacc., 9:6-9 (1991)) are preferably employed in the present invention. Alternatively, new attenuated *Shigella* spp. strains can be constructed by introducing an attenuating mutation either singularly or in conjunction with one or more additional attenuating mutations.

At least one advantage to *Shigella* RNA vaccine vectors is their tropism for lymphoid tissue in the colonic mucosal surface. In addition, the primary site of *Shigella* replication is believed to be within dendritic cells and macrophages, which are commonly found at the basal lateral surface of M cells in mucosal lymphoid tissues (reviewed by McGhee, J. R. et al. (1994) Reproduction, Fertility, & Development 6:369; Pascual, D. W. et al. (1994) *Immunomethods* 5:56). As such, *Shigella* vectors may provide a means to express antigens in these professional antigen presenting cells. Another advantage of *Shigella* vectors is that attenuated *Shigella* strains deliver nucleic acid reporter genes in vitro and in vivo (Sizemore, D. R. et al. (1995) Science 270:299; Courvalin, P. et al. (1995) Comptes Rendus de 1 Academie des Sciences Serie III-Sciences de la Vie-Life Sciences 318:1207; Powell, R. J. et al. (1996) In: Molecular approaches to the control of infectious diseases. F. Brown, E. Norrby, D. Burton and J. Mekalanos, eds. Cold Spring Harbor Laboratory Press, New York. 183; Anderson, R. J. et al. (1997) Abstracts for the 97th General Meeting of the American Society for Microbiology: E.). On the practical side, the tightly restricted host specificity of *Shigella* stands to prevent the spread of *Shigella* vectors into the food chain via intermediate hosts. Furthermore, attenuated strains that are highly attenuated in rodents, primates and volunteers have been developed (Anderson et al. (1997) supra; Li, A. et al. (1992) Vaccine 10:395; Li, A. et al. (1993) Vaccine 11:180; Karnell, A. et al. (1995) Vaccine 13:88; Sansonetti, P. J. and J. Arondel (1989) Vaccine 7:443; Fontaine, A. et al. (1990) Research in Microbiology 141:907; Sansonetti, P. J. et al. (1991) Vaccine 9:416; Noriega, F. R. et al. (1994) Infection & Immunity 62:5168; Noriega, F. R. et al. (1996) Infection & Immunity 64:3055; Noriega, F. R. et al. (1996) Infection & Immunity 64:23; Noriega, F. R. et al. (1996) Infection & Immunity 64:3055; Kotloff, K. L. et al. (1996) Infection & Immunity 64:4542). This latter knowledge will allow the development of well tolerated *Shigella* vectors for use in humans.

Attenuating mutations can be introduced into bacterial pathogens using non-specific mutagenesis either chemically, using agents such as N-methyl-N'-nitro-N-nitrosoguanidine, or using recombinant DNA techniques; classic genetic techniques, such as Tn10 mutagenesis, P22-mediated transduction, λ, phage mediated crossover, and conjugational transfer; or site-directed mutagenesis using recombinant DNA techniques. Recombinant DNA techniques are preferable since strains constructed by recombinant DNA techniques are far more defined. Examples of such attenuating mutations include, but are not limited to:

(i) auxotrophic mutations, such as aro (Hoiseth et al. Nature, 291:238-239 (1981)), gua (McFarland et al. Microbiol. Path., 3:129-141 (1987)), nad (Park et al. J. Bact., 170: 3725-3730 (1988), thy (Nnalue et al. Infect. Immun., 55:955-962 (1987)), and asd (Curtiss, supra) mutations;

(ii) mutations that inactivate global regulatory functions, such as cya (Curtiss et al. Infect. Immun., 55:3035-3043 (1987)), crp (Curtiss et al (1987), supra), phoP/phoQ (Groisman et al. Proc. Natl. Acad. Sci., USA, 86:7077-7081 (1989); and Miller et al. Proc. Natl. Acad. Sci., USA, 86:5054-5058 (1989)), phop$^c$ (Miller et al. J. Bact., 172:2485-2490 (1990)) or ompR (Dorman et al. Infect. Immun, 57:2136-2140 (1989)) mutations;

(iii) mutations that modify the stress response, such as recA (Buchmeier et al. Mol. Micro., 7:933-936 (1993)), htrA (Johnson et al. Mol. Micro., 5:401-407 (1991)), htpR (Neidhardt et al. Biochem. Biophys. Res. Com., 100:894-900 (1981)), hsp (Neidhardt et al. Ann. Rev. Genet., 18:295-329 (1984)) and groEL (Buchmeier et al. Sci., 248:730-732 (1990)) mutations;

(iv) mutations in specific virulence factors, such as IsyA (Libby et al. Proc. Natl. Acad. Sci., USA, 91:489-493 (1994)), pag or prg (Miller et al (1990), supra; and Miller et al (1989), supra), iscA or virG (d'Hauteville et al. Mol. Micro., 6:833-841 (1992)), plcA (Mengaud et al. Mol. Microbiol., 5:367-72 (1991); Camilli et al. J. Exp. Med, 173:751-754 (1991)), and act (Brundage et al. Proc. Natl. Acad. Sci., USA, 90:11890-11894 (1993)) mutations;

(v) mutations that affect DNA topology, such as topA (Galan et al. Infect. Immun., 58:1879-1885 (1990));

(vi) mutations that disrupt or modify the cell cycle, such as min (de Boer et al. Cell, 56:641-649 (1989)).

(vii) introduction of a gene encoding a suicide system, such as sacB (Recorbet et al. App. Environ. Micro., 59:1361-1366 (1993); Quandt et al. Gene, 127:15-21 (1993)), nuc (Ahrenholtz et al. App. Environ. Micro., 60:3746-3751 (1994)), hok, gef, kil, or phlA (Molin et al. Ann Rev. Microbiol., 47:139-166 (1993));

(viii) mutations that alter the biogenesis of lipopolysaccharide and/or lipid A, such as rFb (Raetz in *Esherishia coli* and *Salmonella typhimurium*, Neidhardt et al., Ed., ASM Press, Washington D.C. pp 1035-1063 (1996)), galE (Hone et al. J. Infect. Dis., 156:164-167 (1987)) and htrB (Raetz, supra), msbB (Reatz, supra)

(ix) introduction of a bacteriophage lysis system, such as lysogens encoded by P22 (Rennell et al. Virol, 143:280-289 (1985)), λ, murein transglycosylase (Bienkowska-Szewczyk et al. Mol. Gen. Genet., 184:111-114 (1981)) or S-gene (Reader et al. Virol, 43:623-628 (1971)); and The attenuating mutations can be either constitutively expressed or under the control of inducible promoters, such as the temperature sensitive heat shock family of promoters (Neidhardt et al. supra), or the anaerobically induced nirB promoter (Harborne et al. Mol. Micro., 6:2805-2813 (1992)) or repressible promoters, such as uapA (Gorfinkiel et al. J. Biol. Chem., 268:23376-23381 (1993)) or gcv (Stauffer et al. J. Bact., 176:6159-6164 (1994)).

The particular *Listeria* strain employed is not critical to the present invention. Examples of *Listeria* strains which can be employed in the present invention include *Listeria monocytogenes* (ATCC No. 15313). Attenuated *Listeria* strains, such as *L. monocytogenes* actA mutant (Brundage et al. supra) or *L. monocytogenes* plcA (Camilli et al. J. Exp. Med., 173:751-754 (1991)) are preferably used in the present invention. Alternatively, new attenuated *Listeria* strains can be constructed by introducing one or more attenuating mutations in groups (i) to (vii) as described for *Shigella* spp. above.

The particular *Salmonella* strain employed is not critical to the present invention. Examples of *Salmonella* strains which can be employed in the present invention include *Salmonella typhi* (ATCC No. 7251) and *S. typhimurium* (ATCC No. 13311). Attenuated *Salmonella* strains are preferably used in the present invention and include *S. typhi*-aroC-aroD (Hone et al. Vacc. 9:810 (1991) and *S. typhimurium*-aroA mutant (Mastroeni et al. Micro. Pathol. 13:477 (1992)). Alternatively, new attenuated *Salmonella* strains can be constructed by introducing one or more attenuating mutations as described fro *Shigella* spp. above.

The particular *Rickettsia* strain employed is not critical to the present invention. Examples of *Rickettsia* strains which can be employed in the present invention include *Rickettsia* Rickettsiae (ATCC Nos. VR149 and VR891), *Ricketsia prowaseckii* (ATCC No. VR233), *Rickettsia tsutsugamuchi* (ATCC Nos. VR312, VR150 and VR609), *Rickettsia mooseri* (ATCC No. VR144), *Rickettsia sibirica* (ATCC No. VR151), and Rochalimaea quitana (ATCC No. VR358). Attenuated *Rickettsia* strains are preferably used in the present invention and can be constructed by introducing one or more attenuating mutations in groups (i) to (vii) as described for *Shigella* spp. above.

The particular enteroinvasive *Escherichia* strain employed is not critical to the present invention. Examples of enteroinvasive *Escherichia* strains which can be employed in the present invention include *Escherichia coli* strains 4608-58, 1184-68, 53638-C-17, 13-80, and 6-81 (Sansonetti et al. Ann. Microbiol. (Inst. Pasteur), 132A:351-355 (1982)). Attenuated enteroinvasive *Escherichia* strains are preferably used in the present invention and can be constructed by introducing one or more attenuating mutations in groups (i) to (vii) as described for *Shigella* spp. above.

Furthermore, since certain microorganisms other than bacteria can also interact with integrin molecules (which are receptors for certain invasion factors) for cellular uptake, such microorganisms can also be used for introducing RNA into target cells. For example, viruses, e.g., foot-and-mouth disease virus, echovirus, and adenovirus, and eukaryotic pathogens, e.g., *Histoplasma capsulatum* and *Leishmania major* interact with integrin molecules.

1.2 Less Invasive Bacteria

Examples of bacteria which can be used in the invention and which have been described in the literature as being non-invasive or at least less invasive than the bacteria listed in the previous section (1.1) include, but are not limited to, *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Vibrio* spp., *Bacillus* spp., and *Erysipelothrix* spp. It may be necessary to modify these bacteria to increase their invasive potential.

The particular *Yersinia* strain employed is not critical to the present invention. Examples of *Yersinia* strains which can be employed in the present invention include *Y. enterocolitica* (ATCC No. 9610) or *Y. pestis* (ATCC No. 19428). Attenuated *Yersinia* strains, such as *Y. enterocolitica* Ye03-R2 (al-Hendy et al. Infect. Immun, 60:870-875 (1992)) or *Y. enterocolitica* aroA (O'Gaora et al. Micro. Path., 9:105-116 (1990)) are preferably used in the present invention. Alternatively, new attenuated *Yersinia* strains can be constructed by introducing one or more attenuating mutations in groups (i) to (vii) as described for *Shigella* spp. above.

The particular *Escherichia* strain employed is not critical to the present invention. Examples of *Escherichia* strains which can be employed in the present invention include *E. coli* H10407 (Elinghorst et al. Infect. Immun., 60:2409-2417 (1992)), and *E. coli* EFC4, CFT325 and CPZ005 (Donnenberg et al. J. Infect. Dis., 169:831-838 (1994)). Attenuated *Escherichia* strains, such as the attenuated turkey pathogen *E. coli* 02 carAB mutant (Kwaga et al. Infect. Immun., 62:3766-3772 (1994)) are preferably used in the present invention. Alternatively, new attenuated *Escherichia* strains can be constructed by introducing one or more attenuating mutations in groups (i) to (vii) as described for *Shigella* spp. above.

The particular *Klebsiella* strain employed is not critical to the present invention. Examples of *Klebsiella* strains which can be employed in the present invention include *K. pneumoniae* (ATCC No. 13884). Attenuated *Klebsiella* strains are preferably used in the present invention, and can be constructed by introducing one or more attenuating mutations in groups (i) to (vii) as described for *Shigella* spp. above.

The particular *Bordetella* strain employed is not critical to the present invention. Examples of *Bordetella* strains which can be employed in the present invention include *B. bronchiseptica* (ATCC No. 19395). Attenuated *Bordetella* strains are preferably used in the present invention, and can be constructed by introducing one or more attenuating mutations in groups (i) to (vii) as described for *Shigella* spp. above.

The particular *Neisseria* strain employed is not critical to the present invention. Examples of *Neisseria* strains which can be employed in the present invention include *N. meningitidis* (ATCC No. 13077) and *N. gonorrhoeae* (ATCC No. 19424). Attenuated *Neisseria* strains, such as *N. gonorrhoeae* MS11 aro mutant (Chamberlain et al. Micro. Path., 15:51-63 (1993)) are preferably used in the present invention. Alternatively, new attenuated *Neisseria* strains can be constructed by introducing one or more attenuating mutations in groups (i) to (vii) as described for *Shigella* spp. above.

The particular *Aeromonas* strain employed is not critical to the present invention. Examples of *Aeromonas* strains which can be employed in the present invention include *A. eucrenophila* (ATCC No. 23309). Alternatively, new attenuated *Aeromonas* strains can be constructed by introducing one or more attenuating mutations in groups (i) to (vii) as described for *Shigella* spp. above.

The particular *Franciesella* strain employed is not critical to the present invention. Examples of *Franciesella* strains which can be employed in the present invention include *F. tularensis* (ATCC No. 15482). Attenuated *Franciesella* strains are preferably used in the present invention, and can be constructed by introducing one or more attenuating mutations in groups (i) to (vii) as described for *Shigella* spp. above.

The particular *Corynebacterium* strain employed is not critical to the present invention. Examples of *Corynebacterium* strains which can be employed in the present invention include *C. pseudotuberculosis* (ATCC No. 19410). Attenuated *Corynebacterium* strains are preferably used in the present invention, and can be constructed by introducing one or more attenuating mutations in groups (i) to (vii) as described for *Shigella* spp. above.

The particular *Citrobacter* strain employed is not critical to the present invention. Examples of *Citrobacter* strains which can be employed in the present invention include *C. freundii* (ATCC No. 8090). Attenuated *Citrobacter* strains are preferably used in the present invention, and can be constructed by introducing one or more attenuating mutations in groups (i) to (vii) as described for *Shigella* spp. above.

The particular *Chlamydia* strain employed is not critical to the present invention. Examples of *Chlamydia* strains which can be employed in the present invention include *C. pneumoniae* (ATCC No. VR1310). Attenuated *Chlamydia* strains are preferably used in the present invention, and can be constructed by introducing one or more attenuating mutations in groups (i) to (vii) as described for *Shigella* spp. above.

The particular *Hemophilus* strain employed is not critical to the present invention. Examples of *Hemophilus* strains which can be employed in the present invention include *H. sornnus* (ATCC No. 43625). Attenuated *Hemophilus* strains are preferably used in the present invention, and can be constructed by introducing one or more attenuating mutations in groups (i) to (vii) as described for *Shigella* spp. above.

The particular *Brucella* strain employed is not critical to the present invention. Examples of *Brucella* strains which can be employed in the present invention include *B. abortus* (ATCC No. 23448). Attenuated *Brucella* strains are preferably used in the present invention, and can be constructed by introducing one or more attenuating mutations in groups (i) to (vii) as described for *Shigella* spp. above.

The particular *Mycobacterium* strain employed is not critical to the present invention. Examples of *Mycobacterium* strains which can be employed in the present invention include *M. intracellulare* (ATCC No. 13950) and *M. tuberculosis* (ATCC No. 27294). Attenuated *Mycobacterium* strains are preferably used in the present invention, and can be constructed by introducing one or more attenuating mutations in groups (i) to (vii) as described for *Shigella* spp. above.

The particular *Legionella* strain employed is not critical to the present invention. Examples of *Legionella* strains which can be employed in the present invention include *L. pneumophila* (ATCC No. 33156). Attenuated *Legionella* strains, such as a *L. pneumophila* mip mutant (Ott, FEMS Micro. Rev., 14:161-176 (1994)) are preferably used in the present invention. Alternatively, new attenuated *Legionella* strains can be constructed by introducing one or more attenuating mutations in groups (i) to (vii) as described for *Shigella* spp. above.

The particular *Rhodococcus* strain employed is not critical to the present invention. Examples of *Rhodococcus* strains which can be employed in the present invention include *R. equi* (ATCC No. 6939). Attenuated *Rhodococcus* strains are preferably used in the present invention, and can be constructed by introducing one or more attenuating mutations in groups (i) to (vii) as described for *Shigella* spp. above.

The particular *Pseudomonas* strain employed is not critical to the present invention. Examples of *Pseudomonas* strains which can be employed in the present invention include *P. aeruginosa* (ATCC No. 23267). Attenuated *Pseudomonas* strains are preferably used in the present invention, and can be constructed by introducing one or more attenuating mutations in groups (i) to (vii) as described for *Shigella* spp. above.

The particular *Helicobacter* strain employed is not critical to the present invention. Examples of *Helicobacter* strains which can be employed in the present invention include *H. mustelae* (ATCC No. 43772). Attenuated *Helicobacter* strains are preferably used in the present invention, and can be constructed by introducing one or more attenuating mutations in groups (i) to (vii) as described for *Shigella* spp. above.

The particular *Salmonella* strain employed is not critical to the present invention. Examples of *Salmonella* strains which can be employed in the present invention include *Salmonella typhi* (ATCC No. 7251) and *S. typhimurium* (ATCC No. 13311). Attenuated *Salmonella* strains are preferably used in the present invention and include *S. typhi* aroC aroD (Hone et al. Vacc., 9:810-816 (1991)) and *S. typhimurium* aroA mutant (Mastroeni et al. Micro. Pathol, 13:477-491 (1992))). Alternatively, new attenuated *Salmonella* strains can be constructed by introducing one or more attenuating mutations in groups (i) to (vii) as described for *Shigella* spp. above.

The particular *Vibrio* strain employed is not critical to the present invention. Examples of *Vibrio* strains which can be employed in the present invention include *Vibrio cholerae* (ATCC No. 14035) and *Vibrio cincinnatiensis* (ATCC No. 35912). Attenuated *Vibrio* strains are preferably used in the present invention and include *V. cholerae* RSI virulence mutant (Taylor et al. J. Infect. Dis., 170:1518-1523 (1994)) and *V. cholerae* ctxA, ace, zot, cep mutant (Waldor et al. J. Infect. Dis., 170:278-283 (1994)). Alternatively, new attenuated *Vibrio* strains can be constructed by introducing one or more attenuating mutations in groups (i) to (vii) as described for *Shigella* spp. above.

The particular *Bacillus* strain employed is not critical to the present invention. Examples of *Bacillus* strains which can be employed in the present invention include *Bacillus subtilis* (ATCC No. 6051). Attenuated *Bacillus* strains are preferably used in the present invention and include *B. anthracis* mutant pX01 (Welkos et al. Micro. Pathol, 14:381-388 (1993)) and attenuated BCG strains (Stover et al. Nat., 351:456-460 (1991)). Alternatively, new attenuated *Bacillus* strains can be constructed by introducing one or more attenuating mutations in groups (i) to (vii) as described for *Shigella* spp. above.

The particular *Erysipelothrix* strain employed is not critical to the present invention. Examples of *Erysipelothrix* strains which can be employed in the present invention include *Erysipelothrix rhusiopathiae* (ATCC No. 19414) and *Erysipelothrix tonsillarum* (ATCC No. 43339). Attenuated *Erysipelothrix* strains are preferably used in the present invention and include *E. rhusiopathiae* Kg-1a and Kg-2 (Watarai et al. J. Vet. Med. Sci., 55:595-600 (1993)) and *E. rhusiopathiae* ORVAC mutant (Markowska-Daniel et al. Int. J. Med. Microb. Virol. Parisit. Infect. Dis., 277:547-553 (1992)). Alternatively, new attenuated *Erysipelothrix* strains can be constructed by introducing one or more attenuating mutations in groups (i) to (vii) as described for *Shigella* spp. above.

1.3. Methods for Increasing the Invasive Properties of a Bacterial Strain

Whether organisms have been traditionally described as invasive or non-invasive, these organisms can be engineered to increase their invasive properties, e.g., by mimicking the invasive properties of *Shigella* spp., *Listeria* spp., *Rickettsia* spp., or enteroinvasive *E. coli* spp. For example, one or more genes that enable the microorganism to access the cytoplasm of a cell, e.g., a cell in the natural host of said non-invasive bacteria, can be introduced into the microorganism.

Examples of such genes referred to herein as "cytoplasm-targeting genes" include genes encoding the proteins that enable invasion by *Shigella* or the analogous invasion genes of entero-invasive *Escherichia*, or listeriolysin O of *Listeria*, as such techniques are known to result in rendering a wide array of invasive bacteria capable of invading and entering the cytoplasm of animal cells (Formal et al. Infect. Immun., 46:465 (1984); Bielecke et al. Nature, 345:175-176 (1990); Small et al. In: Microbiology-1986, pages 121-124, Levine et al. Eds., American Society for Microbiology, Washington, D.C. (1986); Zychlinsky et al. Molec. Micro., 11:619-627 (1994); Gentschev et al. (1995) Infection & Immunity 63:4202; Isberg, R. R. and S. Falkow (1985) Nature 317:262; and Isberg, R. R. et al. (1987) Cell 50:769). Methods for transferring the above cytoplasm-targeting genes into a bacterial strain are well known in the art. Another preferred gene which can be introduced into bacteria to increase their invasive character encodes the invasin protein from *Yersinia pseudotuberculosis*, (Leong et al. EMBO J., 9:1979 (1990)). Invasin can also be introduced in combination with listeriolysin, thereby further increasing the invasive character of the bacteria relative to the introduction of either of these genes. The above genes have been described for illustrative purposes; however, it will be obvious to those skilled in the art that any gene or combination of genes, from one or more sources, that participates in the delivery of a molecule, in particular an RNA or RNA-encoding DNA molecule, from a microorganism into the cytoplasm of a cell, e.g., an animal cell, will suffice. Thus, such genes are not limited to bacterial genes, and include viral genes, such as influenza virus hemagglutinin HA-2 which promotes endosmolysis (Plank et al. J. Biol. Chem., 269:12918-12924 (1994)).

The above cytoplasm-targeting genes can be obtained by, e.g., PCR amplification from DNA isolated from an invasive bacterium carrying the desired cytoplasm-targeting gene. Primers for PCR can be designed from the nucleotide sequences available in the art, e.g., in the above-listed references and/or in GenBank, which is publicly available on the internet (www.ncbi.nlm.nih.gov/). The PCR primers can be designed to amplify a cytoplasm-targeting gene, a cytoplasm-targeting operon, a cluster of cytoplasm-targeting genes, or a regulon of cytoplasm-targeting genes. The PCR strategy employed will depend on the genetic organization of the cytoplasm-targeting gene or genes in the target invasive bacteria. The PCR primers are designed to contain a sequence that is homologous to DNA sequences at the beginning and end of the target DNA sequence. The cytoplasm-targeting genes can then be introduced into the target bacterial strain, e.g., by using Hfr transfer or plasmid mobilization (Miller, A Short Course in Bacterial Genetics, Cold Spring Harbor Laboratory Press, Cold Spring Harbor, N.Y. (1992); Bothwell et al. supra; and Ausubel et al. supra), bacteriophage-mediated transduction (de Boer, supra; Miller, supra; and Ausubel et al. supra), chemical transformation (Bothwell et al. supra; Ausubel et al. supra), electroporation (Bothwel et al. supra; Ausubel et al. supra; and Sambrook, Molecular Cloning: A Laboratory Manual, Cold Spring Harbor Laboratory Press, Cold Spring Harbor, N.Y.) and physical transformation techniques (Johnston et al. supra; and Bothwell, supra). The cytoplasm-targeting genes can be incorporated into lysogenic bacteriophage (de Boer et al. Cell, 56:641-649 (1989)), plasmids vectors (Curtiss et al. supra) or spliced into the chromosome (Hone et al. supra) of the target strain.

In addition to genetically engineering bacteria to increase their invasive properties, as set forth above, bacteria can also be modified by linking an invasion factor to the bacteria. Accordingly, in one embodiment, a bacterium is rendered more invasive by coating the bacterium, either covalently or non-covalently, with an invasion factor, e.g., the protein invasin, invasin derivatives, or a fragment thereof sufficient for invasiveness. In fact, it has been shown that non-invasive bacterial cells coated with purified invasin from *Yersinia pseudotuberculosis* or the carboxyl-terminal 192 amino acids of invasin are able to enter mammalian cells (Leong et al. (1990) EMBO J. 9:1979). Furthermore, latex beads coated with the carboxyl terminal region of invasin are efficiently internalized by mammalian cells, as are strains of *Staphylococcus aureus* coated with antibody-immobilized invasin (reviewed in Isberg and Tran van Nhieu (1994) Ann. Rev. Genet. 27:395). Alternatively, a bacterium can also be coated with an antibody, variant thereof, or fragment thereof which binds specifically to a surface molecule recognized by a bacterial entry factor. For example, it has been shown that bacteria are internalized if they are coated with a monoclonal antibody directed against an integrin molecule, e.g., $\alpha 5\beta 1$, known to be the surface molecule with which the bacterial invasin protein interacts (Isberg and Tran van Nhieu, supra). Such antibodies can be prepared according to methods known in the art. The antibodies can be tested for efficacy in mediating bacterial invasiveness by, e.g., coating bacteria with the antibody, contacting the bacteria with eukaryotic cells having a surface receptor recognized by the antibody, and monitoring the presence of intracellular bacteria, according to the methods described above. Methods for linking an invasion factor to the surface of a bacterium are known in the art and include cross-linking.

2. Target Cells

The invention provides a method for delivering RNA to any type of target cell. As used herein, the term "target cell" refers to a cell which can be invaded by a bacterium, i.e., a cell which has the necessary surface receptor for recognition by the bacterium.

Preferred target cells are eukaryotic cells. Even more preferred target cells are animal cells. "Animal cells" are defined as nucleated, non-chloroplast containing cells derived from or present in multicellular organisms whose taxanomic position lies within the kingdom animalia. The cells may be present in the intact animal, a primary cell culture, explant culture or a transformed cell line. The particular tissue source of the cells is not critical to the present invention.

The recipient animal cells employed in the present invention are not critical thereto and include cells present in or derived from all organisms within the kingdom animalia, such as those of the families mammalia, pisces, avian, reptilia.

Preferred animal cells are mammalian cells, such as humans, bovine, ovine, porcine, feline, canine, goat, equine, and primate cells. The most preferred animal cells are human cells.

In a preferred embodiment, the target cell is in a mucosal surface. Certain enteric pathogens, e.g., *E. coli, Shigella, Listeria*, and *Salmonella*, are naturally adapted for this application, as these organisms possess the ability to attach to and invade host mucosal surfaces (Kreig et al. supra). Therefore, in the present invention, such bacteria can deliver RNA molecules or RNA-encoding DNA to cells in the host mucosal compartment.

Although certain types of bacteria may have a certain tropism, i.e., preferred target cells, delivery of RNA or RNA-encoding DNA to a certain type of cell can be achieved by choosing a bacterium which has a tropism for the desired cell type or which is modified such as to be able to invade the desired cell type. Thus, e.g., a bacterium could be genetically engineered to mimic mucosal tissue tropism and invasive properties, as discussed above, to thereby allow said bacteria to invade mucosal tissue, and deliver RNA or RNA-encoding DNA to cells in those sites.

Bacteria can also be targeted to other types of cells. For example, bacteria can be targeted to erythrocytes of humans and primates by modifying bacteria to express on their surface either, or both of, the *Plasmodium vivax* reticulocyte binding proteins-1 and -2, which bind specifically to erythrocytes in humans and primates (Galinski et al. Cell, 69:1213-1226 (1992)). In another embodiment, bacteria are modified to have on their surface asialoorosomucoid, which is a ligand for the asilogycoprotein receptor on hepatocytes (Wu et al. J. Biol. Chem., 263:14621-14624 (1988)). In yet another embodiment, bacteria are coated with insulin-poly-L-lysine, which has been shown to target plasmid uptake to cells with an insulin receptor (Rosenkranz et al. Expt. Cell Res., 199: 323-329 (1992)). Also within the scope of the invention are bacteria modified to have on their surface p60 of *Listeria monocytogenes*, which allows for tropism for hepatocytes (Hess et al. Infect. Immun., 63:2047-2053 (1995)), or a 60 kD surface protein from *Trypanosoma cruzi* which causes specific binding to the mammalian extra-cellular matrix by binding to heparin, heparin sulfate and collagen (Ortega-Barria et al. Cell, 67:411-421 (1991)).

Yet in another embodiment, a cell can be modified to become a target cell of a bacterium for delivery of RNA. Accordingly, a cell can be modified to express a surface antigen which is recognized by a bacterium for its entry into the cell, i.e., a receptor of an invasion factor. The cell can be modified either by introducing into the cell a nucleic acid encoding a receptor of an invasion factor, such that the surface antigen is expressed in the desired conditions. Alternatively, the cell can be coated with a receptor of an invasion factor. Receptors of invasion factors include proteins belonging to the integrin receptor superfamily. A list of the type of integrin receptors recognized by various bacteria and other microorganisms can be found, e.g., in Isberg and Tran Van Nhieu (1994) Ann Rev. Genet. 27:395. Nucleotide sequences for the integrin subunits can be found, e.g., in GenBank, publicly available on the internet.

As set forth above, yet other target cells include fish, avian, and reptilian cells. Examples of bacteria which are naturally invasive for fish, avian, and reptilian cells are set forth below.

Examples of bacteria which can naturally access the cytoplasm of fish cells include, but are not limited to *Aeromonas salminocida* (ATCC No. 33658) and *Aeromonas schuberii* (ATCC No. 43700). Attenuated bacteria are preferably used in the invention, and include *A. salmonicidia* vapA (Gustafson et al. J. Mol. Biol., 237:452-463 (1994)) or *A. salmonicidia* aromatic-dependent mutant (Vaughan et al. Infect. Immun., 61:2172-2181 (1993)).

Examples of bacteria which can naturally access the cytoplasm of avian cells include, but are not restricted to, *Salmonella galinarum* (ATCC No. 9184), *Salmonella enteriditis* (ATCC No. 4931) and *Salmonella typhimurium* (ATCC No. 6994). Attenuated bacteria are preferred to the invention and include attenuated *Salmonella* strains such as *S. galinarum* cya crp mutant (Curtiss et al. (1987) supra) or *S. enteritidis* aroA aromatic-dependent mutant CVL30 (Cooper et al. Infect. Immun, 62:4739-4746 (1994)).

Examples of bacteria which can naturally access the cytoplasm of reptilian cells include, but are not restricted to, *Salmonella typhimurium* (ATCC No. 6994). Attenuated bacteria are preferable to the invention and include, attenuated strains such as *S. typhimuirum* aromatic-dependent mutant (Hormaeche et al. supra).

The invention also provides for delivery of RNA to other eukaryotic cells, e.g., plant cells, so long as there are microorganisms which are capable of invading such cells, either naturally or after having been modified to become invasive. Examples of microorganisms which can invade plant cells include *Agrobacterium tumerfacium*, which uses a pilus-like structure which binds to the plant cell via specific receptors, and then through a process that resembles bacterial conjugation, delivers at least some of its content to the plant cell.

Set forth below are examples of cell lines to which RNA can be delivered according to the method of this invention.

Examples of human cell lines include but are not limited to ATCC Nos. CCL 62, CCL 159, HTB 151, HTB 22, CCL 2, CRL 1634, CRL 8155, HTB 61, and HTB104.

Examples of bovine cell lines include ATCC Nos. CRL 6021, CRL 1733, CRL 6033, CRL 6023, CCL 44 and CRL 1390.

Examples of ovine cells lines include ATCC Nos. CRL 6540, CRL 6538, CRL 6548 and CRL 6546.

Examples of porcine cell lines include ATCC Nos. CL 184, CRL 6492, and CRL 1746.

Examples of feline cell lines include CRL 6077, CRL 6113, CRL 6140, CRL 6164, CCL 94, CCL 150, CRL 6075 and CRL 6123.

Examples of buffalo cell lines include CCL 40 and CRL 6072.

Examples of canine cells include ATCC Nos. CRL 6213, CCL 34, CRL 6202, CRL 6225, CRL 6215, CRL 6203 and CRL 6575.

Examples of goat derived cell lines include ATCC No. CCL 73 and ATCC No. CRL 6270.

Examples of horse derived cell lines include ATCC Nos. CCL 57 and CRL 6583.

Examples of deer cell lines include ATCC Nos. CRL 6193-6196.

Examples of primate derived cell lines include those from chimpanzee's such as ATCC Nos. CRL 6312, CRL 6304, and CRL 1868; monkey cell lines such as ATCC Nos. CRL 1576, CCL 26, and CCL 161; orangautan cell line ATCC No. CRL 1850; and gorilla cell line ATCC No. CRL 1854.

4. Pharmaceutical Compositions

In a preferred embodiment of the invention, the invasive bacteria containing the RNA molecules, and/or DNA encoding such, are introduced into an animal by intravenous, intramuscular, intradermal, intraperitoneally, peroral, intranasal, intraocular, intrarectal, intravaginal, intraosseous, oral, immersion and intraurethral inoculation routes.

The amount of the live invasive bacteria of the present invention to be administered to a subject will vary depending on the species of the subject, as well as the disease or condition that is being treated. Generally, the dosage employed will be about $10^3$ to $10^{11}$ viable organisms, preferably about $10^5$ to $10^9$ viable organisms per subject.

The invasive bacteria of the present invention are generally administered along with a pharmaceutically acceptable carrier and/or diluent. The particular pharmaceutically acceptable carrier an/or diluent employed is not critical to the present invention. Examples of diluents include a phosphate buffered saline, buffer for buffering against gastric acid in the stomach, such as citrate buffer (pH 7.0) containing sucrose, bicarbonate buffer (pH 7.0) alone (Levine et al. J. Clin. Invest., 79:888-902 (1987); and Black et al J. Infect. Dis., 155:1260-1265 (1987)), or bicarbonate buffer (pH 7.0) containing ascorbic acid, lactose, and optionally aspartame (Levine et al. Lancet, 11:467-470 (1988)). Examples of carriers include proteins, e.g., as found in skim milk, sugars, e.g., sucrose, or polyvinylpyrrolidone. Typically these carriers would be used at a concentration of about 0.1-30% (w/v) but preferably at a range of 1-10% (w/v).

Set forth below are other pharmaceutically acceptable carriers or diluents which may be used for delivery specific routes. Any such carrier or diluent can be used for administration of the bacteria of the invention, so long as the bacteria are still capable of invading a target cell. In vitro or in vivo tests for invasiveness can be performed to determine appropriate diluents and carriers. The compositions of the invention can be formulated for a variety of types of administration, including systemic and topical or localized administration. Lyophilized forms are also included, so long as the bacteria are invasive upon contact with a target cell or upon administration to the subject. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the composition, e.g., bacteria, of the invention can be formulated in liquid solutions, preferably in physiologically compatible buffers such as Hank's solution or Ringer's solution.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner.

For administration by inhalation, the pharmaceutical compositions for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the composition, e.g., bacteria, and a suitable powder base such as lactose or starch.

The pharmaceutical compositions may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The pharmaceutical compositions may also be formulated in rectal, intravaginal or intraurethral compositions such as suppositories or retention enemas, e.g., containing conventional suppository bases such as cocoa butter or other glycerides.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the bacteria of the invention are formulated into ointments, salves, gels, or creams as generally known in the art, so long as the bacteria are still invasive upon contact with a target cell.

The compositions may, if desired, be presented in a pack or dispenser device and/or a kit which may contain one or more unit dosage forms containing the active ingredient. The pack may for example comprise metal or plastic foil, such as a blister pack. The pack or dispenser device may be accompanied by instructions for administration.

The invasive bacteria containing the RNA or RNA-encoding DNA to be introduced can be used to infect animal cells that are cultured in vitro, such as cells obtained from a subject. These in vitro-infected cells can then be introduced into animals, e.g., the subject from which the cells were obtained initially, intravenously, intramuscularly, intradermally, or intraperitoneally, or by any inoculation route that allows the cells to enter the host tissue. When delivering RNA to individual cells, the dosage of viable organisms to administered will be at a multiplicity of infection ranging from about 0.1 to $10^6$, preferably about $10^2$ to $10^4$ bacteria per cell.

In yet another embodiment of the present invention, bacteria can also deliver RNA molecules encoding proteins to cells, e.g., animal cells, from which the proteins can later be harvested or purified. For example, a protein can be produced in a tissue culture cell.

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The present invention is further illustrated by the following examples which should not be construed as limiting in any way. The contents of all cited references including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N.

Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

EXAMPLES

Methods siRNA-Generating Plasmid Construction:

Oligonucleotides were obtained at 0.2 µmol from QIAGEN with PAGE purification. After annealing, oligonucleotides were inserted into the BamHI and HindIII binding sites within pSilencer 2.0-U6 (Ambion, Inc.) according to the manufacturer's instructions.

The following sequences were used:

The k-Ras-1 and -2 64-mers target the nucleotides encoding for amino acids 9-15 of k-Ras protein which spans the specific mutation of V12.

```
k-Ras-1 (64-mer):
                                                   (SEQ ID NO: 1)
5'gATCCCgTTggAgCTgTTggCgTAgTTCAAgAgACTACgCCAACAgCTCCAACTTTTTTggAAA3' k-Ras-2 (64-mer):
                                                   (SEQ ID NO: 2)
5'AgCTTTTCCAAAAAAgTTggAgCTgTTggCgTAgTCTCTTgAACTACgCCAACAgCTCCAACgg3'
```

The β-Catenin-1 and -2 64-mers target the nucleotides encoding for amino acids 79-85 within the catenin protein

```
β-Catenin-1 (64mer):
                                                   (SEQ ID NO: 3)
5'gATCCCAgCTgATATTgATggACAgTTCAAgAgACTgTCCATCAATA TCAgCTTTTTTggAAA3'

β-Catenin-2 (64mer):
                                                   (SEQ ID NO: 4)
5'AgCTTTTCCAAAAAAgCTgATATTgATggACAgTCTCTTgAACTgT CCATCAATATCAgCTgg3'
```

The EGFP-1 and -2 64-mers target the nucleotides encoding for amino acids 22-28 of EGFP.

```
EGFP-1 (64-mer):
                                                   (SEQ ID NO: 5)
5'gATCCCgACgTAAACggCCACAAgTTTCAAgAgAACTTgTggCCgTT TACgTCTTTTTTggAAA3'

EGFP-2 (64-mer):
                                                   (SEQ ID NO: 6)
5'AgCTTTTCCAAAAAAgACgTAAACggCCACAAgTTCTCTTgAAACTT gTggCCgTTTACgTCgg3'
```

Transkingdom RNA Interference Plasmid Construction:

The engineered plasmid pT7RNAi-Hly-Inv, TRIP was constructed from pGB2Ωinv-hly (Milligan et al., *Nucleic Acids Res.* 15, 8783 (1987)) and pBlueScript II KS(+). Oligonucleotides containing multiple cloning site (MCS), T7 promoter, enhancer and terminator (synthesized from Qiagen) were ligated into blunted BssHII sites of KSII(+), and β-catenin hairpin oligos were inserted into BamHI and SalI sites of MCS to generate plasmid pT7RNAi. PstI fragments containing the inv locus of pGB2Ωinv-hly were inserted into PstI site of KSII(+). Using pGB2Ωinv-hly as template, H1yA gene was amplified by PCR (Pfx DNA polymerase, Invitrogen Inc.) with primers, hly-1: 5'-CCCTC-CTTTGATTAGTATATTCCTATCTTA-3' (SEQ ID NO:7) and hly-2: 5'-AAGCTTTTAAATCAG-CAGGGGTCTTTTTGG-3' (SEQ ID NO:8), and were cloned into EcoRV site of KSII(+)/Inv. Hly-Inv fragment was excised with BamHI and SalI. After blunting, it was ligated into EcoRV site incorporated within T7 terminator of pT7RNAi Bacteria:

The auxotrophic *Salmonella typhimurium* aroA 7207 (*S. typhimurium* 2337-65 derivative hisG46, DEL407[aroA544::Tn10(Tc-s)] used as the plasmid carrier in this study was kindly provided by Prof. BAD Stocker, Stanford University, CA. *Escherichia coli* XL-1 Blue was used to maintain the plasmids (Strategene).

Transformation of SL 7207 was achieved using an adapted electroporation protocol (1). Competent SL7207 and 1 µg plasmid were incubated on ice in a chilled 0.2 cm electroporation cuvette for 5 min. A 2.5 kV, 25 µF, 200Ω impulse was applied using a BioRad Genepulser. 1 mL of prewarmed SOC medium was added and bacteria were allowed to recover for 1 hr at 37° C. with 225 RPM shaking before plating on selective agar plates. Presence of the plasmids was confirmed using minipreparation after alcalinic lysis and separation on 0.7% agarose gel.

For in vitro experiments, SL 7202 were grown overnight at 37° C. in Luria Broth (LB) supplemented with 100 µg/mL Ampicillin (for SL-siRAS, SL-siGFP and SL-siCAT) without shaking. The next morning, bacteria were grown in fresh medium after 1% inoculation from the overnight culture until reaching an $OD_{600}$ of 0.4-0.6. Bacteria were centrifuged (3500 RPM, 4° C.) washed once in phosphate-buffered saline (PBS) and resuspended in PBS at the desired concentrations. For all determinations of bacterial number and concentration, the bacterial density was measured spectrometrically and calculated according to the formula $c=OD_{600}*8\times10^8/mL$.

For animal experiments, SL 7207 were grown in Brain Heart Infusion Broth (Sigma) in a stable culture overnight supplemented with the appropriate antibiotics where required. Bacteria were washed and resuspended in PBS at a concentration of $2.5\times10^{10}$/mL. Serial dilutions were done and plated on selective agar at several times during the experiment to verify the actual number of bacteria administered.

Plasmids were also transformed into BL21DE3 strain (Gene Therapy Systems) according to the manufacturer instructions. Bacteria were grown at 37° C. in Brain-Heart- Infusion-broth with addition of 100 µg/ml Ampicillin. Bacteria numbers were calculated using $OD_{600}$ measurement. For cell infection, overnight cultures were inoculated into fresh medium for another 2 h growth.

Cell Culture:

A human colon cancer cell line (SW 480) was used herein. It carries a mutation of APC protein resulting in increased basal levels of β-catenin. A stably GFP-expressing cell line derived from yolk sac epithelium, CRL 2583 (ATCC, Rockville, Md.) was used for GFP-knockdown experiments. CRL 2583 was maintained in 200 µg/mL G418 until 30 min before bacterial infection. SW 480 were grown in RPMI-1640 supplemented with 10% fetal bovine serum. CRL 2583 were grown in high glucose, high $NaHCO_3$ DMEM supplemented with 15% FBS as recommended by the supplier. All growth media were routinely supplemented with antibiotics: 100 U/ml penicillin G, 10 µg/ml streptomycin, 2.5 µg/ml amphotericin (all media and additives purchased from Sigma, St. Louis).

For direct transfection of plasmids, 500,000 cells were seeded into 6 cm petri dishes and allowed to grow overnight before they were transfected using a standard CaP-coprecipitation protocol.

Briefly, 15 µg plasmid-DNA are mixed in 500 µL reaction mix (2×HEPES buffer, 60 µL CaP) and dropped to the cells in fresh medium without FBS. Precipitation was allowed to continue for 9 hrs before precipitates were washed away. Cells were harvested at different time points (36, 48, 60, 72, and 96 hrs).

For standard bacterial infection assays, 500,000 cells were seeded into 6 cm petri dishes and were allowed to attach overnight. 30 min prior to addition of the bacteria, the growth medium was replaced with fresh medium without antibiotics and fetal bovine serum. SL 7207-siRAS, -siCAT, -siGFP were added in 500 µL PBS to reach the designated multiplicity of infection (MOI) of 100, 500 or 1000 and infection was carried out in a standard incubator with 37° C., 5% $CO_2$. By the end of the indicated infection period, plates were washed once with 4 ml of serum-free RPMI medium and 3 times with 4 ml PBS, then 5 ml of fresh complete RPMI medium containing 100 µg/mL of ampicillin and 150 µg/mL of gentamycin were added. Twenty-four hours later, tetracycline was added to final concentration of 15 µg/mL. At indicated different time points (24-96 h) after bacterial invasion, cells were harvested for western blot or flow cytometry.

For staining of intracellular bacteria, cells were grown on Lab-Tek II Chamber Slides (Nalgene Nunc, USA). After bacterial invasion as described above, cells were washed with PBS and fixed in 1% paraformaldeyde for 10 min. Acridin Orange (Sigma) solution (0.01%) was added for 45 sec, then washed with PBS. Crystal Violet stain (Sigma) was applied for 45 sec, then washed with PBS. Coverslips were mounted using PERMOUNT™ mounting medium and invasion was assessed using confocal microscopy.

MTT Assay:

After treatment with SL7207-siRAS and/or SL7207-siCAT, cells were trypsinized (24 h or 48 h later), diluted and seeded into 96-well plate at a concentration of 5000 cells/well. Cells were then allowed to grow for up to 4 days. At the desired incubation time point, medium was removed and 100 µl of MTT solution (5 mg/mL) was added to each well. After an incubation period of 4 h, MTT solution was drained away and cells were lysed by adding 100 µL of solubilization reagent (Isopropanol:1N HCl:10% SDS 43:2:5) to each well. The resulting signal of the dark blue formazan-product was photometrically determined at 570 nm wavelength. The amount of color formation is dependent on the number of surviving cells per well.

Colony Formation Test:

After treatment with SL7207-siRAS and/or SL7207-siCAT, cells were trypsinized (24 h post-transfection), diluted and seeded into 6-well MTP at a concentration of 750 cells/well. Cells were kept growing for two more weeks to let them form visible colonies. Two weeks later, medium was removed and 1 ml of Giemsa stain (7.415 g/L) were added to each well. After 10-min incubation at 37° C., Giemsa stain was drained away and cells washed with PBS. Groups of more than eight cells were counted as positive colonies.

Western Blot:

Cells were washed with chilled PBS, scraped off and lysed in lysis buffer (50 mM HEPES pH 7.5, 150 mM NaCl, 1 mM EDTA, 2.5 mM EGTA, 1% NP-40, 1 mM DTT) containing 0.1% protease inhibitor mix (Sigma). 20 µg of protein were separated using 11% SDS-Page Gel and transferred to a 0.4 µm PVDF membrane (Schleicher and Schuell). The membrane was blocked using 5% milk and incubated for 1 hr with specific antibodies at the indicated concentrations: Living Colors® antibody (Clontech)-1:500, β-catenin antibody (Santa Cruz)-1:500, k-Ras antibody (Santa Cruz)-1:300 and β-actin (Santa Cruz) 1:500. Each was followed by incubation with horseradish-peroxidase conjugated anti-rabbit or anti-goat secondary antibodies (Santa Cruz)-1:1000-1:2000. Bands were detected using ECL® chemoluminescence detection (Amersham).

Flow Cytometry:

For flow cytometry, cells were trypsinized for 3 min, resuspended in fresh medium and washed in PBS. After centrifugation, cells were fixed for 10 min in 1% paraformaldehyde/PBS at 4° C. Flow cytometry was performed using FACScan (Becton Dickinson), data analysis was done using CellQuest® software.

Animal Techniques:

Six to eight week old female GFP+ transgenic mice (CgTg5Nagy) were obtained from Jackson laboratories. They were housed in the BIDMC animal research facility with ad libitum access to standard rodent diet and drinking water. Treatment was initiated at ten weeks of age. For the iv treatment protocol, four doses of $10^6$ cfu SL-siRAS or SL-siGFP dissolved in 50 µL PBS were injected into the tail vein on alternating days. Mice were weighed daily and monitored for signs of disease.

Mice were sacrificed one day after the final treatment at which time tissue samples were taken for histochemistry and flow cytometric analysis. Tissues were paraffin embedded and sectioned in 6 µm steps for histochemistry and fluorescence microscopy. For flow cytometry, hepatocyte and splenocyte suspensions were prepared through the use of cell strainers (Falcon). Organ suspensions were fixed in 4% formalin and flow cytometry was performed using FACScan (Becton Dickinson), data analysis was done using CellQuest® software.

For the Xenograft cancer model, female BALB/c nude mice (Charles River Laboratories) were randomized into two groups (n=6). Three weeks before treatment, $1\times10^7$ of SW480 cells were implanted subcutaneously. Treatments were initiated when the tumors reached about 10 mm in diameter. The treatment group was injected through tail vein with $1\times10^8$ cfu of E. coli expressing shRNA against β-catenin in PBS. The control group was similarly treated except that the E. coli contains the TRIP vector without shRNA insert. The treatment was carried out every 5 days for a total of three treatments. Mice were sacrificed 5 days after the last treatment. Tissues were frozen and fixed for analysis of β-catenin mRNA level by real-time PCR and β-catenin protein level by immunohistochemistry.

For in vivo silencing experiments, female C57/BL6 mice (Charles River Laboratories) were randomly divided into two groups. The treatment group was administered orally with $5 \times 10^{10}$ cfu E. coli expressing shRNA against β-catenin in 200 μL phosphate-buffered saline (PBS). The control group was similarly treated except that the E. coli contains the TRIP vector without the shRNA insert. Two independent experiments were performed with 6 and 5 mice per group used, respectively. The treatment was carried out daily for 5 days per week for a total of 4 weeks. Mice were sacrificed 2 days after the last treatment, and tissues were paraffin-embedded.

Immunohistochemistry

Immunostaining was performed on 6 μm tissue sections using Vectastain Elite ABC avidin-biotin staining kit (Vector laboratories, Burlingame, Calif.) according to the instructions by the manufacturer. Slides were deparaffinized and rehydrated using a standard protocol. For antigen retrieval, slides were heated by microwave in 5% urea for 5 min. Unspecific binding sites were blocked with 1% bovine serum albumin for 10 min and endogenous peroxidase activity was suppressed by treatment with 3% $H_2O_2$ in methanol for 10 min. Sections were exposed to primary antibody LIVING COLORS™ rabbit polyclonal antibody (Clontech) at 1:500 dilution overnight at 4° C. The chromogen used was 3,3'Di-amino-enzidine (DAB) (Vector), counterstaining was done with hematoxyline.

Interferon Response Detection:

SW480 cells were treated for 2 h with E. coli transformed with the TRIP encoding shRNA against human β-catenin or mutant k-Ras at MOI of 1:1000. Untreated cells were used as control. Cells were harvested at 24, 48 and 72 h. The expression levels of OAS1, OAS2, MX1, ISGF3γ and IFITM1 genes were determined by RT-PCR using the Interferon Response Detection Kit (SBI System Biosciences, CA).

Example 1

Knock Down of Green Fluorescent Protein Using Bacteria Mediated Gene Silencing In Vitro and In Vivo In the following experiments, an attenuated strain of Salmonella typhimurium (SL 7207, obtained from BAD Stocker, Stanford University) was used. To prove that the concept is useful as a general approach, we did confirmation experiments also with another attenuated strain of Salmonella typhimurium (VNP 70009, obtained from VION Pharmaceuticals, New Haven) and an invasive and attenuated strain of E. coli (BM 2710, obtained from P. Courvalin, Institut Pasteur, Paris).

Silencing plasmids were designed based on a commercially available plasmid (pSilencer, Ambion) to knock down the target genes GFP, β-catenin and oncogenic k-Ras (V12G). These plasmids were transformed into SL 7207 by electroporation and positive clones were verified by growth on selective agar and DNA preparation.

For in vitro use, knockdown of GFP expression was demonstrated using the stable GFP+ cell line CRL 2598 (ATCC, Rockland, Va.). Knockdown of oncogenic k-Ras (V12G) and β-catenin was demonstrated using the colon cancer cell line SW 480 and the pancreatic cancer cell line CAPAN-1.

A system of bacterial delivery using an invasive bacterial strain, S. typhimurium, was developed with a commercially available eukaryotic transcription plasmid, pSilencer (Ambion). The S. typhimurium strain SL 7207 (kindly provided by B. Stocker, Stanford University) is attenuated through an auxotrophy in the synthesis pathway for aromatic amino acids, and dies quickly after invasion into a target cell due to lack of nutrients. This strain has been used successfully for delivery of DNA in vitro and in mouse models, mainly with the purpose of DNA vaccination.

Figure 2A:
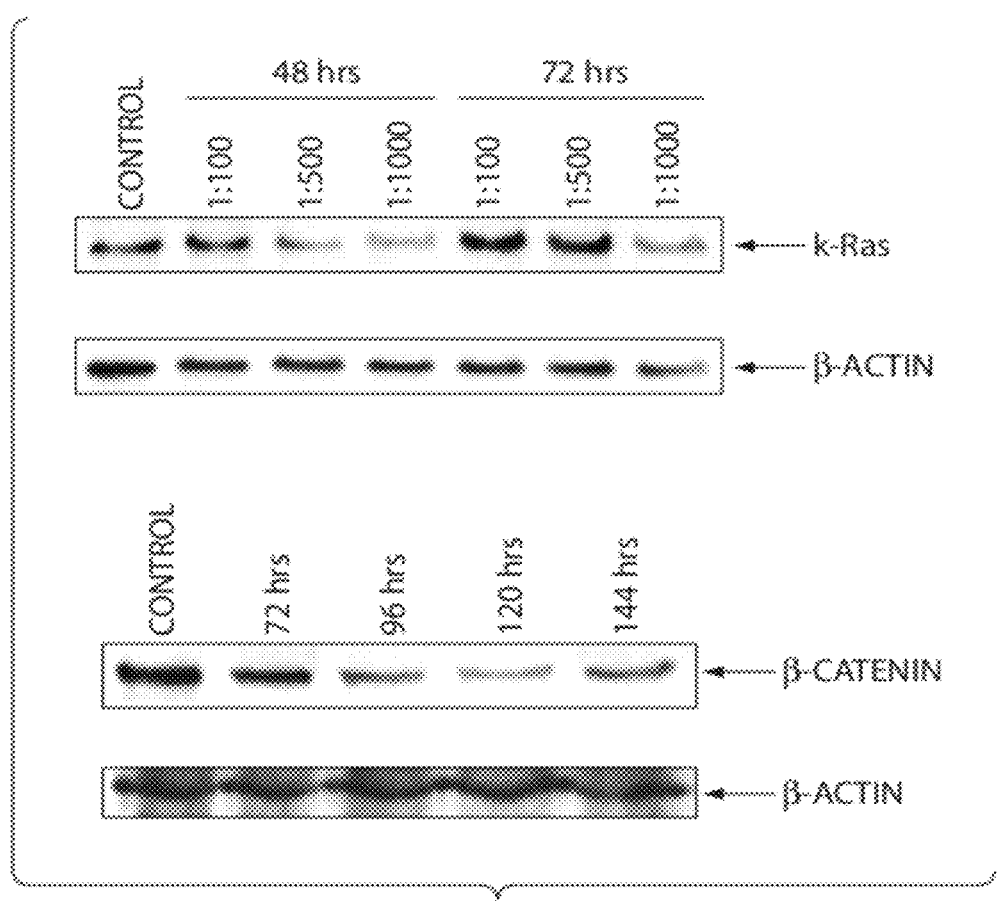
FIG. 2A shows Western blots of k-Ras and β-catenin in SW 480 cells.
Figures 1, 2B:
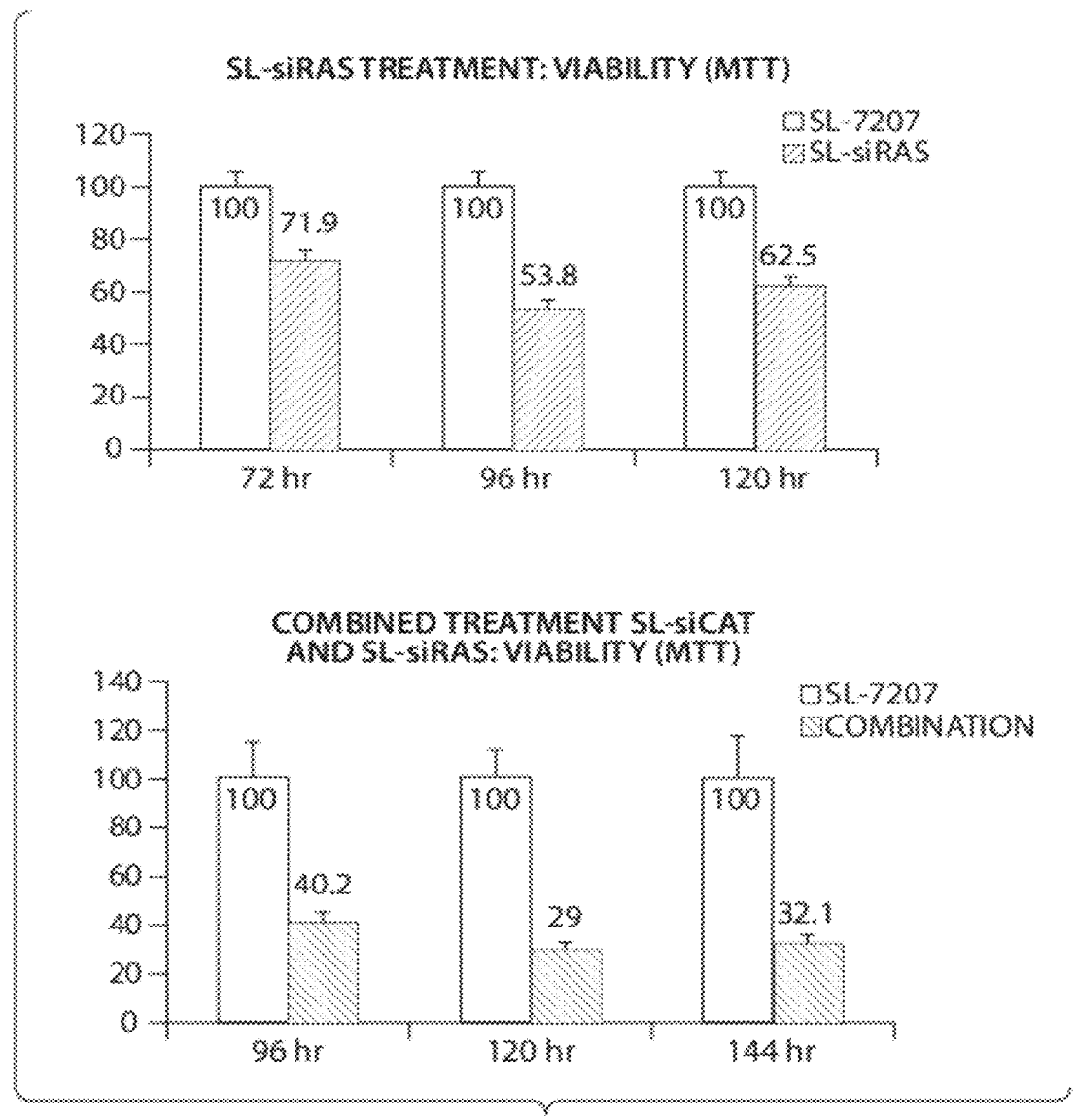
FIG. 2B is a series of bar charts showing viability of SW 480 cells under various treatment regimens.

To verify bacterial entry into epithelial cells, an invasion assay was performed. SW 480 cells were infected for 2 hrs with SL-siRAS followed by 2 hrs of treatment with gentamycin. Acridin orange/crystal violet staining revealed good invasion efficiency. 90% of the SW 480 cells harbored viable SL 7207 bacteria. The average number of intracellular bacteria was 6 (range, 2-8) (FIG. 1). (Micrograph A1 is the transmission image. Micrograph A2 is the fluorescent image. Micrograph A3 is the merged image.) The number of viable intracellular bacteria reduced quickly over time. After 24 hrs and 48 hrs, only 10% and 3% of cells were found to still contain bacteria.

In the next experiment, The effective reduction of GFP expression in the GFP+ cell line was demonstrated. Successful knockdown of oncogenes k-Ras and β-catenin was confirmed using Western blot and RT-PCR. Oncogene knockdown resulted in growth retardation and decreased tumor formation in a xenograft animal model.

Figure 1B:
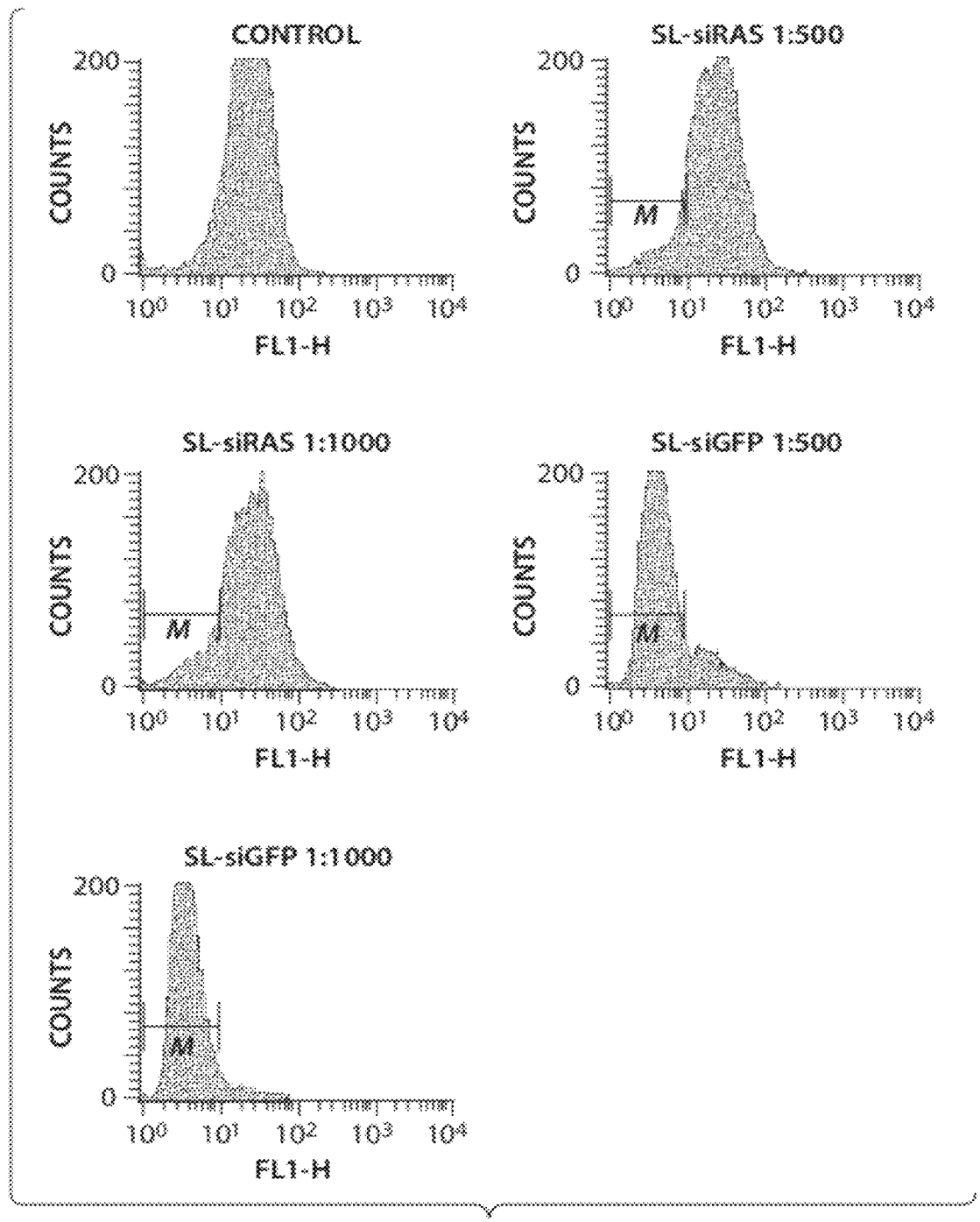
FIG. 1B shows FACS analysis of a knockdown of green fluorescent protein expression in CRL 2583 cells.
Figure 1C:
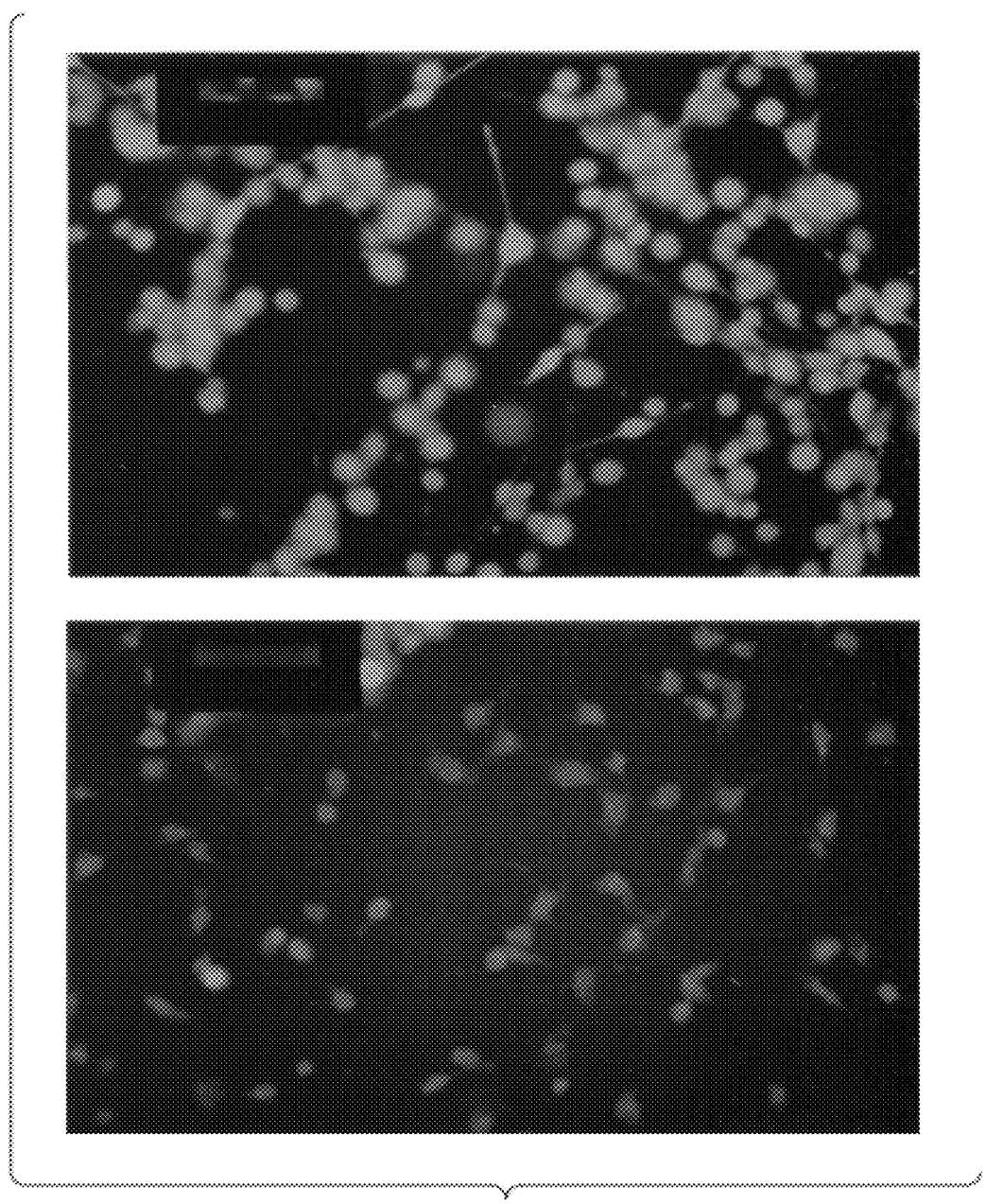
FIG. 1C shows micrographs showing loss of fluorescence in CRL 2583 cells.

Cells stably expressing GFP(CRL 2583) were infected with SL7207 carrying pSilencer2.0 including a sequence to silence GFP mRNA (SL-siGFP). (See above). After 48 hrs, cells treated with SL-siGFP showed a marked decrease in GFP expression as compared to cells treated with SL-siRAS and untreated control (FIGS. 1B and 1C). Treatment with SL-siGFP led to loss of GFP signal in a manner dependent on the multiplicity of infection (MOI) applied. In untreated cells, only 4.3% display low or absent fluorescence. In SL-siGFP treated cells, this fraction increased to 78.1% (treated with MOI 1:500) and 92.3% (MOI 1:1000). Control treatment with SL-siRAS lead to a slight loss of fluorescence (7.5% at MOI 1:500 and 8.4% at MOI 1:1000). This is also shown in the fluorescence microscope photograph in FIG. 1C. The top micrograph is (200×) of SL-siRAS and the bottom of SL-siGFP (below) treated CRL 2583 cells. This finding was confirmed using flow cytometry.

In a series of animal experiments with stably GFP-expressing mice, we were able to demonstrate knockdown of GFP expression in the liver and in the colon (in both organs approx 50% reduction of GFP expression) after oral and intravenous application of SL 7207 carrying the GFP-silencing plasmid.

In animal experiments, S. typhimurium was used to achieve gene silencing in a transgenic mouse model (GFP+). Using this method, silencing of the transgene in the animal experiment is demonstrated at mRNA level as well as on protein levels and tissue sections of various organs (liver, gastrointestinal tract) with limited toxicity.

Example 2

Knock Down of k-Ras and β-Catenin Using Bacteria Mediated Gene Silencing

Next, BMGS was applied to knock down a specific disease-related gene. The specific oncogenic point mutation in the k-Ras gene, k-Ras$^{V12G}$, which is present in the human colon carcinoma cell line, SW 480 was targeted.

After construction of the silencing plasmids and before they were electroporated into the attenuated SL7207, their activity was tested by transfecting them into SW 480 cells using CaP coprecipitation.

Figure 4A:
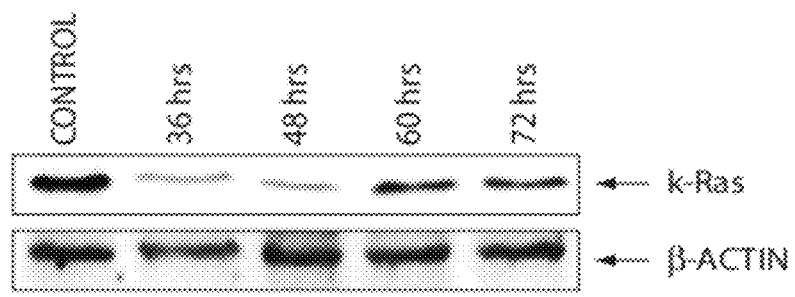
FIG. 4 shows Western blots of k-Ras and β-catenin from SW 480 cells transfected with silencer plasmid.

Western blot (FIG. 4A) shows efficient knockdown of k-Ras using the pSilencer-kras (V12G) insert at 36 h and 48 h posttransfection. At later time points, the protein expression recovers, which is due to outgrowth of transfected clones which have a growth disadvantage versus non transfected clones in which the oncogenic k-Ras would still drive replication. When BMGS with SL7207 as a carrier was used to mediate the knockdown, k-Ras levels were decreased at MOI of 1:500 and 1:1000. Using BMGS, knockdown of the k-Ras protein was observed with similar efficiency compared to direct transfection of the silencer plasmid using calcium-phosphate coprecipitation, although the onset of knockdown was slightly delayed by 12 hrs. (FIG. 4A). With an MOI of 1:1000, the result can be observed for a longer time (up to 72 hrs) (FIG. 2A).

Figure 4B:
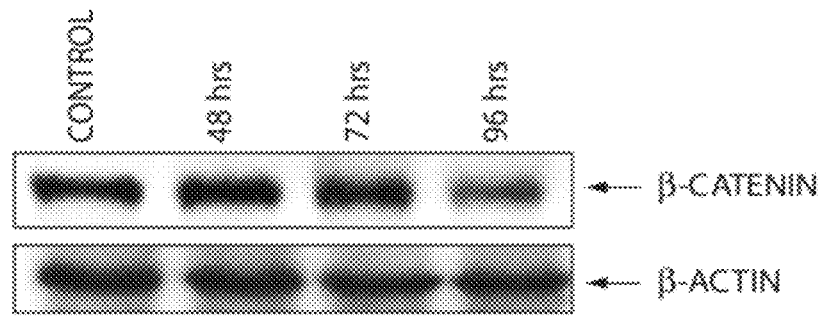

The Western blot for β-catenin (FIG. 4B) shows delayed knockdown after transfection, with a maximum effect seen at 96 hrs post transfection. It is assumed that this delay is caused by the survival time of SL 7207 intracellularly before the plasmid is liberated (FIG. 2A).

After treatment with SL-siRAS and resulting knockdown of the oncogenic k-Ras (V12G), SW 480 cells displayed significantly reduced viability and colony formation ability (FIG. 2B). Cells were coincubated with equal amounts (2.5×$10^8$) of SL-siRAS and SL-siCAT bacteria. Control cells were treated with untransformed SL 207. 48 hrs after transfection, cells were seeded in 96 well plates for MTT test and 6 well plates for colony formation assays. At 120 hrs after treatment, viability, as assessed by MTT assay, was reduced to 62.5% after SL-siRAS treatment and 51% after SL-siCAT treatment. Combined treatment further reduced viability to 29% of control treated cells. SL-siRAS treatment and SL-siCAT treatment reduced the ability of SW 480 to form colonies by 37.7% and 50%, respectively. Combined treatment lead to 63.3% reduction.

Figures 2, 2B:
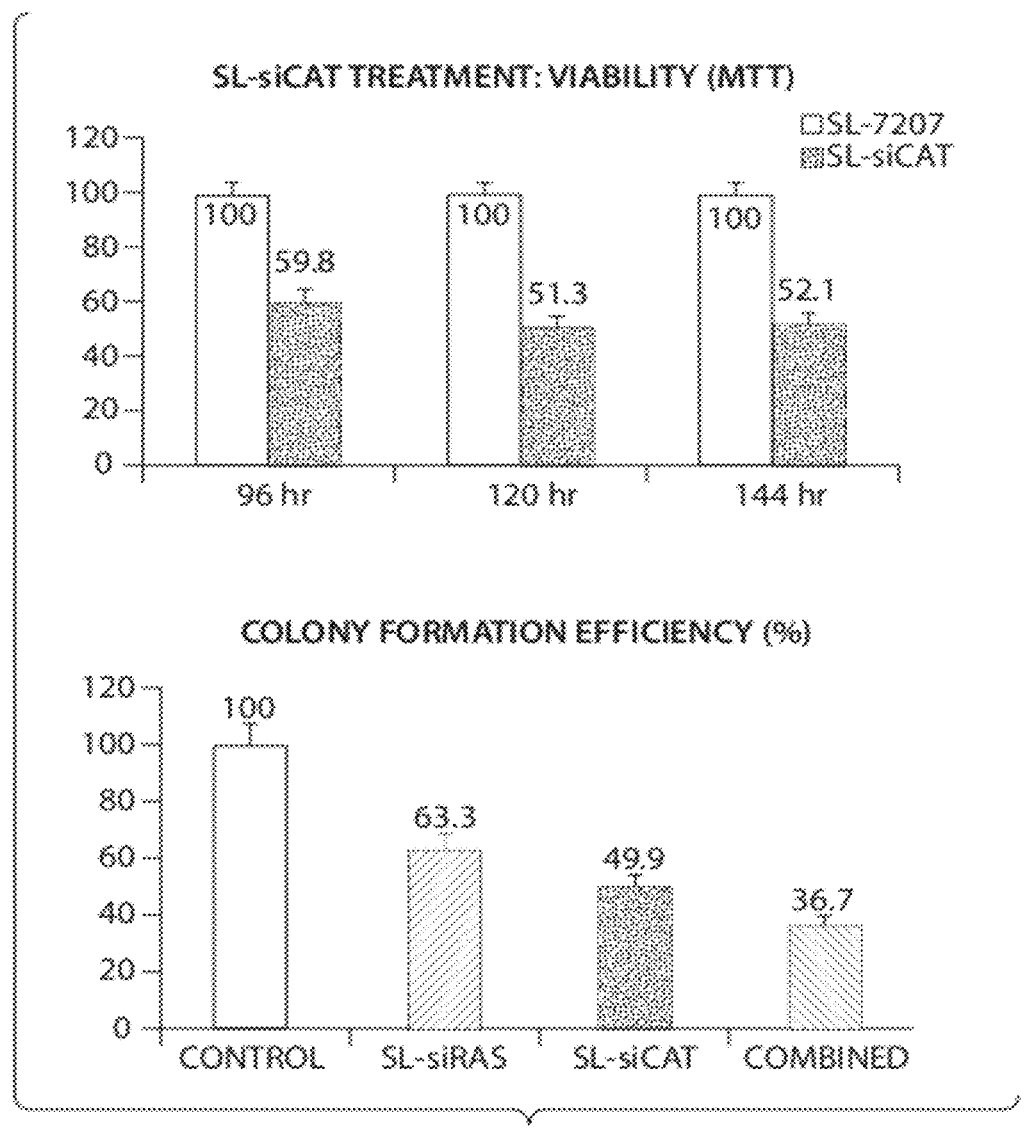
Figure 2C:
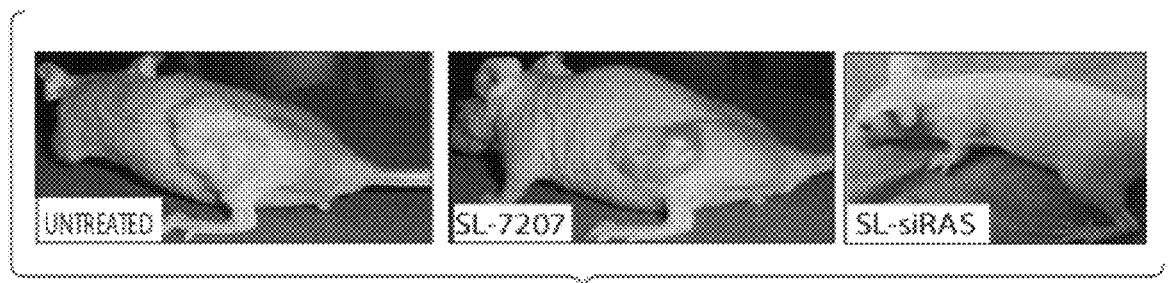
FIG. 2C shows photographs of tumorigenicity in nude mice injected with SW 480 cells transfected with various siRNAs.

Further, treatment with SL-RAS completely inhibited the tumor formation ability of SW 480 cells when injected subcutaneously into nude mice, while treatment with empty SL 7207 did not influence their ability to form tumors (FIG. 2C). SW 480 cells (untreated, treated with SL 7207 or SL-siRAS) were subcutaneously injected into nude mice (4×$10^6$ cells, n=4 animals per group). Pretreatment with SL-siRAS completely abolished the ability to form tumors (no tumors visible in any of the four animals, day 40) (FIG. 2C).

To test whether this approach can be employed universally, another cancer-related gene, β-catenin was targeted (FIG. 2A). Basal levels of β-catenin are high in SW 480 cells, due to a mutated APC-gene, but can be reduced through treatment with hairpin siRNA after pSilencer(siCAT) transfection (FIG. 2A). After treatment with SL 7207 carrying pSilencer with the β-catenin construct (SL-siCAT), significant knockdown of β-catenin expression was achieved which resulted in decreased viability and colony formation ability (FIG. 2A). β-catenin was knocked down from 96 hr, but recovered from 144 hr.

Example 3

In Vivo Bacterial Mediated Gene Silencing

The method of bacterial mediation of RNAi offers the possibility of selectively targeting more than one gene at a time which might allow for increased efficiency for future applications, e.g. anticancer treatment through interference with multiple oncogenic pathways. To test the feasibility of such an approach, both the mutated k-Ras oncogene and β-catenin were targeted simultaneously. After simultaneous treatment with SL-siRAS and SL-siCAT, knockdown of both genes was observed at the protein level and resulted in further decreased viability and colony formation ability (FIG. 2). These findings demonstrate that the proposed concept of bacterial mediated gene silencing can be successfully used in vitro for different target genes and in different cell lines.

A mouse model was chosen to test whether this approach can be used to silence target genes in vivo. CgTg5-Nagy mice express high levels of GFP in all tissues. 14 mice were randomly assigned to receive four doses of $10^6$ cfu of either SL-siGFP or SL-siRAS i.v. on alternating days (seven animals per group). This treatment was well tolerated with no weight loss or clinically apparent signs of disease. All mice were sacrificed one day after the last treatment.

Figure 3A:
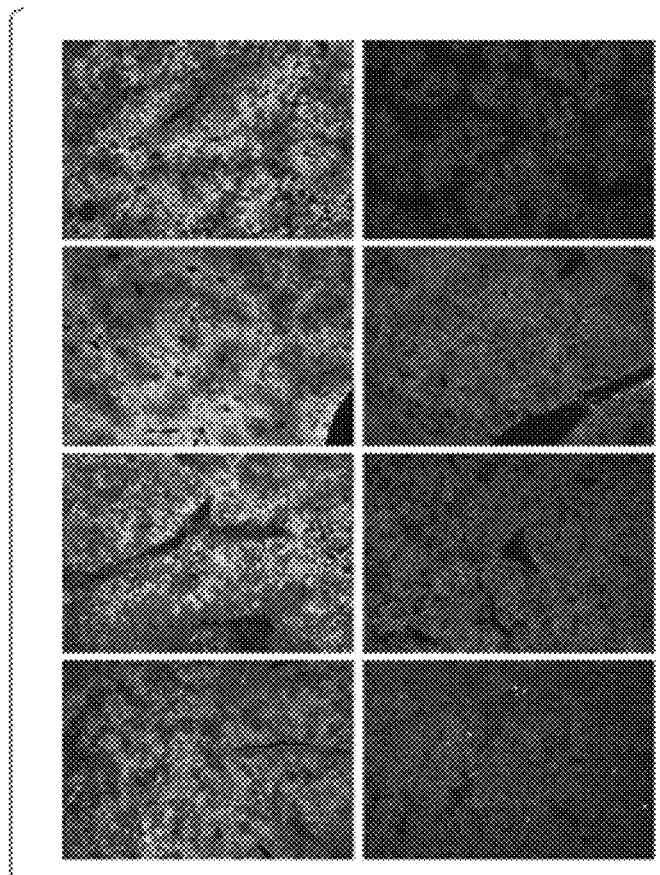
FIG. 3A shows micrographs of transgenic mouse liver sections.
Figure 5:
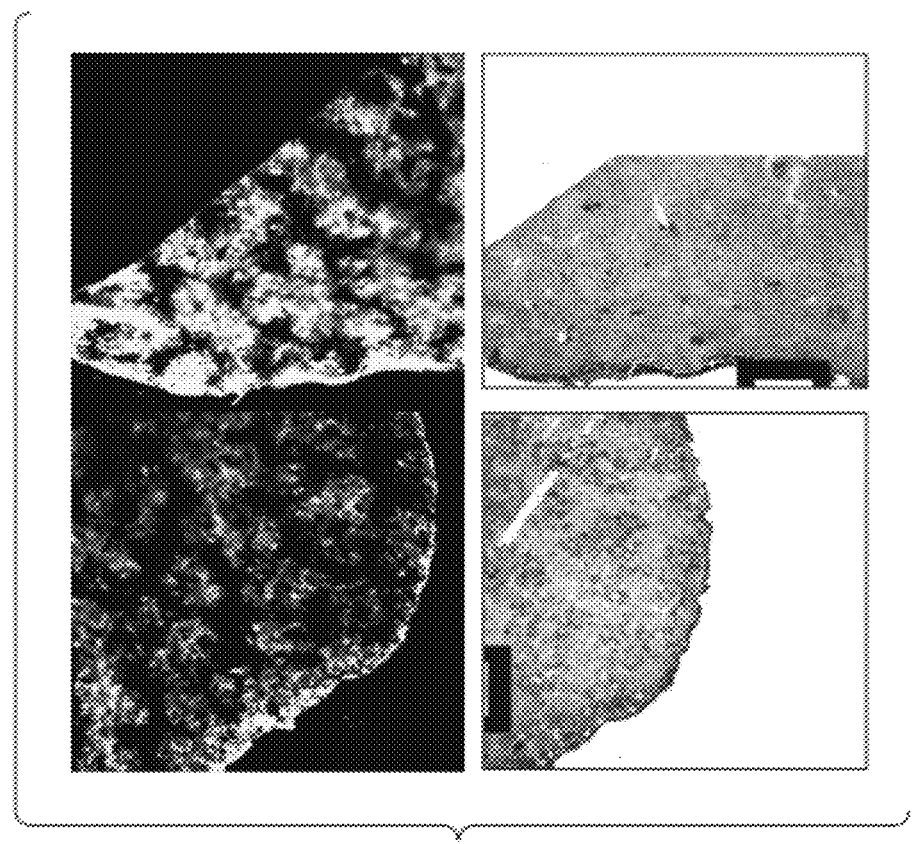
FIG. 5 shows micrographs of histochemical staining of liver sections of mice shoing changes in GFP expression levels.

Liver tissue slides were assessed by fluorescence microscopy and immunohistochemistry with GFP antibody. (FIG. 3A). Intravenous treatment with SL-siGFP led to decrease of fluorescence in the liver sections of the treated animals compared with SL-siRAS treated control animals. Histochemistry staining, with anti-GFP antibody, verified that changes in fluorescence were caused by a reduction in GFP and not caused by changes in background fluorescence levels. (FIG. 5) To verify that reductions in fluorescence in the liver sections of treated mice are really caused by changes in GFP expression levels and not due to changes in background fluorescence, tissue slides were stained with GFP specific antibody.

Immunohistochemical staining patterns correlate well with fluorescence microscopy images and confirm that changes in fluorescence are caused by decreased GFP expression. Fluorescence microscopy (50×) and corresponding immunohistochemistry image (50×) of liver section from control (top row) and iv treated (lower row) animal.

Figure 3B:
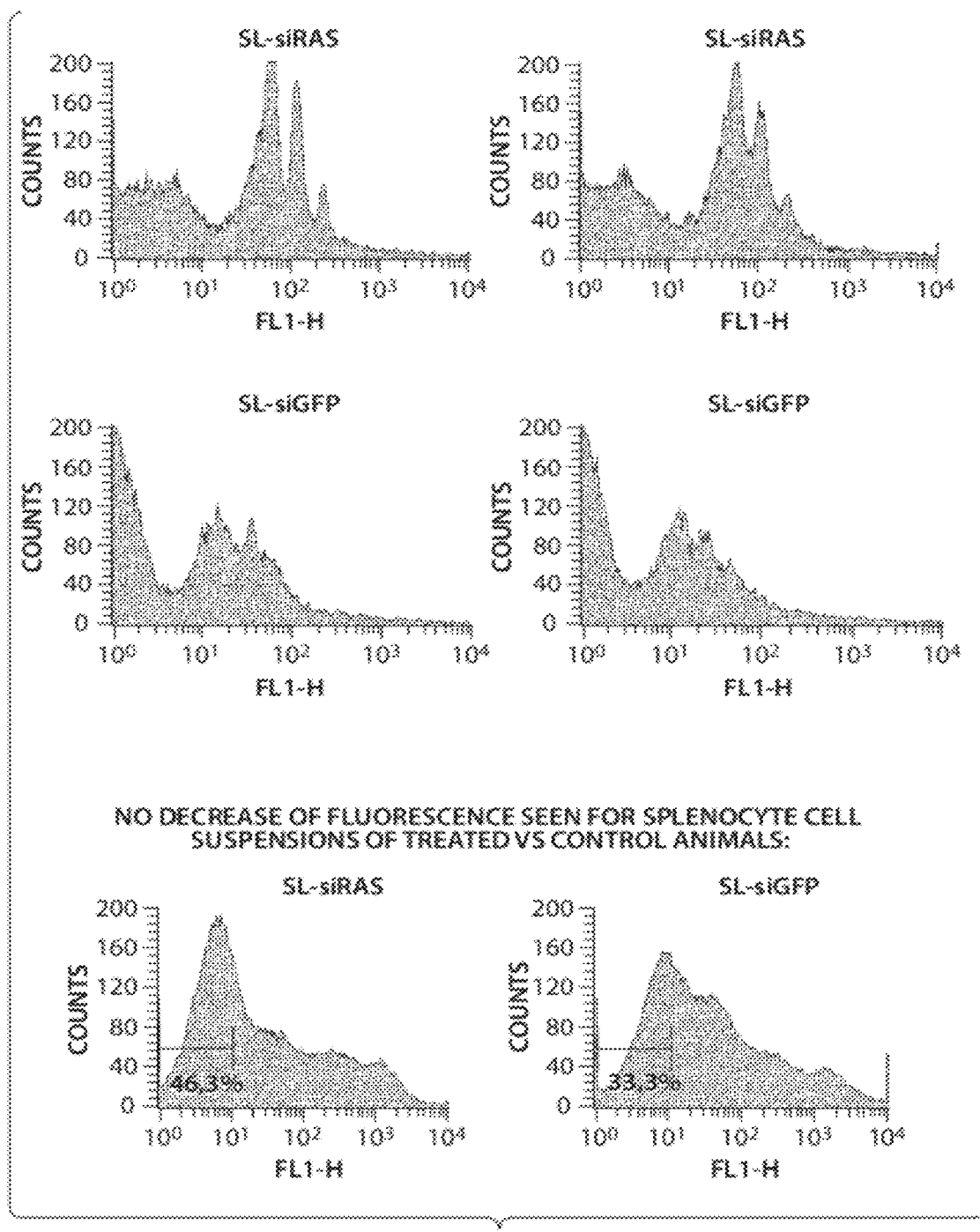
FIG. 3B shows flow cytometry measurements of hepatocyte and splenocyte suspensions.

Staining patterns correlated well with fluorescence images. Subsequent image analysis revealed reductions in the number of GFP expressing cells between 9-25% after SL-siGFP treatment. These findings were confirmed by flow cytometric analysis of single cell suspensions of hepatocytes which showed a significant decrease in the number of GFP-positive hepatocytes in SL-siGFP treated vs SL-siRAS treated animals (FIG. 3B). Flow cytometry measurements of hepatocyte and splenocyte suspensions were performed. After intravenous treatment with SL-siGFP, the number of GFP+ hepatocytes was significantly reduced compared to control treated (SL-siRAS) animals (SL-siRAS: 50.0% [45.4-53.2%], SL-siGFP: 39.9% [26.1-53.2%], p<0.05).

These results indicate that significant gene silencing can be achieved in vivo using this approach. Using iv application of attenuated *S. typhimurium* we were able to extend the in vitro findings into a mouse model and achieve significant gene silencing in the liver. Other organs might become accessible through use of different invasive bacterial strains or different routes of application. Especially professional phagocytes will be a promising target for bacteria-mediated gene silencing, as transfection efficiencies have been reported to be higher for these cells compared to cells of epithelial lineage.

Example 4

Transkingdom RNA Interference

Figure 6A:
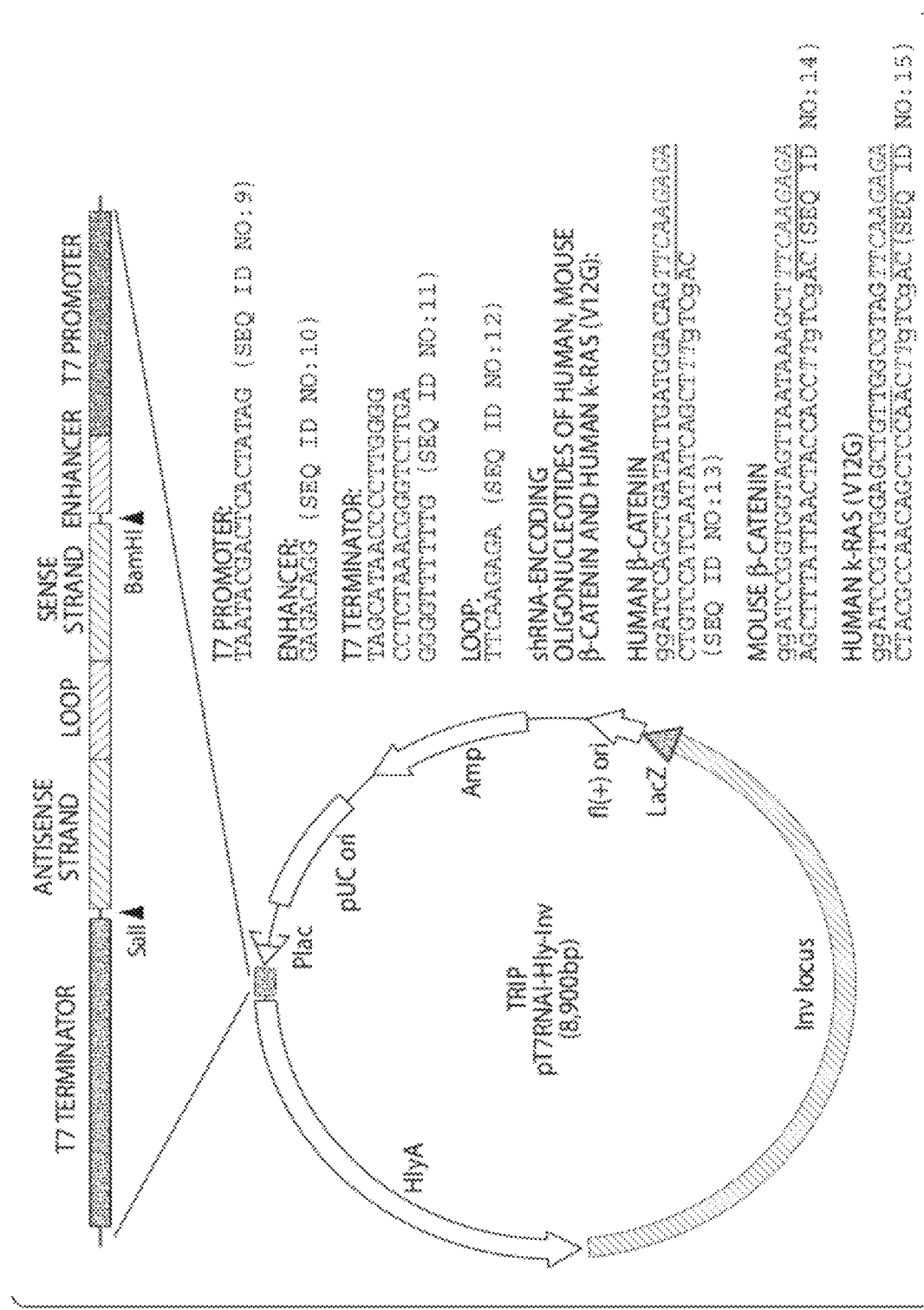
FIG. 6A is a schematic showing the Transkingdom RNA Interference Plasmid (TRIP).

The use of bacteria-mediated RNAi in higher organisms holds the potential for functional genomics in mammalian system, as previously demonstrated in *C. elegans*, and for other in vivo applications of RNAi. To investigate this possibility, the bacterial plasmid pT7RNAi-Hly-Inv, termed TRIP (transkingdom RNA interference plasmid) was constructed (FIG. 6A). In this novel plasmid construct, the expression of shRNA was directed under the bacteriophage T7 promoter (Milligan and Uhlenbeck, *Methods Enzymol.* 180, 51-62 (1989) and Milligan et al., *Nucleic Acids Res.* 15, 8783-8798 (1987), rather than a mammalian promoter or enhancer. The shRNA can only be produced by the bacterial system. The TRIP vector contains the Inv locus that encodes invasion (Isberg et al., *Cell* 50, 769-778 (1987)), which permits the non-invasive *E. coli* to enter β1-integrin-positive mammalian cells (Young et al., *J. Cell Biol.* 116, 197-207 (1992)). The TRIP vector also contains the Hly A gene that encodes listeriolysin O to permit genetic materials to escape from entry vesicles (Mathew et al., *Gene Ther.* 10, 1105-1115 (2003) and Grillot-Courvalin et al., *Nat. Biotechnol.* 16, 862-866 (1998)). TRIP constructs were introduced into a competent strain of non-pathogenic *E. coli*, BL21DE3, which contains T7 RNA polymerase to express shRNA. A TRIP against the cancer gene β-catenin was constructed as an example. Activation of the β-catenin pathway from over-expression or oncogenic mutation of β-catenin is responsible for the initiation of the vast majority of colon cancers and is involved in a variety of other cancer types (Kim et al., *Oncogene* 24, 597-604 (2005)). Despite the potential of β-catenin as a cancer therapeutic target, the β-catenin pathway has been recalcitrant to inhibition by small molecules. β-catenin is a preferred choice in proof of concept experiments for testing the potency of new a RNAi approach because it is commonly stabilized in cancer cells. TRIP can be modified to enable bacteria to express interfering RNA against various genes of interest.

Figure 6B:
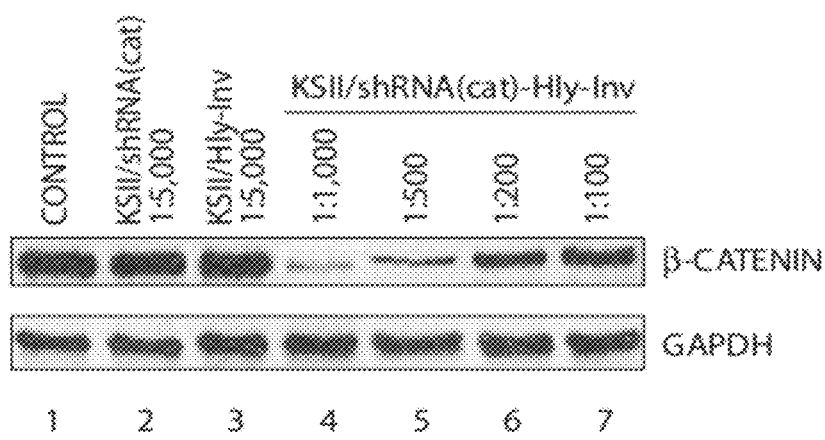
FIG. 6B is a photograph showing an immunoblot of β-catenin from SW 480 cells transfected with TRIP.
Figure 6C:
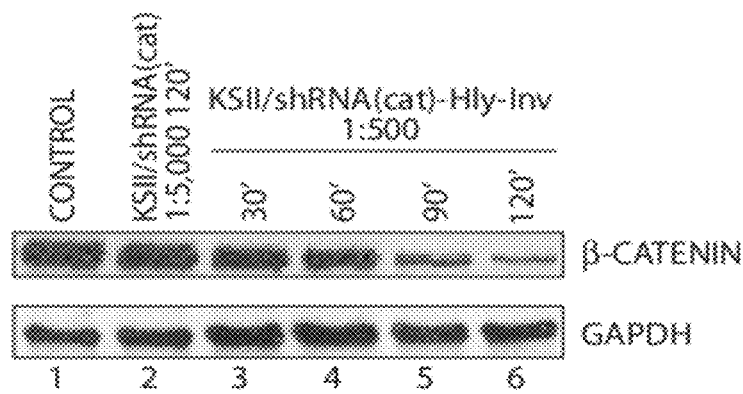
FIG. 6C is a photograph showing an immunoblot of β-catenin from SW 480 cells transfected with TRIP for exposure time from 30 to 120 minutes.
Figure 6D:
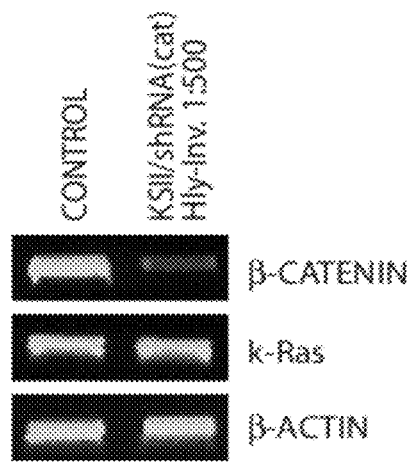
FIG. 6D shows an RT-PCR photograph of β-catenin and k-Ras mRNA from SW 480 cells transfected with TRIP.
Figure 6E:
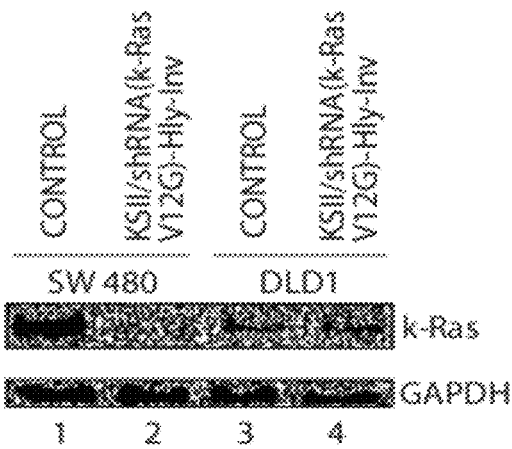
FIG. 6E is a photograph showing an immunoblot of k-Ras in SW 480 and DLD1 cells following transfection with a TRIP against mutant k-Ras (GGT→GTT at codon 12) mutant k-Ras (GGC→GAC at codon 13.
Figure 6F:
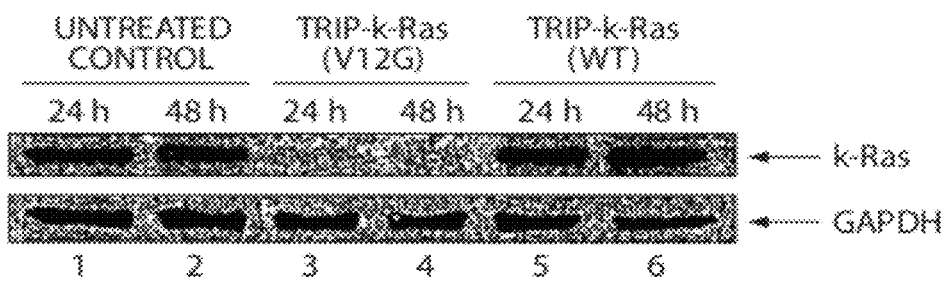
FIG. 6F is a photograph showing an immunoblot of SW 480 cells transfected with a TRIP against wild type k-Ras.

To determine if gene silencing can be achieved through this transkingdom system, human colon cancer cells (SW 480) were co-cultured in vitro with *E. coli* for 2 h (FIGS. 6B and 6D) or different time (FIG. 6C), then treated with antibiotics to remove extracellular bacteria. Cells were further cultured for 48 h before harvest for analysis of gene silencing. As shown in FIG. 6B-6D, β-catenin was potently and specifically silenced at protein and mRNA level, while β-actin, k-Ras, and glyceraldehyde-3-phosphate dehydrogenase (GAPDH) were not affected. To further test the specificity of the transkingdom RNAi, *E. coli* containing the TRIP against mutant k-Ras (GGT→GTT at codon 12) silenced k-Ras expression in SW 480 cells with the same codon 12 mutation, but not in DLD1 cells with mutation in a different codon of k-Ras (GGC→GAC at codon 13, FIG. 6E). As an shRNA control, *E. coli* containing the TRIP against wild type k-Ras exerted no gene-silencing effect on mutated k-Ras in SW 480 cells (FIG. 6F). These results show that the transkingdom RNA interference is highly gene-specific, sufficient to discriminate a point mutation.

To investigate the variables that affect the potency of gene silencing by the transkingdom system, cells were incubated for 2 h with the *E. coli* at different multiplicity of infection (MOD. As shown in FIG. 6B, the potency of gene silencing was dependent on MOI, with near complete gene silencing at a MOI of 1:1,000. To determine the effect of co-culture time on gene silencing, cells were incubated with the *E. coli* at a MOI of 1:500 for different times. As shown in FIG. 6C, gene-silencing potency increased with incubation time up to 2 h. The dependency of gene silencing on MOI and co-culture time provides controllable flexibility for gene silencing in various applications.

Figure 7A:
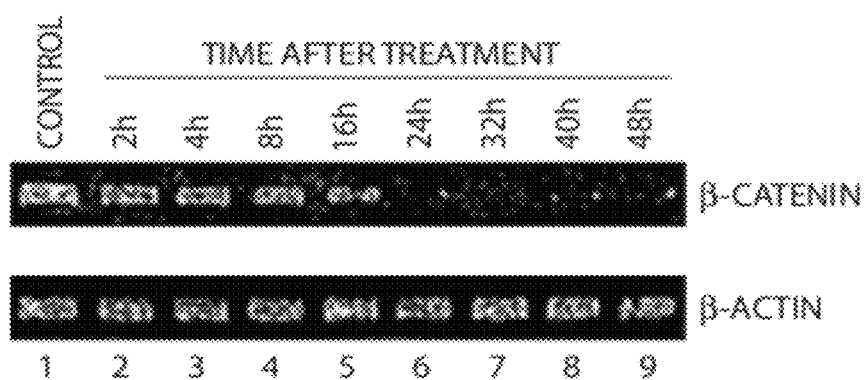
FIG. 7A is a photograph of RT-PCR showing β-catenin silencing following treatment with *E. coli* expressed shRNAs.
Figure 7B:
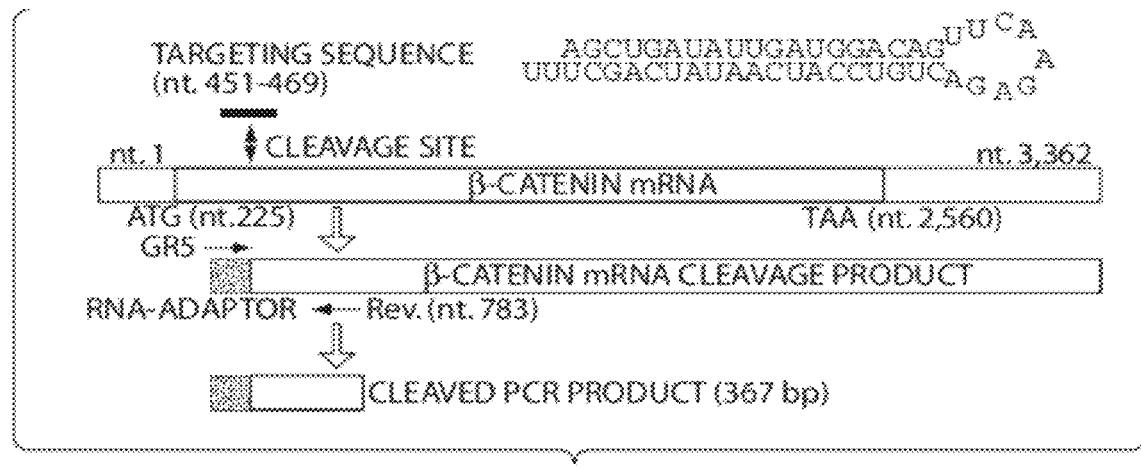
FIG. 7B is schematic showing specific cleavage sites in β-catenin.
Figure 7C:
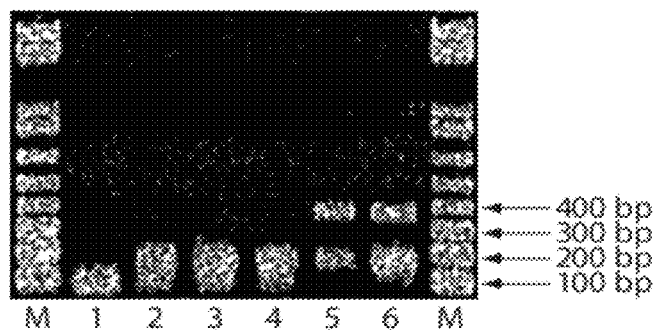
FIG. 7C is a photograph of a 5'-RACE-PCR showing specific cleavage products.

To further confirm that the β-catenin gene silencing is mediated specifically by shRNA, identification of the specific cleavage fragment of β-catenin mRNA was attempted by using 5'-RACE (rapid amplification of cDNA ends) PCR technique. A specific hallmark of RNAi-mediated gene silencing is the cleavage of β-catenin mRNA at the specific sites of the mRNA as predicted from the shRNA sequence. Based on the time course of β-catenin silencing (FIG. 7A), total RNA was isolated from SW 480 cells 8 h and 16 h after treatment with *E. coli* expressing shRNA against β-catenin to identify the cleaved fragments of mRNA. The cleaved β-catenin mRNA was found as early as 8 h after treatment with *E. coli* expressing shRNA: no fragments were detected in the control (FIGS. 7B and 7C). The sequence analysis of the cleaved intermediate of β-catenin mRNA confirms the cleavage site located within the targeting sequence. This result shows that shRNA produced by bacteria trigger specific cleavage of the β-catenin mRNA through the RNAi-mediated gene silencing.

Figure 7D:
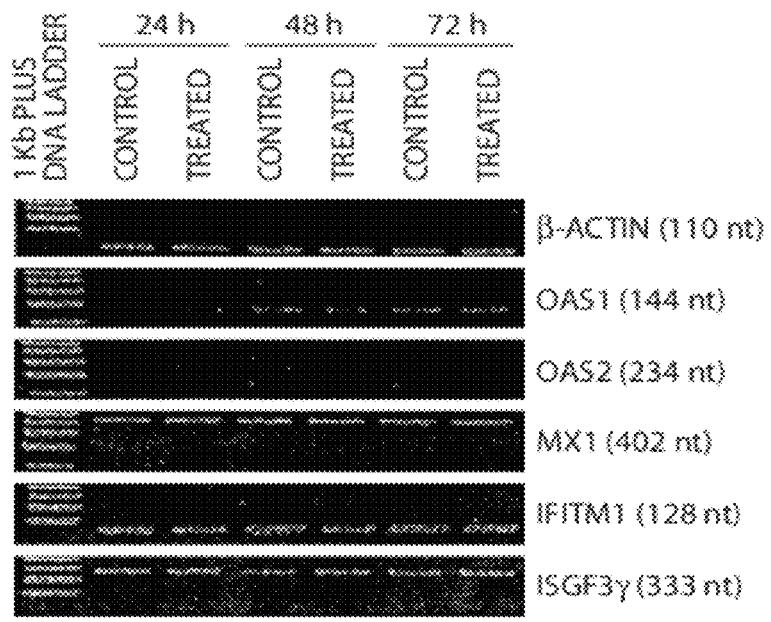
FIG. 7D is a photograph of a blot showing the mRNA expression of various genes.

Induction of interferon response has been reported as a potential challenge to the specificity of some RNAi approaches (Bridge et al., *Nat. Genet.* 34, 263-264 (2003) and Hornung et al., *Nat. Med.* 11, 263-270 (2005)). To test if the gene silencing induced by the transkingdom RNAi is associated with interferon response induction, key interferon response genes were measured. The 2',5'-oligoadenylate synthetases (OAS1 and OAS2) are important interferon-induced genes for the inhibition of cellular protein synthesis after viral infection. MX1 gene, a member of the interferon-induced myxovirus resistance protein family (MX proteins), participates in the innate host defense against RNA viruses. IFITM1, a member of the interferon-inducible transmembrane proteins, mediates the anti-proliferation activity of interferon. ISGF3γ is part of a cellular interferon receptor involved in interferon-induced transcription regulation and stimulation. These genes have been used as a standard panel for analyzing interferon response induction by interfering RNA (Interferon Response Detection Kit, SBI Systems Biosciences, CA). The mRNA of the five-interferon response genes were analyzed with semiquantitative RT-PCR. As shown in FIG. 7D, no induction of OAS1, OAS2, MX1, ISGF3γ and IFITM1 was detected following treatment with *E. coli* encoding shRNA against β-catenin. These data show that gene silencing induced by transkingdom RNAi is not associated with non-specific interferon response induction.

Figure 8A:
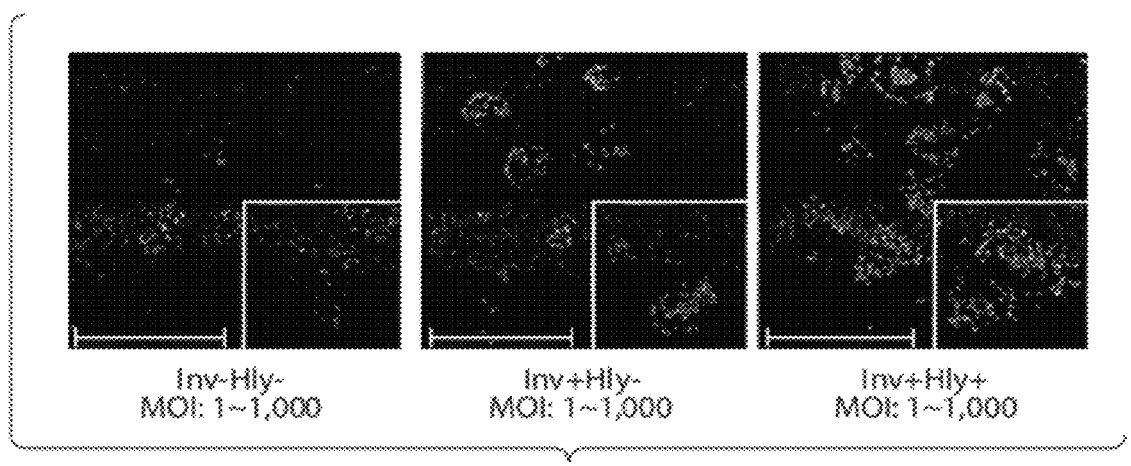
FIG. 8A is a photograph of cellular staining showing that both Inv and Hly are required for bacterial entry.
Figure 8B:
FIG. 8B is a photograph of an RNA blot showing that TRIP lacking Hly is unable to induce knockdown of a target gene.
Figure 8C:
FIG. 8C is a photograph of an RNA blot showing that both Inv and Hly are required to facilitate efficient transkingdom iRNA.

The mechanism of the transkingdom RNAi transfer was investigated. To determine if cellular entry of *E. coli* is required to induce RNAi, the gene-silencing activity of *E. coli* was compared with or without the Inv locus. The Inv encodes invasin that interacts with β1-integrin to facilitate the entry of *E. coli* into the cells. As expected, *E. coli* without Inv failed to enter cells (FIG. 8A). Surprisingly, Inv alone is not sufficient to enable *E. coli* to enter colon cancer cells (FIG. 8A), and no detectable gene silencing was observed in the absence of intracellular bacteria (FIG. 8B). The Hly A gene was introduced, which is thought to facilitate delivered genetic materials to escape from the entry vesicles (Grillot-Courvalin et al., *Nat. Biotechnol.* 16, 862-866 (1998). As expected, Hly alone failed to enable cell entrance of *E. coli*, but commensal *E. coli* with both Inv and Hly entered colon cancer cells with high efficiency (FIG. 8A). Under these conditions β-catenin was potently silenced up to 96 h (FIG. 8C). These results show that *E. coli* require both Inv and Hly to enter cells to induce transkingdom RNAi.

Figure 8D:
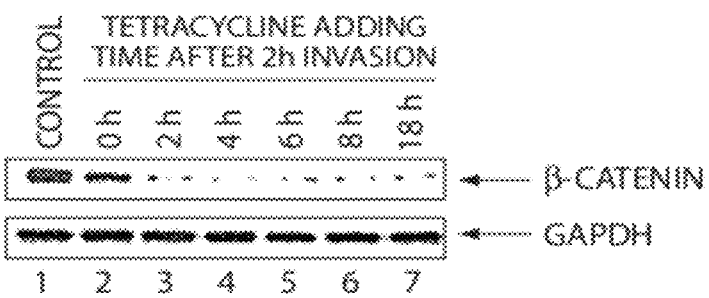
FIG. 8D is a photograph of an RNA blot showing the effect of delayed addition of tetracycline on gene silencing.
Figure 8E:
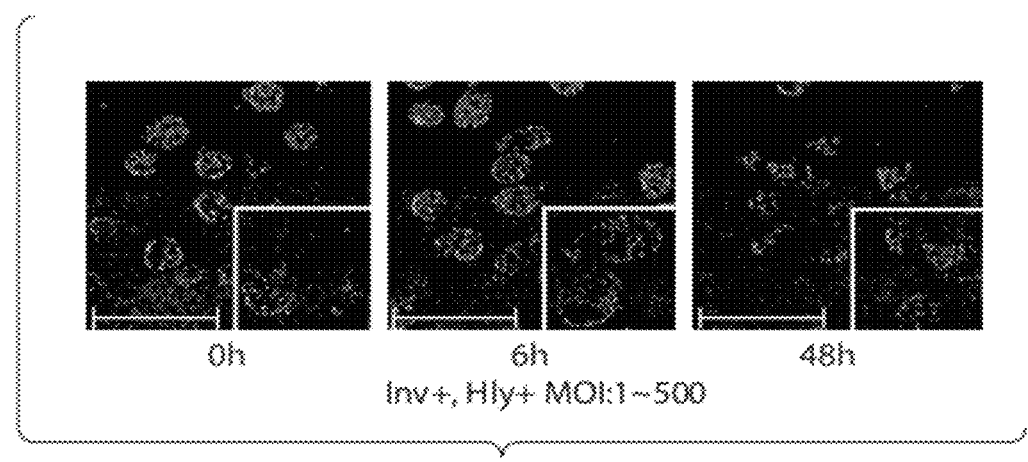
FIG. 8E is a photograph of cellular staining showing lack of significant bacterial replication in the absence of antibiotics beyond 2 h incubation.

To determine whether gene silencing requires continued bacterial replication inside target cells, tetracycline was employed to block intracellular bacterial replication and gentamycin to remove extracellular bacteria. SW 480 cells were incubated with E. coli for 2 h followed by tetracycline treatment initiated at different times. As shown in FIG. 8D, following the initial 2 h infection time, an additional 2 h incubation time without tetracycline induced near maximum gene silencing; further delay in tetracycline treatment had no further enhancing effect on the degree of gene silencing. Surprisingly, there was no evidence of significant intracellular bacterial replication in the absence of tetracycline at 6 h and 48 h (FIG. 8E), which is likely due to the function of lysosomes and other intracellular anti-bacterial mechanisms (Roy et al., Science 304, 1515-1518 (2004) and Battistoni et al., Infect. Immun. 68, 30-37 (2000). These results show that transkingdom RNAi is not dependent on persistent bacterial replication inside target cells after the initial infection (2 h) and incubation time (2 h).

Figure 9A:
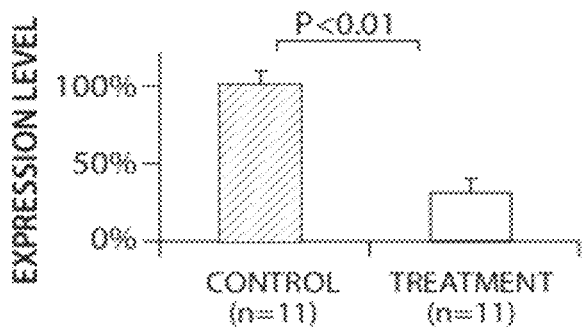
FIG. 9A is a graph showing that oral administration of *E. coli* expressing shRNA against β-catenin in mice leads to significant reduction of β-catenin expression in the intestinal epithelium.
Figure 9B:
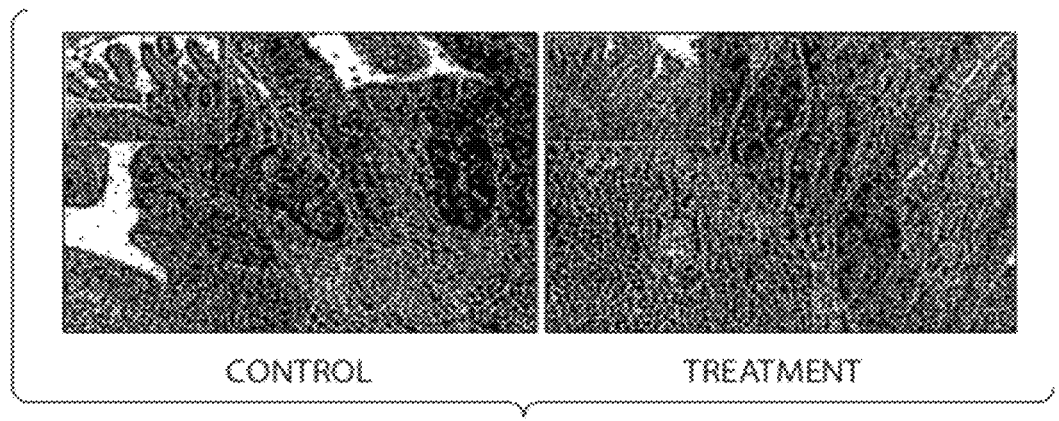
FIG. 9B is a photograph of immunohistochemistry staining of intestinal epithelium with or without treatment.
Figure 9C:
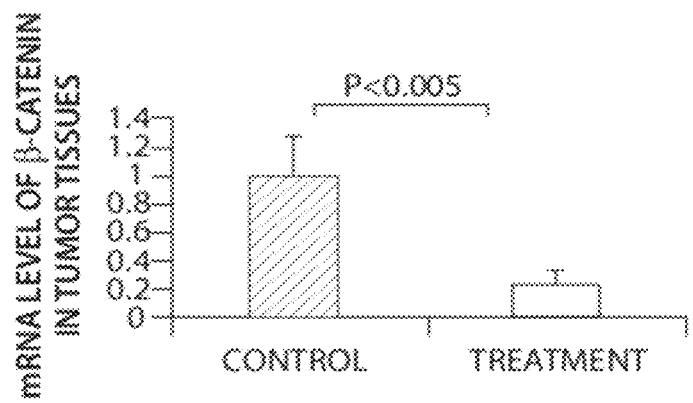
FIG. 9C is a graph showing a decrease in β-catenin mRNA expression following treatment.
Figure 9D:
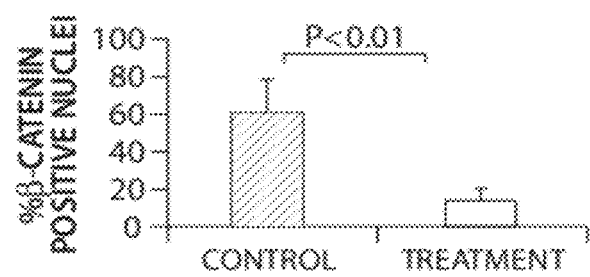
FIG. 9D is a graph showing a decrease in β-catenin protein expression following treatment.
Figure 9E:
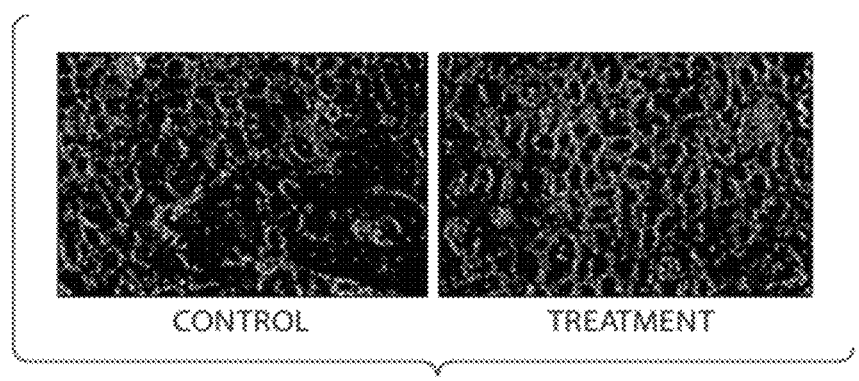
FIG. 9E is a photograph of immunohistochemistry staining showing decrease in β-catenin protein expression following treatment.
Figure 10:
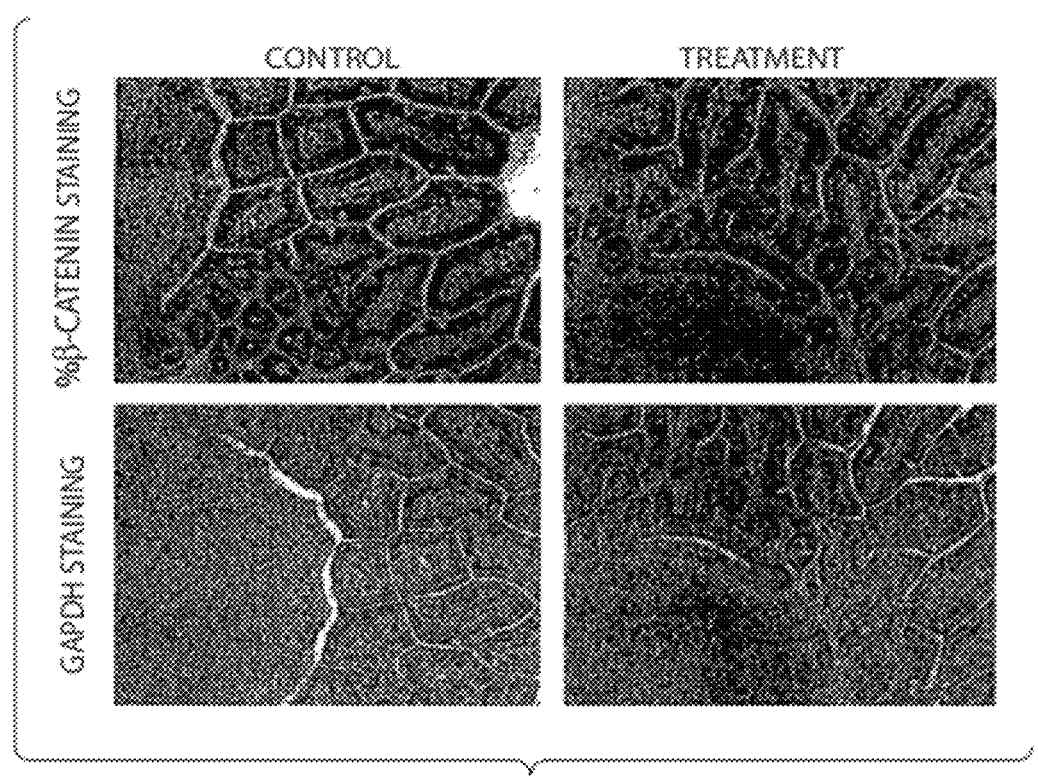
FIG. 10 is a photograph of immunohistochemistry staining showing that GAPDH expression is not altered by *E. coli* expressing shRNA against β-catenin after oral dosing in mice.

It was next determined if the transkingdom RNAi approach works in vivo. E. coli expressing shRNA against β-catenin were administered to mice orally. An inoculum of $5 \times 10^{10}$ was administered orally five times per week, which is comparable to a human dosage of the probiotic E. coli Nissle 1917. Most of the inoculum is eliminated during passage through the bactericidal environment in the upper GI tract. Mice were treated with E. coli expressing shRNA against mouse β-catenin or with E. coli containing the corresponding plasmid vector. Treatment was continued for four weeks before the analysis of gene silencing by immunohistochemistry. As shown in FIGS. 9A and 9B, β-catenin expression was silenced in the intestinal epithelium by E. coli expressing β-catenin shRNA (P<0.01), not by the control E. coli. As a control, GAPDH expression was not reduced (FIG. 10). The gene silencing effect was more pronounced in the regions of or adjacent to the Peyer's patches (FIG. 9B). Treatment was well tolerated with no gross or microscopic signs of epithelial damage or ulcerations (FIG. 9B). These results show that mammals respond to E. coli expressing specific shRNA with powerful local RNAi in vivo.

The transkingdom RNAi approach was investigated to determine if it can be used to silence a disease gene after systemic dosing. Intravenous administration of therapeutic bacteria has been tested in clinical trials with demonstrated safety in cancer patients (Toso et al., J. Clin. Oncol. 20, 142-52 (2002)). Nude mice with xenografted human colon cancer were treated intravenously with of $10^8$ cfu of E. coli encoding shRNA against human β-catenin. Three doses were given at a 5-day interval. The treatments were well tolerated without adverse effects. As shown in FIG. 9, treatment with E. coli encoding shRNA against β-catenin resulted in significant decrease in β-catenin mRNA (p<0.005, FIG. 9C) and protein (p<0.01, FIGS. 9D and 9E) in the tumor tissues. These data show that bacteria-mediated transkingdom RNAi can silence a disease gene in a distant part of the body after systemic administration.

These results show that gene silencing can be achieved through a transkingdom system. Importantly, the potency and specificity of RNAi is preserved. Non-pathogenic E. coli has been used clinically as probiotics with demonstrated safety (Rembacken et al., Lancet 354, 635 (1999)). Therefore, this transkingdom system provides a practical and clinically compatible way to deliver RNA interference for medical indications. This E. coli-based RNAi technology also provides a convenient vector system for conducting RNAi-based functional studies of genes. Finally, the results invite an intriguing possibility that such exchange of interfering RNA may occur in nature under cohabitive, infectious, or symbiotic conditions.

What is claimed is:

1. An invasive bacterium comprising a prokaryotic vector comprising one or more DNA molecules encoding one or more siRNAs, at least one prokaryotic promoter, at least one Hly A gene and at least one Inv gene.

2. A prokaryotic vector comprising at least one DNA molecule encoding one or more siRNAs, at least one prokaryotic promoter, at least one HlyA gene and at least one Inv gene.

3. The invasive bacterium of claim 1, wherein the invasive bacterium is non-pathogenic or non-virulent.

4. The invasive bacterium of claim 1, wherein the invasive bacterium is an attenuated strain selected from *Listeria, Shigella, Salmonella, E. Coli*, and *Bifidobacteriae*.

5. The invasive bacterium of claim 4, wherein the *Salmonella* is an attenuated strain of *Salmonella typhimurium* species.

6. The invasive bacterium of claim 5, wherein the attenuated strain of *Salmonella typhimurium* is SL7207 or VNP20009.

7. The invasive bacterium of claim 4, wherein the E. *Coli* is BM2710.

* * * * *

```
                          SEQUENCE LISTING

<160> NUMBER OF SEQ ID NOS: 8

<210> SEQ ID NO 1
<211> LENGTH: 64
<212> TYPE: DNA
<213> ORGANISM: Artificial sequence
<220> FEATURE:
<223> OTHER INFORMATION: Chemically synthesized primer

<400> SEQUENCE: 1
gatcccgttg gagctgttgg cgtagttcaa gagactacgc caacagctcc aactttttg        60 gaaa                                                                     64

<210> SEQ ID NO 2
<211> LENGTH: 64
<212> TYPE: DNA
<213> ORGANISM: Artificial sequence
<220> FEATURE:
<223> OTHER INFORMATION: Chemically synthesized primer

<400> SEQUENCE: 2
agcttttcca aaaagttgg agctgttggc gtagtctctt gaactacgcc aacagctcca         60
acgg                                                                     64

<210> SEQ ID NO 3
<211> LENGTH: 64
<212> TYPE: DNA
<213> ORGANISM: Artificial sequence
<220> FEATURE:
<223> OTHER INFORMATION: Chemically synthesized primer
```

```
<400> SEQUENCE: 3
gatcccagct gatattgatg gacagttcaa gagactgtcc atcaatatca gcttttttg      60 gaaa                                                                   64

<210> SEQ ID NO 4
<211> LENGTH: 64
<212> TYPE: DNA
<213> ORGANISM: Artificial sequence
<220> FEATURE:
<223> OTHER INFORMATION: Chemically synthesized primer

<400> SEQUENCE: 4
agcttttcca aaaaagctg atattgatgg acagtctctt gaactgtcca tcaatatcag      60
ctgg                                                                   64

<210> SEQ ID NO 5
<211> LENGTH: 64
<212> TYPE: DNA
<213> ORGANISM: Artificial sequence
<220> FEATURE:
<223> OTHER INFORMATION: Chemically synthesized primer

<400> SEQUENCE: 5
gatcccgacg taaacggcca caagtttcaa gagaacttgt ggccgtttac gtcttttttg     60
gaaa                                                                   64

<210> SEQ ID NO 6
<211> LENGTH: 64
<212> TYPE: DNA
<213> ORGANISM: Artificial sequence
<220> FEATURE:
<223> OTHER INFORMATION: Chemically synthesized primer

<400> SEQUENCE: 6
agcttttcca aaaagacgt aaacggccac aagttctctt gaaacttgtg gccgtttacg     60
tcgg                                                                   64

<210> SEQ ID NO 7
<211> LENGTH: 30
<212> TYPE: DNA
<213> ORGANISM: Artificial sequence
<220> FEATURE:
<223> OTHER INFORMATION: Chemically synthesized primer

<400> SEQUENCE: 7
ccctcctttg attagtatat tcctatctta                                       30

<210> SEQ ID NO 8
<211> LENGTH: 30
<212> TYPE: DNA
<213> ORGANISM: Artificial sequence
<220> FEATURE:
<223> OTHER INFORMATION: Chemically synthesized primer

<400> SEQUENCE: 8
aagcttttaa atcagcaggg gtcttttttgg                                      30
```